US012653814B2

(12) United States Patent
Lee et al.

(10) Patent No.: US 12,653,814 B2
(45) Date of Patent: Jun. 16, 2026

(54) BENZIMIDAZOLONE-BASED CINNAMAMIDE DERIVATIVE AS TRPV1 ANTAGONIST AND PHARMACEUTICAL COMPOSITION FOR TREATMENT OR PREVENTION OF PAIN CONTAINING SAME AS ACTIVE INGREDIENT

(71) Applicant: JMACKEM CO., LTD, Seoul (KR)

(72) Inventors: Jeewoo Lee, Seoul (KR); Jihyae Ann, Seoul (KR)

(73) Assignee: JMACKEM CO., LTD, Seoul (KR)

( * ) Notice: Subject to any disclaimer, the term of this patent is extended or adjusted under 35 U.S.C. 154(b) by 748 days.

(21) Appl. No.: 17/801,289

(22) PCT Filed: Mar. 10, 2021

(86) PCT No.: PCT/KR2021/002963
§ 371 (c)(1),
(2) Date: Aug. 22, 2022

(87) PCT Pub. No.: WO2021/215656
PCT Pub. Date: Oct. 28, 2021

(65) Prior Publication Data

US 2023/0147428 A1 May 11, 2023

(30) Foreign Application Priority Data

Apr. 22, 2020 (KR) ........................ 10-2020-0048788

(51) Int. Cl.

| | |
|---|---|
| ***A61K 31/4545*** | (2006.01) |
| ***A23L 33/10*** | (2016.01) |
| ***A61K 9/00*** | (2006.01) |
| ***A61K 9/08*** | (2006.01) |
| ***A61K 9/16*** | (2006.01) |
| ***A61K 9/20*** | (2006.01) |
| ***A61K 9/48*** | (2006.01) |
| ***A61K 31/07*** | (2006.01) |
| ***A61K 31/197*** | (2006.01) |
| ***A61K 31/355*** | (2006.01) |
| ***A61K 31/375*** | (2006.01) |
| ***A61K 31/4184*** | (2006.01) |
| ***A61K 31/4188*** | (2006.01) |
| ***A61K 31/427*** | (2006.01) |
| ***A61K 31/4415*** | (2006.01) |
| ***A61K 31/4439*** | (2006.01) |
| ***A61K 31/455*** | (2006.01) |
| ***A61K 31/519*** | (2006.01) |
| ***A61K 31/525*** | (2006.01) |
| ***A61K 31/5377*** | (2006.01) |

(Continued)

(52) U.S. Cl.
CPC .......... *A61K 31/4545* (2013.01); *A23L 33/10* (2016.08); *A61K 9/0053* (2013.01); *A61K 9/0095* (2013.01); *A61K 9/08* (2013.01); *A61K 9/1623* (2013.01); *A61K 9/2013* (2013.01); *A61K 9/2018* (2013.01); *A61K 9/2059* (2013.01); *A61K 9/4858* (2013.01); *A61K 9/4866* (2013.01); *A61K 31/07* (2013.01); *A61K 31/197* (2013.01); *A61K 31/355* (2013.01); *A61K 31/375* (2013.01); *A61K 31/4184* (2013.01); *A61K 31/4188* (2013.01); *A61K 31/427* (2013.01); *A61K 31/4415* (2013.01); *A61K 31/4439* (2013.01); *A61K 31/455* (2013.01); *A61K 31/519* (2013.01); *A61K 31/525* (2013.01); *A61K 31/5377* (2013.01); *A61K 31/714* (2013.01); *A61K 33/00* (2013.01); *A61K 33/06* (2013.01); *A61K 33/10* (2013.01); *A61K 33/26* (2013.01); *A61K 33/30* (2013.01); *A61K 47/02* (2013.01); *A61K 47/26* (2013.01); *A61P 29/00* (2018.01); *C07D 235/26* (2013.01); *C07D 401/12* (2013.01); *C07D 401/14* (2013.01); *C07D 403/12* (2013.01); *C07D 405/14* (2013.01); *C07D 409/14* (2013.01); *C07D 413/14* (2013.01); *C07D 417/12* (2013.01); *A23V 2002/00* (2013.01)

(58) Field of Classification Search
CPC .................................................. A61K 31/4545
See application file for complete search history.

(56) References Cited

U.S. PATENT DOCUMENTS

| | | | |
|---|---|---|---|
| 2005/0004133 A1 | 1/2005 | Makings et al. | |
| 2009/0264424 A1 | 10/2009 | Bo et al. | |
| 2017/0044132 A1 | 2/2017 | Hirayama et al. | |

FOREIGN PATENT DOCUMENTS

| | | |
|---|---|---|
| JP | 2009067784 A | 4/2009 |
| KR | 1020130065634 A | 6/2013 |

(Continued)

OTHER PUBLICATIONS

International Search Report from corresponding PCT/KR2021/002963 dated Jun. 17, 2021.

(Continued)

*Primary Examiner* — John S Kenyon
*Assistant Examiner* — Sara Elizabeth Bell
(74) *Attorney, Agent, or Firm* — CAESAR RIVISE, PC

(57) ABSTRACT

The present invention relates to a benzimidazolone-based cinnamamide derivative as a TRPV1 antagonist and a pharmaceutical composition for treating or preventing pain containing the same as an active ingredient. The example compounds provided in one aspect of the present invention block the TRPV1 activation caused by capsaicin, a TRPV1 receptor activator, but induce an appropriate inhibition of about 20% to 80% of pH, thereby the compounds have effects of alleviating pain and effectively reducing side effects such as abnormal body temperature.

10 Claims, No Drawings

(51) Int. Cl.

| | |
|---|---|
| ***A61K 31/714*** | (2006.01) |
| ***A61K 33/00*** | (2006.01) |
| ***A61K 33/06*** | (2006.01) |
| ***A61K 33/10*** | (2006.01) |
| ***A61K 33/26*** | (2006.01) |
| ***A61K 33/30*** | (2006.01) |
| ***A61K 47/02*** | (2006.01) |
| ***A61K 47/26*** | (2006.01) |
| ***A61P 29/00*** | (2006.01) |
| ***C07D 235/26*** | (2006.01) |
| ***C07D 401/12*** | (2006.01) |
| ***C07D 401/14*** | (2006.01) |
| ***C07D 403/12*** | (2006.01) |
| ***C07D 405/14*** | (2006.01) |
| ***C07D 409/14*** | (2006.01) |
| ***C07D 413/14*** | (2006.01) |
| ***C07D 417/12*** | (2006.01) |

(56) References Cited

FOREIGN PATENT DOCUMENTS

| | | | |
|---|---|---|---|
| WO | 2004108133 | A2 | 12/2004 |
| WO | 2011120604 | A1 | 10/2011 |

OTHER PUBLICATIONS

English abstract for JP 2009067784 A (2009).

Doherty et al. (2005). Discovery of potent, orally available vanilloid receptor-1 antagonists. Structure-activity relationship of N-Aryl cinnamides. Journal of Medicinal Chemistry, 48, 71-90.

Viswanadhan et al. (2007). Three-dimensional quantitative structure-activity relationships and activity predictions of human TRPV1 channel antagonists: comparative molecular field analysis and comparative molecular similarity index analysis of cinnamides. Journal of Medicinal Chemistry, 50, 5608-5619.

BENZIMIDAZOLONE-BASED CINNAMAMIDE DERIVATIVE AS TRPV1 ANTAGONIST AND PHARMACEUTICAL COMPOSITION FOR TREATMENT OR PREVENTION OF PAIN CONTAINING SAME AS ACTIVE INGREDIENT

CROSS-REFERENCE TO RELATED APPLICATIONS

This application is a U.S. National Phase Application of PCT/KR2021/002963, filed Mar. 10, 2021, which claims priority to KR 10-2020-0048788, filed Apr. 22, 2020, the contents of which applications are incorporated herein by reference in their entireties for all purposes.

BACKGROUND OF THE INVENTION

1. Field of the Invention

The present invention relates to a benzimidazolone-based cinnamamide derivative as a TRPV1 antagonist and a pharmaceutical composition for treating or preventing pain containing the same as an active ingredient.

2. Description of the Related Art

Transient receptor potential vanilloid-1 (TRPV1) is one of the subfamily of TRP (transient receptor potential) channel, a cation channel protein found in various tissues of animals, and is a non-selective cation channel mainly expressed in primary sensory neurons. In addition, TRPV1 plays an important role in pain transmission as a nociceptor and pain-sensing transducer involved in transduction, the first step of the nociceptive pathway, which is a process of accepting pain. TRPV1 also maintains the inflammatory state that appears after tissue damage caused by trauma, infection, surgery, burns, and disease and is involved in inflammatory temperature-hypersensitivity reaction.

In other words, TRPV1 is a 'gateway of pain' that recognizes and transmits pain in the human body, and through inhibition of TRPV1 function, it can selectively block inappropriate pain perception while maintaining normal sensation, thus TRPV1 is in the spotlight as a target for the development of analgesics.

Research on the development of analgesics targeting TRPV1 is largely divided into two mechanisms: agonists and antagonists. In the case of agonists, like ligands, they bind to receptors and deliver pain, and show analgesic effects through desensitization after the threshold. Therefore, agonists have side effects such as initial pain, burning pain and discomfort, so they are being developed only as transdermal analgesics. In contrast, TRPV1 antagonists bind to TRPV1 receptors competitively with the ligands and inhibit pain transmission itself by TRPV1. Therefore, TRPV1 antagonists do not have side effects such as agonist-induced burning sensation and initial pain, and also have no strong irritation, so they can be developed as oral formulations.

Specifically, TRPV1 antagonists are spotlighted as a target for the development of new nonopioid analgesics applicable to neuropathic pain, inflammatory pain and cancer pain, which require the development of specialized therapeutic agents due to low efficacy and side effects. In fact, a number of multinational pharmaceutical companies, including Abbott and Amgen, have conducted the development of TRPV1 antagonists. As a result of evaluating the efficacy of low-molecular TRPV1 antagonists in non-clinical animal experiments, the efficacy of TRPV1 antagonists showing selective and strong antagonism was confirmed.

However, the first-generation TRPV1 antagonist ABT-102, which has been reported as a strong TRPV1 antagonist, has been shown to increase body temperature lasting more than 2 days in rodents. In the case of AMG 517 developed by Amgen, it showed excellent analgesic efficacy as an antagonist, but it is known that the subject's body temperature rose to 40.2° C. and lasted for 1 to 5 days during clinical trials, resulting in a very fatal side effect. In addition, it was confirmed that some TRPV1 antagonists, including Amgen's AMG7905 and AMG8562, cause hypothermia even in the absence of partial agonism. Therefore, in the development of TRPV1 antagonists, the resolution of abnormal body temperature is raised as an important issue.

The side effect of raising body temperature of most of the first-generation TRPV1 antagonists developed so far is presumed to be due to antagonism against all activators (capsaicin, heat, pH, NADA, etc.) of the TRPV1 receptor. In particular, capsaicin, one of alkaloids, when ingested, stimulates TRPV1, one of the receptor activation channels, and does not actually increase the temperature, but induces intense fever.

In addition, it has been reported that blocking 100% of pH among the TRPV1 receptor activators caused an increase in body temperature, and blocking 20% or less caused proton activation at a high concentration to cause a decrease in body temperature. That is, in the development of TRPV1 antagonists, while blocking TRPV1 activation due to capsaicin and heat, overcoming the abnormal body temperature phenomenon by deriving a selective key strategy that moderately inhibits pH (20%-80%) is the most important task.

Referring to the prior art, Patent Reference 1 (WO 2011/120604 A1) discloses a TRPV1 antagonist compound and a pharmaceutical composition comprising the same as an active ingredient, and the compound inhibits the vanilloid receptor TRPV1, thereby alleviating pain and treating diseases such as dry eyes.

On the other hand, the compound of the present invention inhibits the TRPV1 activation caused by capsaicin, but exhibits a TRPV1 inhibitory activity of 20%-80% with respect to pH, thereby having an analgesic effect and no side effect of body temperature change, and has excellent absorption rate in the body. Therefore, the compound of the present invention has the differences described below from the contents of Patent Reference 1 (WO 2011/120604 A1) mentioned above.

First, in the compound of the present invention, the A region is 4-amino-1,3-dihydro-2H-benzo[d]imidazole-2-one derivative, the B region (linker part) is acrylamide, propanamide or cyclopropane-1-carboxamide, and the C region is phenyl, pyridine, pyrazole or thiazole. On the other hand, in the compound disclosed in Patent Reference 1 (WO 2011/120604 A1), the A region is often benzoheterocycloalkene, the B region is urea or amide, and other substituents including the C region are different. Therefore, the compound has a different chemical structure from the compound of the present invention as a whole.

In addition, the compound of the present invention blocks the TRPV1 activation caused by capsaicin and heat, but exhibits a TRPV1 inhibitory activity of 20%-80% with respect to pH, so that it is possible to prepare an analgesic having an analgesic effect, but not having an abnormal body temperature effect and having an excellent absorption rate in the body. On the other hand, the Patent Reference 1 (WO 2011/120604 A1) mentioned above only discloses an inhibitory effect on the TRPV1 activation caused by capsaicin in experimental examples, but does not disclose the TRPV1 inhibitory activity of a certain range for pH, the side effect of body temperature change and the absorption rate of the compound. Therefore, there is a difference between the compound of the present invention and the compound of the Patent Reference 1 in terms of the effectiveness of the invention.

That is, the compound of the present invention inhibits the TRPV1 activation caused by capsaicin, but exhibits the TRPV1 inhibitory activity of 20%-80% with respect to pH, so it has an analgesic effect, has no side effect of body temperature change, and has an excellent absorption rate in the body. Therefore, the present inventors have completed the present invention by demonstrating that the compound can be effectively used for analgesic.

SUMMARY OF THE INVENTION

It is an object of the present invention to provide a benzimidazolone-based cinnamamide derivative compound that blocks the TRPV1 activation caused by capsaicin, an activator of the TRPV1 receptor, but induces an appropriate inhibition of 20% to 80% of pH to relieve pain and effectively reduce side effects such as abnormal body temperature.

It is another object of the present invention to provide a pharmaceutical composition for preventing or treating pain containing the above compound as an active ingredient.

It is another object of the present invention to provide a health functional food composition for preventing or ameliorating pain containing the above compound as an active ingredient.

It is another object of the present invention to provide a method for treating pain comprising a step of administering the above compound to a subject in need.

It is another object of the present invention to provide the above compound for use in the prevention or treatment of pain.

It is another object of the present invention to provide a use of the above compound for the preparation of a medicament for the prevention or treatment of pain.

To achieve the above objects, in one aspect of the present invention, the present invention provides a compound represented by formula 1 described herein, a stereoisomer thereof, a solvate thereof, a hydrate thereof or a pharmaceutically acceptable salt thereof.

In another aspect of the present invention, the present invention provides a pharmaceutical composition for preventing or treating pain containing the above compound as an active ingredient.

In another aspect of the present invention, the present invention provides a health functional food composition for preventing or ameliorating pain containing the above compound as an active ingredient.

In another aspect of the present invention, the present invention provides a method for treating pain comprising a step of administering the above compound to a subject in need.

In another aspect of the present invention, the present invention provides the above compound for use in the prevention or treatment of pain.

In another aspect of the present invention, the present invention provides a use of the above compound for the preparation of a medicament for the prevention or treatment of pain.

Advantageous Effect

The example compounds provided in one aspect of the present invention block the TRPV1 activation caused by capsaicin, a TRPV1 receptor activator, but induce an appropriate inhibition of about 20% to 80% of pH, thereby the compounds have effects of alleviating pain and effectively reducing side effects such as abnormal body temperature.

DESCRIPTION OF THE PREFERRED EMBODIMENTS

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely.

In addition, the "inclusion" of an element throughout the specification does not exclude other elements, but may include other elements, unless specifically stated otherwise.

In one aspect of the present invention, the present invention provides a compound represented by formula 1 below, a stereoisomer thereof, a solvate thereof, a hydrate thereof or a pharmaceutically acceptable salt thereof.

[Formula 1]

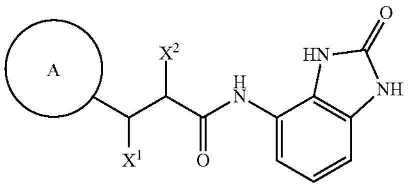

In formula 1 above, $X^1$ and $X^2$ are independently hydrogen, or form C═C double bond by linking with the carbon atom to which they are attached, or form 3-6 membered cycloalkylene by linking with the carbon atom to which they are attached; and

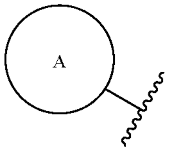

is unsubstituted or substituted 5-10 membered heteroaryl containing at least one heteroatom selected from the group consisting of N, O and S, or unsubstituted or substituted $C_{6-10}$ aryl, wherein the substituted 5-10 membered heteroaryl and $C_{6-10}$ aryl are independently 5-10 membered heteroaryl and $C_{6-10}$ aryl substituted with at least one substituent selected from the group consisting of $C_{1-12}$ straight or branched alkyl unsubstituted or substituted with at least one halogen or hydroxy group, $C_{1-12}$ straight or branched alkynyl, $C_{3-10}$ cycloalkyl unsubstituted or substituted with at least one $C_{1-5}$ straight or branched alkyl, 5-8 membered heterocycloalkyl unsubstituted or substituted with at least one $C_{1-5}$ straight or branched alkyl containing at least one heteroatom selected from the group consisting of N and O, —$NR^1R^2$, —$OR^3$, —$SR^4$, $C_{6-10}$ aryl unsubstituted or substituted with at least one halogen or $C_{1-5}$ straight or branched alkyl, and 5-8 membered heteroaryl containing at least one heteroatom selected from the group consisting of N, O and S, $R^1$ and $R^2$ are independently $C_{1-10}$ straight or branched alkyl, $R^3$ is $C_{1-10}$ straight or branched alkyl unsubstituted or substituted with at least one halogen, $C_{3-10}$ cycloalkyl, or $C_{3-10}$ cycloalkyl $C_{1-5}$ straight or branched alkyl unsubstituted or substituted with at least one methyl, $R^4$ is $C_{1-10}$ straight or branched alkyl unsubstituted or substituted with at least one halogen, $C_{3-10}$ cycloalkyl, or $C_{3-10}$ cycloalkyl $C_{1-5}$ straight or branched alkyl unsubstituted or substituted with at least one methyl.

In another aspect, $X^1$ and $X^2$ are independently hydrogen, or form C═C double bond by linking with the carbon atom to which they are attached, or form 3-5 membered cycloalkylene by linking with the carbon atom to which they are attached; and

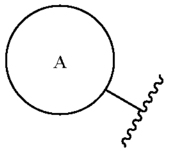

is unsubstituted or substituted 5-8 membered heteroaryl containing at least one heteroatom selected from the group consisting of N, O and S, or unsubstituted or substituted $C_{6-8}$ aryl, wherein the substituted 5-8 membered heteroaryl and $C_{6-8}$ aryl are independently 5-8 membered heteroaryl and $C_{6-8}$ aryl substituted with at least one substituent selected from the group consisting of $C_{1-10}$ straight or branched alkyl unsubstituted or substituted with at least one halogen or hydroxy group, $C_{1-10}$ straight or branched alkynyl, $C_{3-8}$ cycloalkyl unsubstituted or substituted with at least one $C_{1-5}$ straight or branched alkyl, 5-6 membered heterocycloalkyl unsubstituted or substituted with at least one $C_{1-5}$ straight or branched alkyl containing at least one heteroatom selected from the group consisting of N and O, —$NR^1R^2$, —$OR^3$, —$SR^4$, $C_{6-8}$ aryl unsubstituted or substituted with at least one halogen or $C_{1-5}$ straight or branched alkyl, and 5-6 membered heteroaryl containing at least one heteroatom selected from the group consisting of N, O and S, $R^1$ and $R^2$ are independently $C_{1-8}$ straight or branched alkyl, $R^3$ is $C_{1-8}$ straight or branched alkyl unsubstituted or substituted with at least one halogen, $C_{3-8}$ cycloalkyl, or $C_{3-8}$ cycloalkyl $C_{1-5}$ straight or branched alkyl unsubstituted or substituted with at least one methyl, $R^4$ is $C_{1-8}$ straight or branched alkyl unsubstituted or substituted with at least one halogen, $C_{3-8}$ cycloalkyl, or $C_{3-8}$ cycloalkyl $C_{1-5}$ straight or branched alkyl unsubstituted or substituted with at least one methyl.

In another aspect, $X^1$ and $X^2$ are independently hydrogen, or form C═C double bond by linking with the carbon atom to which they are attached, or form 3-4 membered cycloalkylene by linking with the carbon atom to which they are attached; and

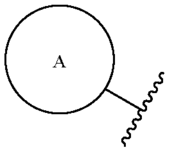

is unsubstituted or substituted 5-6 membered heteroaryl containing at least one heteroatom selected from the group consisting of N and S, or unsubstituted or substituted $C_6$ aryl, wherein the substituted 5-6 membered heteroaryl and $C_6$ aryl are independently 5-6 membered heteroaryl and $C_6$ aryl substituted with at least one substituent selected from the group consisting of $C_{1-7}$ straight or branched alkyl unsubstituted or substituted with at least one halogen or hydroxy group, $C_{1-7}$ straight or branched alkynyl, $C_{3-6}$ cycloalkyl unsubstituted or substituted with at least one $C_{1-5}$ straight or branched alkyl, 5-6 membered heterocycloalkyl unsubstituted or substituted with at least one $C_{1-5}$ straight or branched alkyl containing at least one heteroatom selected from the group consisting of N and O, —$NR^1R^2$, —$OR^3$, —$SR^4$, $C_6$ aryl unsubstituted or substituted with at least one halogen or $C_{1-5}$ straight or branched alkyl, and 5 membered heteroaryl containing at least one heteroatom selected from the group consisting of N, O and S, $R^1$ and $R^2$ are independently $C_{1-5}$ straight or branched alkyl, $R^3$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl, $R^4$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl.

In another aspect, $X^1$ and $X^2$ are independently hydrogen, or form C═C double bond by linking with the carbon atom to which they are attached, or form cyclopropylene by linking with the carbon atom to which they are attached; and

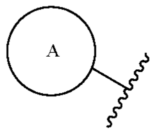

is

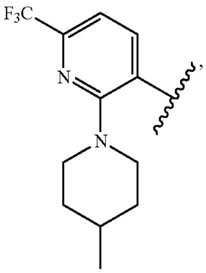

,

-continued
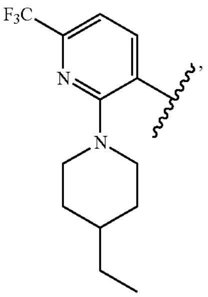,
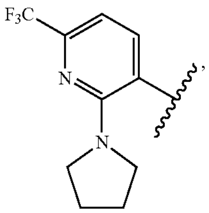,
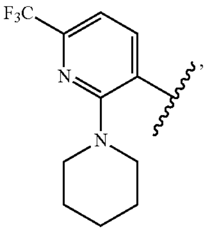,
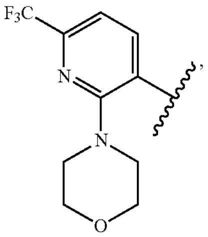,
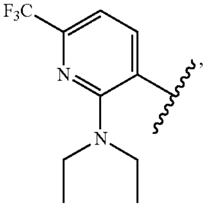,
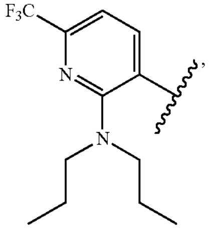,
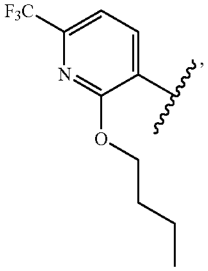,
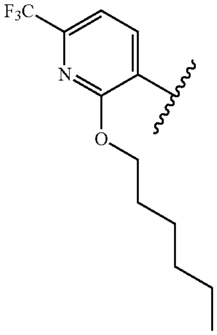,
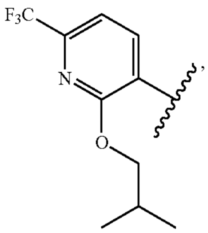,
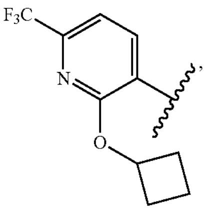,
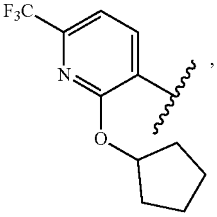,
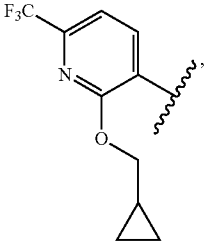,
-continued
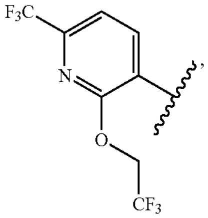,
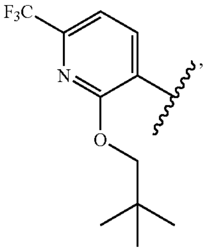,
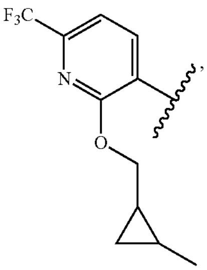,
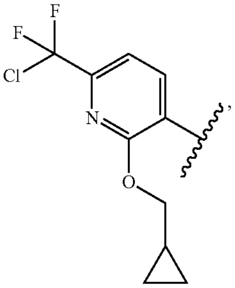,
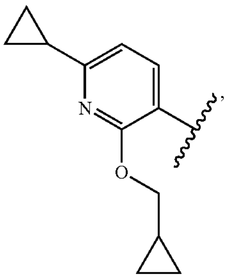,
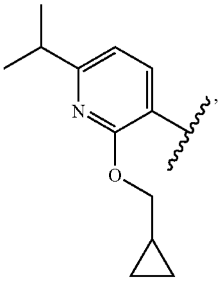,
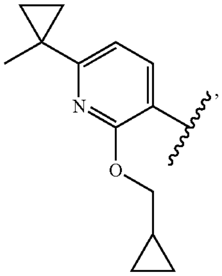,
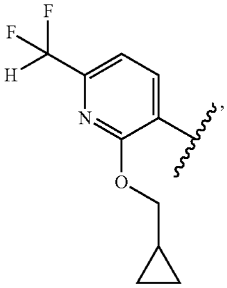,
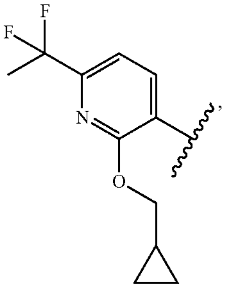,
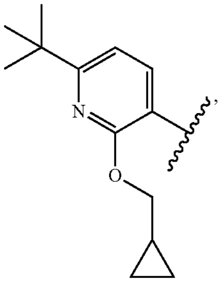,
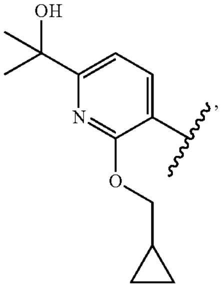,
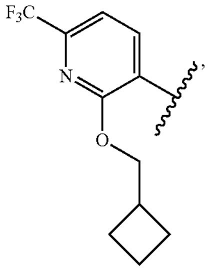, -continued
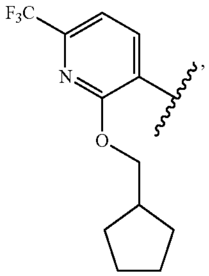
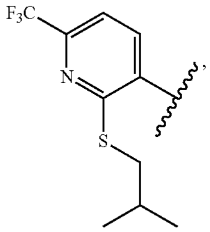
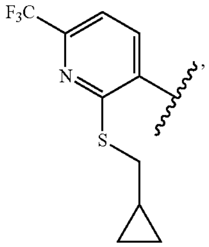
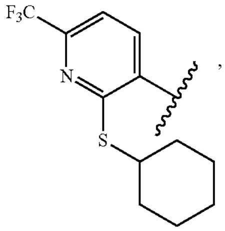
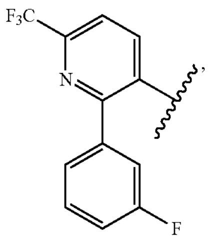
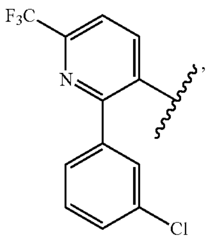
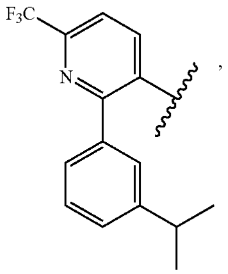
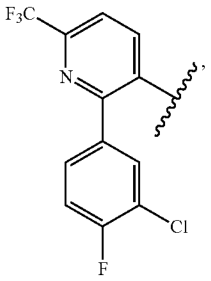
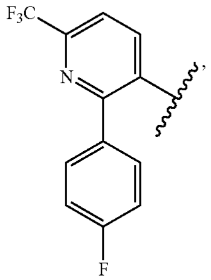
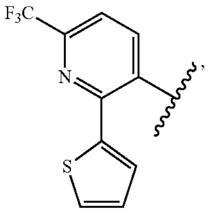
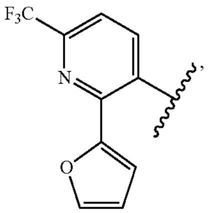
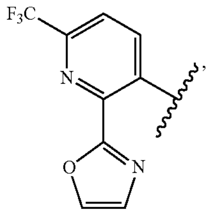
-continued
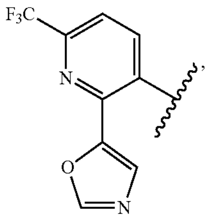
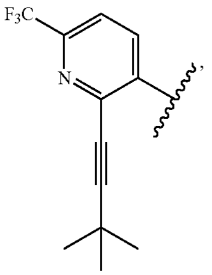
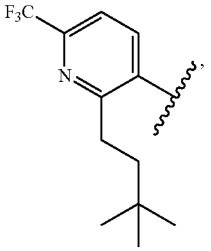
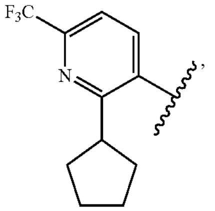
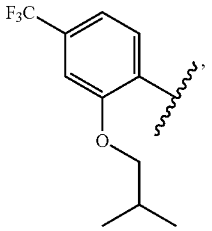
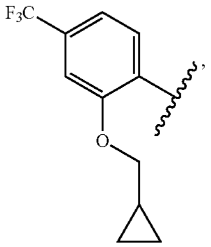
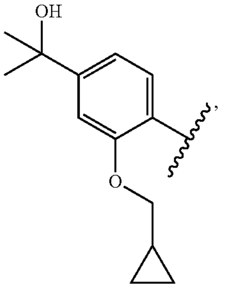
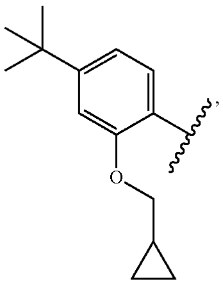
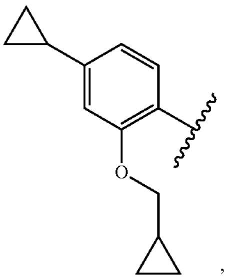
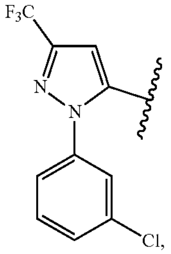
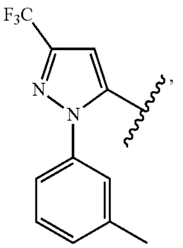
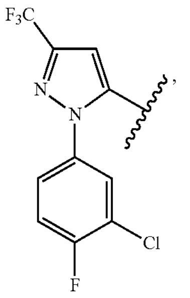

-continued

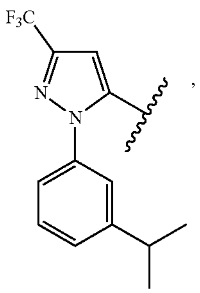

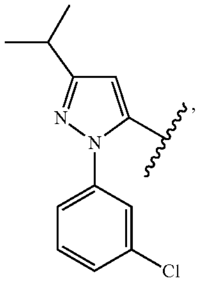

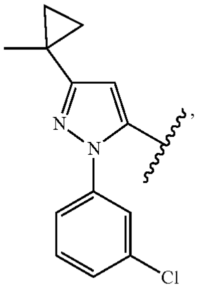

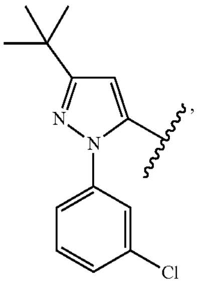

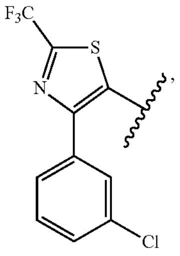

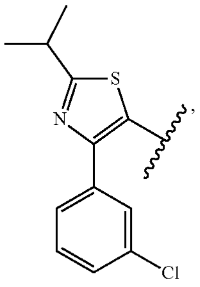

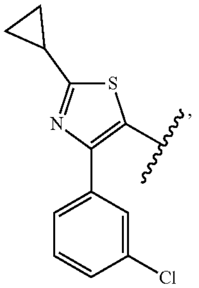

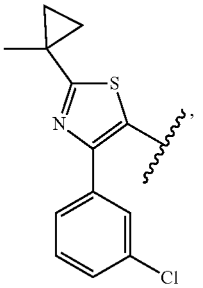

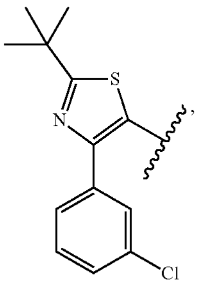

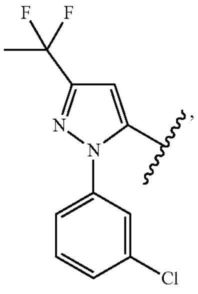

or

-continued

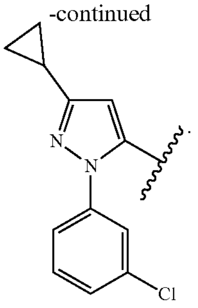

The compound represented by formula 1 can be any one compound selected from the following compound group.

(1) (E)-3-(2-(4-methylpiperidin-1-yl)-6-(trifluoromethyl)pyridin-3-yl)-N-(2-oxo-2,3-dihydro-1H-benzo[d]imidazol-4-yl)acrylamide;

(2) (E)-3-(2-(4-ethylpiperidin-1-yl)-6-(trifluoromethyl)pyridin-3-yl)-N-(2-oxo-2,3-dihydro-1H-benzo[d]imidazol-4-yl)acrylamide;

(3) (E)-N-(2-oxo-2,3-dihydro-1H-benzo[d]imidazol-4-yl)-3-(2-(pyrrolidin-1-yl)-6-(trifluoromethyl)pyridin-3-yl)acrylamide;

(4) (E)-N-(2-oxo-2,3-dihydro-1H-benzo[d]imidazol-4-yl)-3-(2-(piperidin-1-yl)-6-(trifluoromethyl)pyridin-3-yl)acrylamide;

(5) (E)-3-(2-morpholino-6-(trifluoromethyl)pyridin-3-yl)-N-(2-oxo-2,3-dihydro-1H-benzo[d]imidazol-4-yl)acrylamide;

(6) (E)-3-(2-(diethylamino)-6-(trifluoromethyl)pyridin-3-yl)-N-(2-oxo-2,3-dihydro-1H-benzo[d]imidazol-4-yl)acrylamide;

(7) (E)-3-(2-(dipropylamino)-6-(trifluoromethyl)pyridin-3-yl)-N-(2-oxo-2,3-dihydro-1H-benzo[d]imidazol-4-yl)acrylamide;

(8) (E)-3-(2-butoxy-6-(trifluoromethyl)pyridin-3-yl)-N-(2-oxo-2,3-dihydro-1H-benzo[d]imidazol-4-yl)acrylamide;

(9) (E)-3-(2-(hexyloxy)-6-(trifluoromethyl)pyridin-3-yl)-N-(2-oxo-2,3-dihydro-1H-benzo[d]imidazol-4-yl)acrylamide;

(10) (E)-3-(2-isobutoxy-6-(trifluoromethyl)pyridin-3-yl)-N-(2-oxo-2,3-dihydro-1H-benzo[d]imidazol-4-yl)acrylamide;

(11) (E)-3-(2-cyclobutoxy-6-(trifluoromethyl)pyridin-3-yl)-N-(2-oxo-2,3-dihydro-1H-benzo[d]imidazol-4-yl)acrylamide;

(12) (E)-3-(2-(cyclopentyloxy)-6-(trifluoromethyl)pyridin-3-yl)-N-(2-oxo-2,3-dihydro-1H-benzo[d]imidazol-4-yl)acrylamide;

(13) (E)-3-(2-(cyclopropylmethoxy)-6-(trifluoromethyl)pyridin-3-yl)-N-(2-oxo-2,3-dihydro-1H-benzo[d]imidazol-4-yl)acrylamide;

(14) (E)-N-(2-oxo-2,3-dihydro-1H-benzo[d]imidazol-4-yl)-3-(2-(2,2,2-trifluoroethoxy)-6-(trifluoromethyl)pyridin-3-yl)acrylamide;

(15) (E)-3-(2-(neopentyloxy)-6-(trifluoromethyl)pyridin-3-yl)-N-(2-oxo-2,3-dihydro-1H-benzo[d]imidazol-4-yl)acrylamide;

(16) (E)-3-(2-((2-methylcyclopropyl)methoxy)-6-(trifluoromethyl)pyridin-3-yl)-N-(2-oxo-2,3-dihydro-1H-benzo[d]imidazol-4-yl)acrylamide;

(17) (E)-3-(6-(chlorodifluoromethyl)-2-(cyclopropylmethoxy)pyridin-3-yl)-N-(2-oxo-2,3-dihydro-1H-benzo[d]imidazol-4-yl)acrylamide;

(18) (E)-3-(6-cyclopropyl-2-(cyclopropylmethoxy)pyridin-3-yl)-N-(2-oxo-2,3-dihydro-1H-benzo[d]imidazol-4-yl)acrylamide;
(19) (E)-3-(2-(cyclopropylmethoxy)-6-isopropylpyridin-3-yl)-N-(2-oxo-2,3-dihydro-1H-benzo[d]imidazol-4-yl)acrylamide;
(20) (E)-3-(2-(cyclopropylmethoxy)-6-(1-methylcyclopropyl)pyridin-3-yl)-N-(2-oxo-2,3-dihydro-1H-benzo[d]imidazol-4-yl)acrylamide;
(21) (E)-3-(2-(cyclopropylmethoxy)-6-(difluoromethyl)pyridin-3-yl)-N-(2-oxo-2,3-dihydro-1H-benzo[d]imidazol-4-yl)acrylamide;
(22) (E)-3-(2-(cyclopropylmethoxy)-6-(1,1-difluoroethyl)pyridin-3-yl)-N-(2-oxo-2,3-dihydro-1H-benzo[d]imidazol-4-yl)acrylamide;
(23) (E)-3-(6-(tert-butyl)-2-(cyclopropylmethoxy)pyridin-3-yl)-N-(2-oxo-2,3-dihydro-1H-benzo[d]imidazol-4-yl)acrylamide;
(24) (E)-3-(2-(cyclopropylmethoxy)-6-(2-hydroxypropan-2-yl)pyridin-3-yl)-N-(2-oxo-2,3-dihydro-1H-benzo[d]imidazol-4-yl)acrylamide;
(25) (E)-3-(2-(cyclobutylmethoxy)-6-(trifluoromethyl)pyridin-3-yl)-N-(2-oxo-2,3-dihydro-1H-benzo[d]imidazol-4-yl)acrylamide;
(26) (E)-3-(2-(cyclopentylmethoxy)-6-(trifluoromethyl)pyridin-3-yl)-N-(2-oxo-2,3-dihydro-1H-benzo[d]imidazol-4-yl)acrylamide;
(27) (E)-3-(2-(isobutylthio)-6-(trifluoromethyl)pyridin-3-yl)-N-(2-oxo-2,3-dihydro-1H-benzo[d]imidazol-4-yl)acrylamide;
(28) (E)-3-(2-((cyclopropylmethyl)thio)-6-(trifluoromethyl)pyridin-3-yl)-N-(2-oxo-2,3-dihydro-1H-benzo[d]imidazol-4-yl)acrylamide;
(29) (E)-3-(2-(cyclohexylthio)-6-(trifluoromethyl)pyridin-3-yl)-N-(2-oxo-2,3-dihydro-1H-benzo[d]imidazol-4-yl)acrylamide;
(30) (E)-3-(2-(3-fluorophenyl)-6-(trifluoromethyl)pyridin-3-yl)-N-(2-oxo-2,3-dihydro-1H-benzo[d]imidazol-4-yl)acrylamide;
(31) (E)-3-(2-(3-chlorophenyl)-6-(trifluoromethyl)pyridin-3-yl)-N-(2-oxo-2,3-dihydro-1H-benzo[d]imidazol-4-yl)acrylamide;
(32) (E)-3-(2-(3-isopropylphenyl)-6-(trifluoromethyl)pyridin-3-yl)-N-(2-oxo-2,3-dihydro-1H-benzo[d]imidazol-4-yl)acrylamide;
(33) (E)-3-(2-(3-chloro-4-fluorophenyl)-6-(trifluoromethyl)pyridin-3-yl)-N-(2-oxo-2,3-dihydro-1H-benzo[d]imidazol-4-yl)acrylamide;
(34) (E)-3-(2-(4-fluorophenyl)-6-(trifluoromethyl)pyridin-3-yl)-N-(2-oxo-2,3-dihydro-1H-benzo[d]imidazol-4-yl)acrylamide;
(35) (E)-N-(2-oxo-2,3-dihydro-1H-benzo[d]imidazol-4-yl)-3-(2-(thiophen-2-yl)-6-(trifluoromethyl)pyridin-3-yl)acrylamide;
(36) (E)-3-(2-(furan-2-yl)-6-(trifluoromethyl)pyridin-3-yl)-N-(2-oxo-2,3-dihydro-1H-benzo[d]imidazol-4-yl)acrylamide;
(37) (E)-3-(2-(oxazol-2-yl)-6-(trifluoromethyl)pyridin-3-yl)-N-(2-oxo-2,3-dihydro-1H-benzo[d]imidazol-4-yl)acrylamide;
(38) (E)-3-(2-(oxazol-5-yl)-6-(trifluoromethyl)pyridin-3-yl)-N-(2-oxo-2,3-dihydro-1H-benzo[d]imidazol-4-yl)acrylamide;
(39) (E)-3-(2-(3,3-dimethyl-1-butyn-1-yl)-6-(trifluoromethyl)pyridin-3-yl)-N-(2-oxo-2,3-dihydro-1H-benzo[d]imidazol-4-yl)acrylamide;
(40) (E)-3-(2-(3,3-dimethylbutyl)-6-(trifluoromethyl)pyridin-3-yl)-N-(2-oxo-2,3-dihydro-1H-benzo[d]imidazol-4-yl)acrylamide;
(41) (E)-3-(2-cyclopentyl-6-(trifluoromethyl)pyridin-3-yl)-N-(2-oxo-2,3-dihydro-1H-benzo[d]imidazol-4-yl)acrylamide;
(42) (E)-3-(2-isobutoxy-4-(trifluoromethyl)phenyl)-N-(2-oxo-2,3-dihydro-1H-benzo[d]imidazol-4-yl)acrylamide;
(43) (E)-3-(2-(cyclopropylmethoxy)-4-(trifluoromethyl)phenyl)-N-(2-oxo-2,3-dihydro-1H-benzo[d]imidazol-4-yl)acrylamide;
(44) (E)-3-(2-(cyclopropylmethoxy)-4-(2-hydroxypropan-2-yl)phenyl)-N-(2-oxo-2,3-dihydro-1H-benzo[d]imidazol-4-yl)acrylamide;
(45) (E)-3-(4-(tert-butyl)-2-(cyclopropylmethoxy)phenyl)-N-(2-oxo-2,3-dihydro-1H-benzo[d]imidazol-4-yl)acrylamide;
(46) (E)-3-(4-cyclopropyl-2-(cyclopropylmethoxy)phenyl)-N-(2-oxo-2,3-dihydro-1H-benzo[d]imidazol-4-yl)acrylamide;
(47) (E)-3-(1-(3-chlorophenyl)-3-(trifluoromethyl)-1H-pyrazol-5-yl)-N-(2-oxo-2,3-dihydro-1H-benzo[d]imidazol-4-yl)acrylamide;
(48) (E)-N-(2-oxo-2,3-dihydro-1H-benzo[d]imidazol-4-yl)-3-(1-(m-tolyl)-3-(trifluoromethyl)-1H-pyrazol-5-yl)acrylamide;
(49) (E)-3-(1-(3-chloro-4-fluorophenyl)-3-(trifluoromethyl)-1H-pyrazol-5-yl)-N-(2-oxo-2,3-dihydro-1H-benzo[d]imidazol-4-yl)acrylamide;
(50) (E)-3-(1-(3-isopropylphenyl)-3-(trifluoromethyl)-1H-pyrazol-5-yl)-N-(2-oxo-2,3-dihydro-1H-benzo[d]imidazol-4-yl)acrylamide;
(51) (E)-3-(1-(3-chlorophenyl)-3-isopropyl-1H-pyrazol-5-yl)-N-(2-oxo-2,3-dihydro-1H-benzo[d]imidazol-4-yl)acrylamide;
(52) (E)-3-(1-(3-chlorophenyl)-3-(1-methylcyclopropyl)-1H-pyrazol-5-yl)-N-(2-oxo-2,3-dihydro-1H-benzo[d]imidazol-4-yl)acrylamide;
(53) (E)-3-(3-(tert-butyl)-1-(3-chlorophenyl)-1H-pyrazol-5-yl)-N-(2-oxo-2,3-dihydro-1H-benzo[d]imidazol-4-yl)acrylamide;
(54) (E)-3-(4-(3-chlorophenyl)-2-(trifluoromethyl)thiazol-5-yl)-N-(2-oxo-2,3-dihydro-1H-benzo[d]imidazol-4-yl)acrylamide;
(55) (E)-3-(4-(3-chlorophenyl)-2-isopropylthiazol-5-yl)-N-(2-oxo-2,3-dihydro-1H-benzo[d]imidazol-4-yl)acrylamide;
(56) (E)-3-(4-(3-chlorophenyl)-2-cyclopropylthiazol-5-yl)-N-(2-oxo-2,3-dihydro-1H-benzo[d]imidazol-4-yl)acrylamide;
(57) (E)-3-(4-(3-chlorophenyl)-2-(1-methylcyclopropyl)thiazol-5-yl)-N-(2-oxo-2,3-dihydro-1H-benzo[d]imidazol-4-yl)acrylamide;
(58) (E)-3-(2-(tert-butyl)-4-(3-chlorophenyl)thiazol-5-yl)-N-(2-oxo-2,3-dihydro-1H-benzo[d]imidazol-4-yl)acrylamide;
(59) 3-(2-isobutoxy-6-(trifluoromethyl)pyridin-3-yl)-N-(2-oxo-2,3-dihydro-1H-benzo[d]imidazol-4-yl)propaneamide;
(60) 3-(2-(cyclopropylmethoxy)-6-(trifluoromethyl)pyridin-3-yl)-N-(2-oxo-2,3-dihydro-1H-benzo[d]imidazol-4-yl)propaneimide;
(61) 2-(2-isobutoxy-6-(trifluoromethyl)pyridin-3-yl)-N-(2-oxo-2,3-dihydro-1H-benzo[d]imidazol-4-yl)cyclopropane-1-carboxamide;

(62) 2-(2-(cyclopropylmethoxy)-6-(trifluoromethyl)pyridin-3-yl)-N-(2-oxo-2,3-dihydro-1H-benzo[d]imidazol-4-yl)cyclopropane-1-carboxamide;

(63) 2-(1-(3-chlorophenyl)-3-(trifluoromethyl)-1H-pyrazol-5-yl)-N-(2-oxo-2,3-dihydro-1H-benzo[d]imidazol-4-yl)cyclopropane-1-carboxamide;

(64) 2-(1-(3-chlorophenyl)-3-(1,1-difluoroethyl)-1H-pyrazol-5-yl)-N-(2-oxo-2,3-dihydro-1H-benzo[d]imidazol-4-yl)cyclopropane-1-carboxamide;

(65) 2-(1-(3-chlorophenyl)-3-isopropyl-1H-pyrazol-5-yl)-N-(2-oxo-2,3-dihydro-1H-benzo[d]imidazol-4-yl)cyclopropane-1-carboxamide;

(66) 2-(1-(3-chlorophenyl)-3-cyclopropyl-1H-pyrazol-5-yl)-N-(2-oxo-2,3-dihydro-1H-benzo[d]imidazol-4-yl)cyclopropane-1-carboxamide;

(67) 2-(1-(3-chlorophenyl)-3-(1-methylcyclopropyl)-1H-pyrazol-5-yl)-N-(2-oxo-2,3-dihydro-1H-benzo[d]imidazol-4-yl)cyclopropane-1-carboxamide; and

(68) 2-(3-(tert-butyl)-1-(3-chlorophenyl)-1H-pyrazol-5-yl)-N-(2-oxo-2,3-dihydro-1H-benzo[d]imidazol-4-yl)cyclopropane-1-carboxamide.

In another aspect,

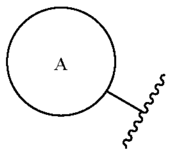

is unsubstituted or substituted 5-6 membered heteroaryl containing at least one heteroatom selected from the group consisting of N and S, wherein the substituted 5-6 membered heteroaryl is 5-6 membered heteroaryl substituted with two substituents selected from the group consisting of $C_{1-7}$ straight or branched alkyl unsubstituted or substituted with at least one halogen or hydroxy group, $C_{1-7}$ straight or branched alkynyl, $C_{3-6}$ cycloalkyl unsubstituted or substituted with at least one $C_{1-5}$ straight or branched alkyl, 5-6 membered heterocycloalkyl unsubstituted or substituted with at least one $C_{1-5}$ straight or branched alkyl containing at least one heteroatom selected from the group consisting of N and O, —$NR^1R^2$, —$OR^3$, —$SR^4$, $C_6$ aryl unsubstituted or substituted with at least one halogen or $C_{1-5}$ straight or branched alkyl, and 5 membered heteroaryl containing at least one heteroatom selected from the group consisting of N, O and S, $R^1$ and $R^2$ are independently $C_{1-5}$ straight or branched alkyl, $R^3$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl, $R^4$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl.

In another aspect,

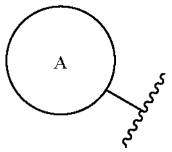

is unsubstituted or substituted pyridine, wherein the substituted pyridine is pyridine substituted with two substituents selected from the group consisting of $C_{1-7}$ straight or branched alkyl unsubstituted or substituted with at least one halogen or hydroxy group, $C_{1-7}$ straight or branched alkynyl, $C_{3-6}$ cycloalkyl unsubstituted or substituted with at least one $C_{1-5}$ straight or branched alkyl, 5-6 membered heterocycloalkyl unsubstituted or substituted with at least one $C_{1-5}$ straight or branched alkyl containing at least one heteroatom selected from the group consisting of N and O, —$NR^1R^2$, —$OR^3$, —$SR^4$, $C_6$ aryl unsubstituted or substituted with at least one halogen or $C_{1-5}$ straight or branched alkyl, and 5 membered heteroaryl containing at least one heteroatom selected from the group consisting of N, O and S, $R^1$ and $R^2$ are independently $C_{1-5}$ straight or branched alkyl, $R^3$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl, $R^4$ is $C_{1-7}$ straight or branched alkyl unsubstituted or substituted with at least one halogen, $C_{3-6}$ cycloalkyl, or $C_{3-6}$ cycloalkyl $C_{1-5}$ straight or branched alkyl unsubstituted or substituted with at least one methyl.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as trifluoroacetic acid, acetate, benzoic acid, citric acid, lactic acid, maleic acid, gluconic acid, methanesulfonic acid, 4-toluenesulfonic acid, tartaric acid and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, methylene chloride, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The term "hydrate" refers to a compound or a salt thereof of the present invention containing a stoichiometric or non-stoichiometric amount of water bound by a non-covalent intermolecular force. The hydrate of the compound represented by formula 1 of the present invention can contain a stoichiometric or non-stoichiometric amount of water bonded by a non-covalent intermolecular force. The hydrate can contain 1 equivalent or more of water, preferably 1 to 5 equivalents of water. The hydrate can be prepared by crystallizing the compound represented by formula 1, the isomer thereof, or the pharmaceutically acceptable salt thereof from water or the solvent containing water.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human.

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

In another aspect of the present invention, the present invention provides a pharmaceutical composition for preventing or treating pain containing the compound represented by formula 1, a stereoisomer thereof, a solvate thereof, a hydrate thereof or a pharmaceutically acceptable salt thereof as an active ingredient. At this time, the compound may exhibit a preventive or therapeutic activity for pain by inhibiting TRPV1 (transient receptor potential vanilloid-1) receptor activators. Preferably, the compound prevents or treats pain by suppressing capsaicin, a TRPV1 (transient receptor potential vanilloid-1) receptor activator, and inhibits pH in the range of 20% to 80% to reduce side effects such as abnormal body temperature.

The compound represented by formula 1 of the present invention or the pharmaceutically acceptable salt thereof can be administered orally or parenterally and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides an analgesic composition for treating or alleviating pain containing the compound represented by formula 1, a stereoisomer thereof, a solvate thereof, a hydrate thereof or a pharmaceutically acceptable salt thereof as an active ingredient. At this time, the compound may exhibit a therapeutic or alleviating activity for pain by inhibiting TRPV1 (transient receptor potential vanilloid-1) receptor activators. Preferably, the compound treats or alleviates pain by suppressing capsaicin, a TRPV1 (transient receptor potential vanilloid-1) receptor activator, and inhibits pH in the range of 20% to 80% to reduce side effects such as abnormal body temperature.

In another aspect of the present invention, the present invention provides a health functional food composition for preventing or ameliorating pain containing the compound represented by formula 1, a stereoisomer thereof, a solvate thereof, a hydrate thereof or a pharmaceutically acceptable salt thereof as an active ingredient. At this time, the compound may exhibit a preventive or ameliorating activity for pain by inhibiting TRPV1 (transient receptor potential vanilloid-1) receptor activators. Preferably, the compound prevents or ameliorates pain by suppressing capsaicin, a TRPV1 (transient receptor potential vanilloid-1) receptor activator, and inhibits pH in the range of 20% to 80% to reduce side effects such as abnormal body temperature.

The compound represented by formula 1 according to the present invention can be used as food additive. In that case, the compound can be added as it is or as mixed with other food components according to the conventional method. The mixing ratio of active ingredients can be regulated according to the purpose of use (prevention or amelioration). In general, the amount of the compound in health food can be added in an amount of 0.1 to 90 weight part based on the total weight of the food. However, if long term administration is required for health and hygiene or regulating health condition, the content can be lower than the above but higher content can be accepted as well since the compound has been proved to be very safe.

In addition, the health functional beverage composition of the present invention can additionally include various flavors or natural carbohydrates, etc, like other beverages in addition to the compound represented by formula 1. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g in 100 g of the composition of the present invention.

In addition to the ingredients mentioned above, the compound represented by formula 1 according to the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include fruit flesh addable to natural fruit juice, fruit beverages and vegetable beverages.

In another aspect of the present invention, the present invention provides a pharmaceutical kit for preventing or treating pain comprising a first component containing the compound represented by formula 1, a stereoisomer thereof, a solvate thereof, a hydrate thereof or a pharmaceutically acceptable salt thereof as an active ingredient; and a second component containing an analgesic as an active ingredient.

At this time, the analgesic can be used without limitation, as long as it is a known analgesic. The analgesic can be an anti-inflammatory analgesic (NSAID such as a COX inhibitor) or an opioid-based analgesic. Some examples of the analgesic may be acetaminophen, aspirin, ibuprofen, ketoprofen, meloxicam, diclofenac potassium, etodolac, sulindac, indomethacin, celecoxib, valdecoxib, rofecoxib, celecoxib, hydrocodone, oxymorphone, buprenorphine, fentanyl, hydromorphone, tramadol, and the like, or a combination thereof.

In another aspect of the present invention, the present invention provides a method for treating pain comprising a step of administering the above compound to a subject in need. In another aspect of the present invention, the present invention provides the above compound for use in the prevention or treatment of pain. In another aspect of the present invention, the present invention provides a use of the above compound for the preparation of a medicament for the prevention or treatment of pain.

The example compounds provided in one aspect of the present invention block the TRPV1 activation caused by capsaicin, a TRPV1 receptor activator, but induce an appropriate inhibition of about 20% to 80% of pH, thereby the compounds have effects of alleviating pain and effectively reducing side effects such as abnormal body temperature. These are directly supported by the examples and experimental examples to be described hereinafter.

Hereinafter, the present invention will be described in detail by the following examples and experimental examples.

However, the following examples and experimental examples are only for illustrating the present invention, and the contents of the present invention are not limited thereto.

SYNTHESIS

1. Synthesis of Compounds

1-1. Synthesis of A-Region

[Reaction Formula 1] Synthesis of A-region (4-amino-1,3-dihydro-2H-benzo [d] imidazol-2-one derivative)

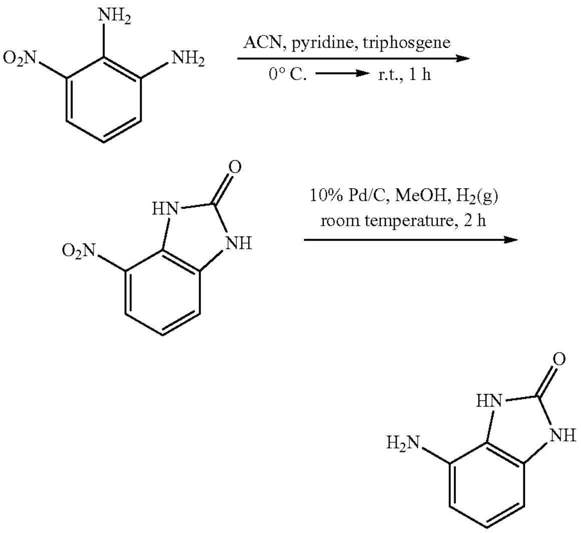

1-1-1. Synthesis of 4-Nitro-1,3-Dihydro-2H-benzo [d]imidazol-2-one

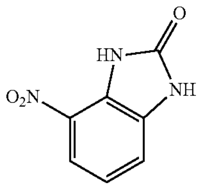 [SMILES: O=c1[nH]c2cccc([N+](=O)[O-])c2[nH]1]

3-Nitrobenzene-1,2-diamine (1 equivalent) was dissolved in acetonitrile, to which triphosgene (1.2 equivalent) was added dropwise at 0° C. for 3-5 minutes, followed by stirring at room temperature for 30 minutes, preferably for 1 hour. The reaction mixture was diluted by slowly adding water dropwise at 0° C., and when no more gas was generated and a dark yellow-green solid began to form, the reaction mixture was stirred at room temperature for 30 minutes, preferably for 1 hour. Then, the produced yellow-green solid was filtered and washed with water to give the target product 4-nitro-1,3-dihydro-2H-benzo[d]imidazol-2-one. (Yield: 80-89%)

1-1-2. Synthesis of 4-amino-1,3-dihydro-2H-benzo [d]imidazol-2-one

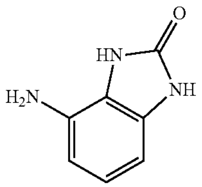

4-Nitro-1,3-dihydro-2H-benzo[d]imidazol-2-one (1 equivalent) obtained in the above reaction was hydrogenated with a reducing agent such as 10% palladium-activated carbon (Pd—C) dissolved in lower alcohol such as methanol, filtered, and the filtrate was dried under reduced pressure. The reactant was purified by flash column chromatography filled with silica gel using a mixed solvent of methylene chloride and methyl alcohol as an elution solvent to give the target compound 4-amino-1,3-dihydro-2H-benzo [d]imidazol-2-one. (Yield: 80-85%)

1-2. Synthesis of C-Region

Reaction Formula 2] Synthesis of pyridine C-region

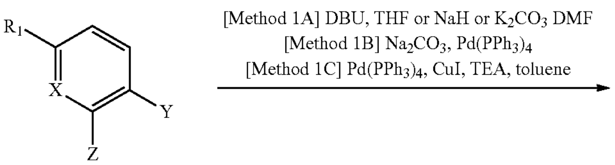

$R_1 = CF_3, C(CH_3)_3$
X = N, C
Y = CN, Br
Z = OH, F, Cl, SH

-continued

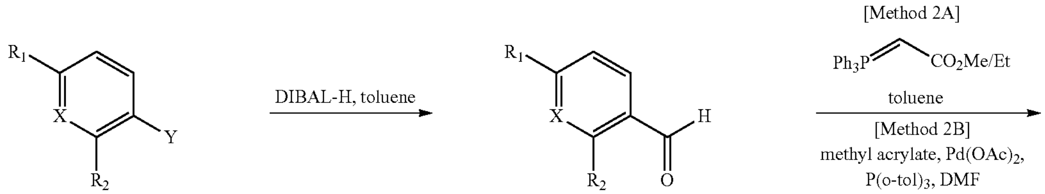

$R_1 = CF_3, C(CH_3)_3$
X = N, C
Y = CN, Br*
$R_2$ = methyl piperidine, ethylpiperidine, cyclopentyl, cyclohexyl, morpholine, diethylamine, dipropylamine, propoxy, hexyloxy, isobutoxy, cyclobutoxy, cyclopentyloxy, 2,2,2-trifluoroethoxy, neopentyloxy, 2-methylcyclopropyl)methoxy, cyclobutylmethoxy, cyclopentylmethoxy, (2,3-dimethylcyclopropyl)methoxy, isobutyl sulfane, cyclopropylmethyl sulfane, cyclohexyl sulfane, 3-fluorophenyl, 3-chlorophenyl, 3-isopropylphenyl, 3-chloro-4-fluorophenyl, 4-fluorophenyl, thiophen-2-yl, furan-2-yl, 3,3-dimethylbut-1-yn-1-yl, 3,3-dimethylbutyl, cyclobutyl, cyclopentyl, cyclohexyl
*Y = Br: direct coupling with methyl acrylate $R_1 = CF_3, C(CH_3)_3$
X = N, C
$R_2$ = methyl piperidine, ethylpiperidine, cyclopentyl, cyclohexyl, morpholine, diethylamine, dipropylamine, propoxy, hexyloxy, isobutoxy, cyclobutoxy, cyclopentyloxy, 2,2,2-trifluoroethoxy, neopentyloxy, 2-methylcyclopropyl)methoxy, cyclobutylmethoxy, cyclopentylmethoxy, (2,3-dimethylcyclopropyl)methoxy, isobutyl sulfane, cyclopropylmethyl sulfane, cyclohexyl sulfane, 3-fluorophenyl, 3-chlorophenyl, 3-isopropylphenyl, 3-chloro-4-fluorophenyl, 4-fluorophenyl, thiophen-2-yl, furan-2-yl, 3,3-dimethylbut-1-yn-1-yl, 3,3-dimethylbutyl, cyclobutyl, cyclopentyl, cyclohexyl -continued

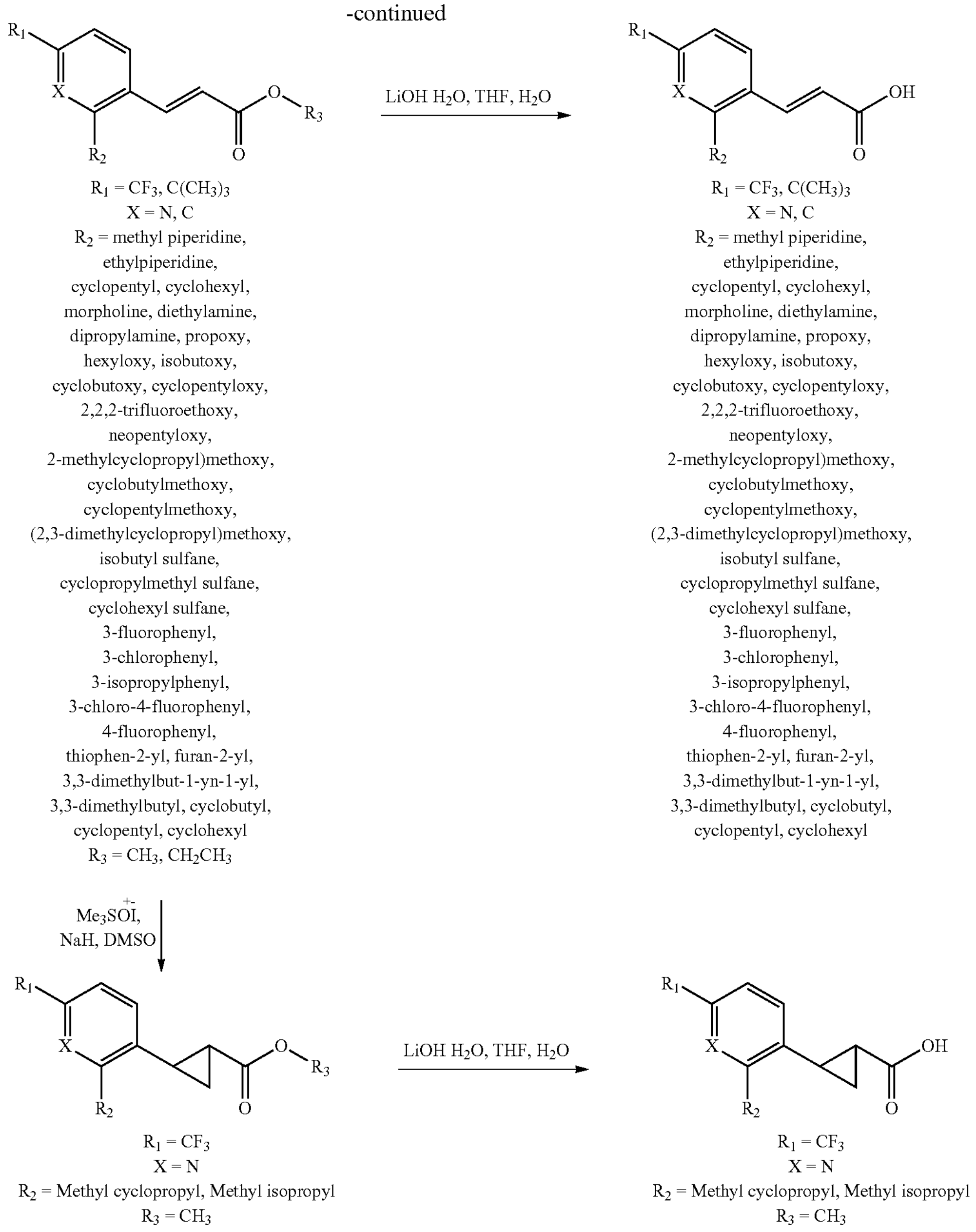

1-2-1. Synthesis of R2-Pyridine/Phenyl

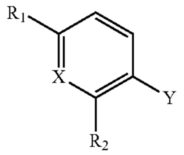

[Method 1A] NR/OR

As a starting material, pyridine or phenyl in which $R_1$ is $CF_3$ or $C(CH_3)_3$, Y is CN or Br, and Z is OH, Cl, F or SH was dissolved in THF or DMF, to which DBU (2 equivalents), NaH (2 equivalents) or $K_2CO_3$ (2 equivalents) was added at 0° C., followed by stirring for 5 to 10 minutes. The corresponding NR, OR, Halo-alkyl, and SR (2 equivalents) were dissolved in THF or DMF and added to the stirring mixture, followed by stirring at room temperature for 16 hours. The reaction was terminated by adding water, and the reactant was extracted with ethyl acetate or methylene chloride. The obtained organic layer was washed with brine, dried over magnesium sulfate, and then concentrated in vacuo. The obtained residue was purified by flash column chromatography filled with silica gel using a mixed solvent of ethyl acetate, hexane or methylene chloride and methyl alcohol as an elution solvent to give the target compound. (Yield: 85%-92%)

[Method 1B] C—C

As a starting material, 2-chloro-6-(trifluoromethyl)nicotinonitrile (2-chloro-6-(trifluoromethyl)nicotinonitrile) (1 equivalent) was dissolved in toluene and stirred, to which $Na_2CO_3$ (24 equivalents) dissolved in water was added, followed by stirring for 5 to 10 minutes. Then, $Pd(PPh_3)_4$ (0.2 equivalent) was added thereto. After the mixture was refluxed for 30 minutes or 3 hours, the reactor temperature was lowered to room temperature. The corresponding boronic acid (2 equivalents) was dissolved in toluene or 1,4-dioxane and added dropwise thereto, and the mixture was refluxed and stirred for hours. Upon completion of the reaction, the temperature of the reactor was lowered to room temperature, and the reactant was filtered with a celite pad filter and concentrated under reduced pressure. The resulting mixture was dissolved in ethyl acetate, washed with brine and water, dried over magnesium sulfate, and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 72%-85%)

[Method 1C] C—C

As a starting material, 2-chloro-6-(trifluoromethyl)nicotinonitrile (2-chloro-6-(trifluoromethyl)nicotinonitrile) (1 equivalent) was dissolved in toluene and stirred, to which the corresponding Alkyn (2 equivalents), $Pd(PPhA)_4$ (0.2 equivalent), Copper (I) Iodide (0.2 equivalent), and TEA (2 equivalents) were added, and the mixture was refluxed and stirred for 15 hours. Upon completion of the reaction, the temperature of the reactor was lowered to room temperature, and the reactant was filtered with a celite pad filter and concentrated under reduced pressure. The resulting mixture was dissolved in EtOAc, washed with brine and water, dried over magnesium sulfate, and concentrated in vacuo. The obtained residue was purified by flash column chromatography filled with silica gel using a mixed solvent of ethyl acetate and hexane as an elution solvent to give the target compound. (Yield: 65%-73%)

1-2-2. Synthesis of Pyridine/Phenyl Aldehyde

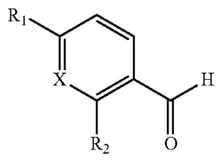

Pyridine/phenyl nitrile (1 equivalent) obtained in the above reaction was dissolved in toluene and filled with nitrogen, to which DIBAL-H (1M in toluene, 2 equivalents) was slowly added dropwise at −78° C., followed by stirring at the same temperature for 2 hours. The reaction was terminated by adding $NH_4Cl$ aqueous solution and the organic material was extracted with EtOAc. The resulting mixture was washed with brine and water, dried over magnesium sulfate, and concentrated in vacuo. The obtained residue was purified by flash column chromatography filled with silica gel using a mixed solvent of ethyl acetate and hexane as an elution solvent to give the target compound. (Yield: 61%-75%)

1-2-3. Synthesis of E-Methyl/Ethyl Acetate

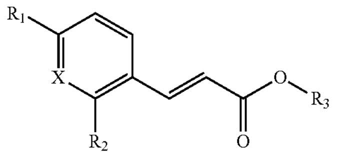

Method 2A

Aldehyde (1 equivalent) obtained in the above reaction was dissolved in toluene, to which methyl(triphenylphosphoranylidene)acetate) or ethyl(triphenylphosphoranylidene)acetate) (2 equivalents) was added, followed by stirring at room temperature for 24 hours. Upon completion of the reaction, toluene was removed by concentration under reduced pressure. The obtained residue was purified by flash column chromatography filled with silica gel using a mixed solvent of ethyl acetate and hexane as an elution solvent to give the target compound. (Yield: 50%-65%)

[Method 2B] Synthesis of methyl (E)-3-(2-(cyclopropylmethoxy)-6-(2-hydroxypropan-2-yl)pyridin-3-yl)acrylate

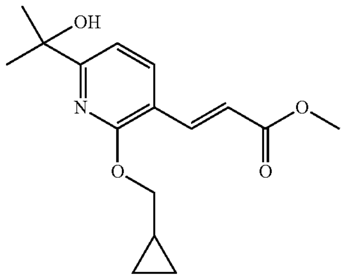 [SMILES: COC(=O)/C=C/c1ccc(C(C)(C)O)nc1OCC1CC1]

In the case of 2-(5-bromo-6-(cyclopropylmethoxy)pyridin-2-yl)propanl-2-ol having bromo in Y, 2-(5-bromo-6-(cyclopropylmethoxy)pyridin-2-yl)propan-2-ol (1 equivalent) was dissolved in anhydrous DMF, to which methyl acrylate (4 equivalents), $P(o\text{-}tol)_3$ (0.3 equivalent) and triethylamine (10 equivalents) were added, followed by bubbling with inert gas (nitrogen and argon) for at least 5 minutes. The reaction mixture was stirred at room temperature for 10 to 30 minutes. $Pd(OAc)_2$ (3 mol %) was added thereto, followed by bubbling with inert gas (nitrogen and argon) for 5 to 10 minutes. Then, the reaction mixture was stirred at 100° C. for 24 hours. Upon completion of the reaction, the temperature of the reactor was lowered to room temperature. The reactant was diluted with EtOAc, washed with water and brine, dried over magnesium sulfate, and concentrated in vacuo. The obtained residue was purified by flash column chromatography filled with silica gel using a mixed solvent of ethyl acetate and hexane as an elution solvent to give the target compound. (Yield: 65%)

1-2-4. Synthesis of trifluoromethyl pyridine cyclopropane-1-carboxylate

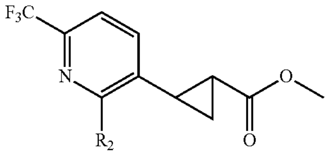

$R_2$ = Methyl cyclopropyl, Methyl isopropyl

Trimethyl sulfoxonium iodide (2 equivalents) was dissolved in DMSO, to which NaH (2 equivalents) was added at 0° C., followed by stirring at room temperature for 1 to 2 hours, preferably until a clear mixture was formed. The starting material pyridine acrylate (1 equivalent) obtained in the above reaction was dissolved in a small amount of DMSO, slowly added thereto dropwise, and the mixture was stirred at room temperature for 2 to 4 hours. The reaction was terminated by adding water, and the organic material was extracted with ethyl acetate. The reaction mixture was washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 80%-90%)

1-2-5. Synthesis of Pyridine/Phenyl Acrylic Acid And Cyclopropane Carboxylic Acid

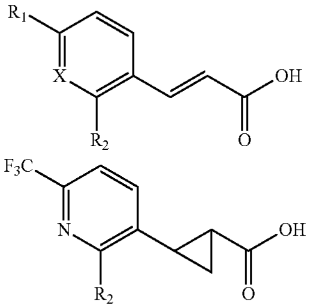

Pyridine or phenyl acrylate or pyridine cyclopropane carboxylate (1 equivalent) obtained in the above reaction was dissolved in THF, to which $LiOH \cdot H_2O$ (2 to 3 equivalents) and the same amount of water were added, followed by stirring at room temperature for 2 to 5 hours. Upon completion of the reaction, 1 N HCl was added at 0° C. to adjust the pH of the reactant to 2-3. The organic material was extracted with EtOAc, washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 85%-98%)

1-3. Synthesis of C-region starting material

[Reaction Formula 3]

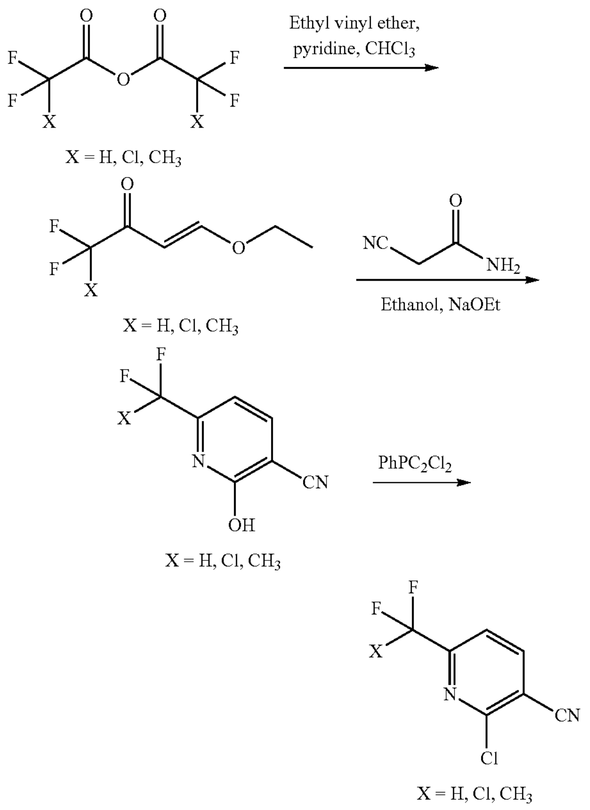

1-3-1. Synthesis of 2,2-difluoropropionic anhydride

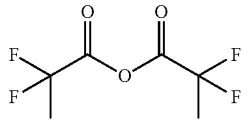

While stirring 2,2-difluoropropionic acid (1 equivalent) dissolved in methylene chloride at −10° C., oxanyl chloride (1.2 equivalents) was added dropwise thereto, followed by stirring at room temperature for 4 hours. Then, it was used as a starting material for the next reaction in a crude state.

1-3-2. Synthesis of 4-ethoxy difluorobutenone

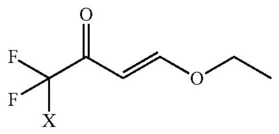

X = H, Cl, $CH_3$

As starting materials, 2,2-difluoropropionic anhydride obtained in the above reaction or the commercially available 2,2-dihyfluoroacetic anhydride and 2-chloro-2,2-difluoroacetic anhydride (1 equivalent) were dissolved in chloroform, and the temperature of the reactor was lowered to 0° C., followed by stirring. Ethyl vinyl ether (1.3 equivalents) and pyridine (1.3 equivalents) were added to the reaction mixture, followed by stirring at room temperature for 4 hours. The reaction was terminated by adding 1 N HCl, and the organic material was extracted with methylene chloride, washed with water and brine, and concentrated under reduced pressure at 30° C. The obtained residue was purified by flash column chromatography filled with silica gel using a mixed solvent of ethyl acetate and hexane as an elution solvent to give the target compound. (Yield: 89-95%)

1-3-3. Synthesis of 2-hydroxynicotinonitrile

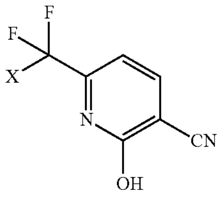

X = H, Cl, $CH_3$

2-Cyano acetamide (1 equivalent) was dissolved in ethanol, to which NaOEt 21% solution in ethanol (1.5 equivalents) was added dropwise, followed by stirring at room temperature for 10 to 20 minutes. After lowering the temperature of the reactor to 0° C., the starting material (1 equivalent) obtained in the above reaction was added dropwise to the reaction mixture. The reactor temperature was raised and the reaction mixture was reacted under reflux conditions for 5 hours. Upon completion of the reaction, the reactor temperature was lowered to room temperature, and the reactant was acidified with 4N HCl, extracted using EtOAc, and washed with water and brine. The resulting mixture was dried over magnesium sulfate and concentrated in vacuo. The obtained residue was purified by flash column chromatography filled with silica gel using a mixed solvent of ethyl acetate and hexane as an elution solvent to give the target compound. (Yield: 60%-75%)

1-3-4. Synthesis of 2-chloro-nicotinonitrile

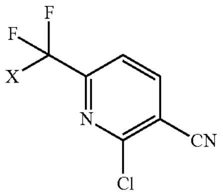

X = H, Cl, $CH_3$

The starting material (1 equivalent) obtained in the above reaction was dissolved in phenyl dichlorophosphate and stirred in a sealed tube at 170° C. for 3 hours. Upon completion of the reaction, the reactor temperature was lowered to room temperature, and the reactant was extracted with EtOAc or ether, and washed with water and brine. The resulting mixture was dried over magnesium sulfate and concentrated in vacuo. The obtained residue was purified by flash column chromatography filled with silica gel to give the target compound. (Yield: 71%-82%)

[Reaction Formula 4]

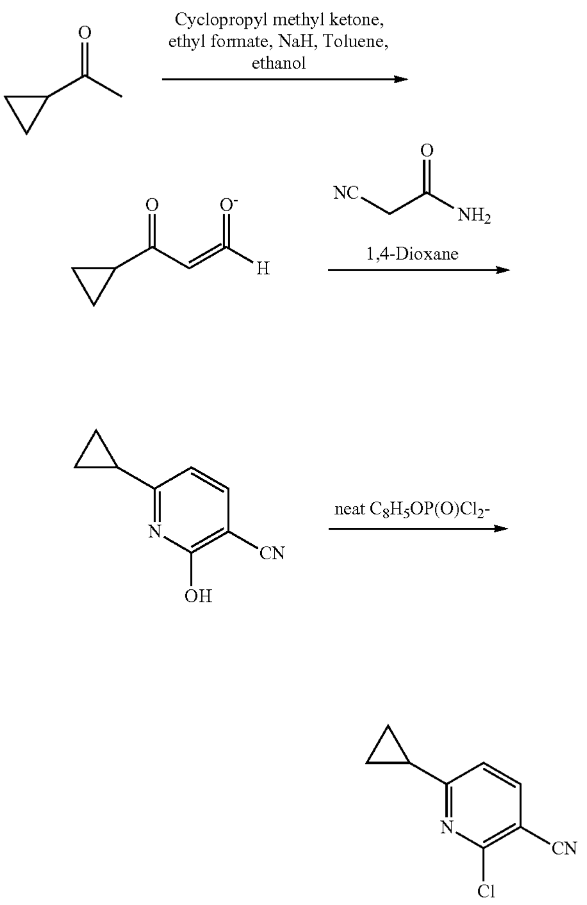

1-4-1. Synthesis of (Z)-3-cyclopropyl-3-oxoprop-1-en-1-olate

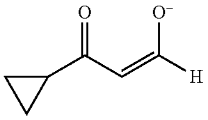

NaH (1 equivalent) was put into a reaction vessel, and nitrogen gas was charged, to which toluene and ethanol were added, followed by stirring. Cyclopropyl methyl ketone (1 equivalent) and Ethyl formate (1 equivalent) dissolved in toluene were added to the mixture, followed by reaction at room temperature for 15 hours. Upon completion of the reaction, an excess of toluene was added to the reactant, which was filtered and concentrated under reduced pressure to give the target product. (Yield: 81%)

1-4-2. Synthesis of 6-cyclopropyl-2-hydroxynicotinonitrile

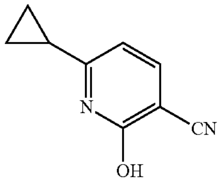 [SMILES: N#Cc1ccc(C2CC2)nc1O]

(Z)-3-cyclopropyl-3-oxoprop-1-en-1-olate (1 equivalent) obtained in the above reaction was dissolved in 1,4-dioxane, to which 2-cyano acetamide (1 equivalent) was added, followed by reflux reaction for 21 hours. Upon completion of the reaction, the temperature of the reactor was lowered to room temperature, and the reactant was filtered. AcOH was added to the obtained filtrate, followed by stirring for 10 to 30 minutes. Then, the reaction mixture was extracted with EtOAc, washed with water and brine, and the resulting mixture was dried over magnesium sulfate and concentrated in vacuo to give the target product. (Yield: 60%-70%)

1-4-3. Synthesis of 2-chloro-6-cyclopropylnicotinonitrile

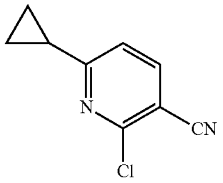 [SMILES: N#Cc1ccc(C2CC2)nc1Cl]

6-Cyclopropyl-2-hydroxynicotinonitrile (1 equivalent) obtained in the above reaction was dissolved in phenyl dichlorophosphate and stirred in a sealed tube at 170° C. for 3 hours. Upon completion of the reaction, the reactor temperature was lowered to room temperature, and the reactant was extracted with EtOAc or ether, and washed with water and brine. The resulting mixture was dried over magnesium sulfate and concentrated in vacuo. The obtained residue was purified by flash column chromatography filled with silica gel to give the target compound. (Yield: 71%-82%)

[Reaction Formula 5]

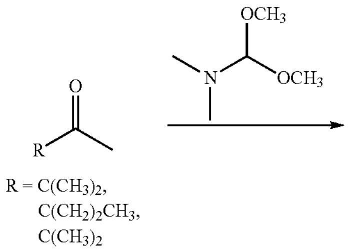

-continued

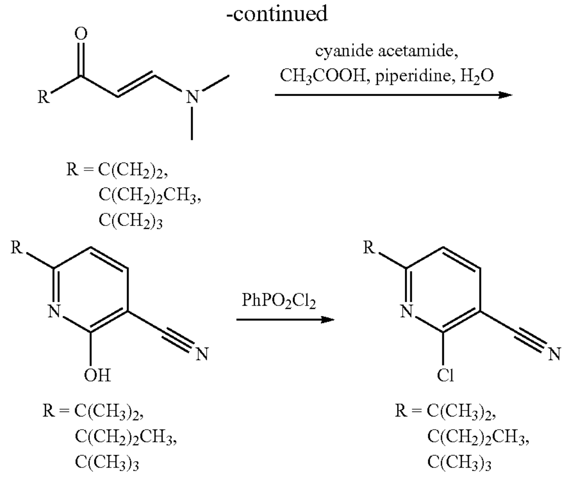

1-5-1. Synthesis of Dimethylamino Propen/Buten-1-One

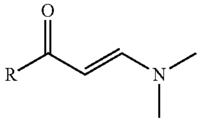

In a sealed tube, the starting material 3-methylbutan-2-one, or 1-(1-methylcyclopropyl)ethan-1-one, or 3,3-dimethylbutan-2-one was dissolved in excess dimethylformamide dimethyl acetal and stirred at 110° C. for 5 hours. Upon completion of the reaction, the reactor temperature was lowered to room temperature, and the organic layer was extracted with methylene chloride, and washed with water and brine. The resulting mixture was dried over magnesium sulfate and concentrated under reduced pressure at 30° C. The obtained residue was purified by flash column chromatography filled with silica gel to give the target compound. (Yield: 20%-50%)

1-5-2. Synthesis of 2-hydroxynicotinonitrile

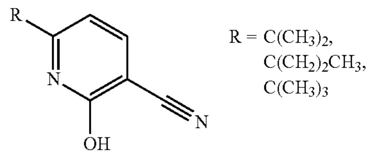

The starting material (1 equivalent) obtained in the above reaction and cyanide acetamide (1.3 equivalent) were added to a mixture of AcOH and piperidine (1:1.3), followed by stirring under reflux for 24 hours. Upon completion of the reaction, the reactor temperature was lowered to room temperature, and the reactant was acidified with 4N HCl, extracted using EtOAc, and washed with water and brine. The resulting mixture was dried over magnesium sulfate and concentrated in vacuo. The obtained residue was purified by flash column chromatography filled with silica gel using a mixed solvent of ethyl acetate and hexane as an elution solvent to give the target compound. (Yield: 60%-75%)

1-5-3. Synthesis of chloro-nicotinonitrile

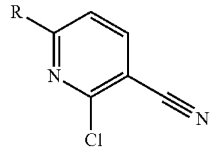

R = $C(CH_3)_2$,
$C(CH_2)_2CH_3$,
$C(CH_3)_3$

The starting material (1 equivalent) obtained in the above reaction was dissolved in phenyl dichlorophosphate and stirred in a sealed tube at 170° C. for 3 hours. Upon completion of the reaction, the reactor temperature was lowered to room temperature, and the reactant was extracted with EtOAc or ether, and washed with water and brine. The resulting mixture was dried over magnesium sulfate and concentrated in vacuo. The obtained residue was purified by flash column chromatography filled with silica gel to give the target compound. (Yield: 71%-82%)

[Reaction Formula 6]

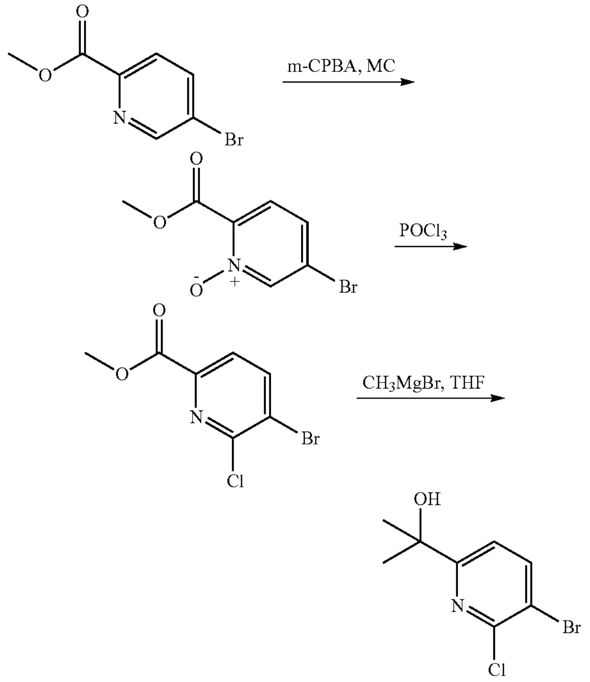

1-6-1. Synthesis of 5-bromo-2-(methoxycarbonyl)pyridine 1-oxide

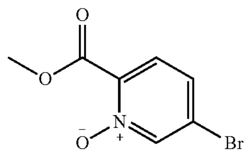

The starting material methyl 5-bromopicolinate (1.0 equivalent) was dissolved in methylene chloride, to which m-CPBA (2.0 equivalents) was added, followed by stirring under reflux conditions for 20 hours. The temperature of the reactor was cooled down to room temperature, and the reaction was terminated by adding $Na_2SO_3$ aqueous solution (saturated $Na_2SO_3$). The organic material was extracted with methylene chloride, and washed with water and brine. The resulting mixture was dried over magnesium sulfate and concentrated in vacuo. The obtained residue was purified by flash column chromatography filled with silica gel to give the target compound. (Yield: 76%-85%)

1-6-2. Synthesis of methyl 5-bromo-6-chloropicolinate

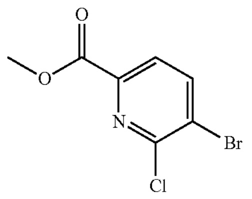

An excess of $POCl_3$ was added to 5-bromo-2-(methoxycarbonyl)pyridine 1-oxide) (1 equivalent) obtained in the above reaction at 0° C., and the mixture was stirred at 95° C. for 1 hour. The reaction was terminated by adding water. The organic material was extracted with EtOAc, and washed with water and brine. The resulting mixture was dried over magnesium sulfate and concentrated in vacuo. The obtained residue was purified by flash column chromatography filled with silica gel to give the target compound. (Yield: 68%-90%)

1-6-3. Synthesis of 2-(5-bromo-6-chloropyridin-2-yl)propan-2-ol

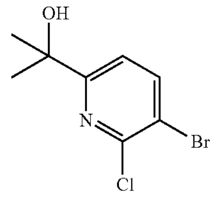

Methyl 5-Bromo-6-chloropicolinate (1 equivalent) obtained in the above reaction was dissolved in THF, to which 3 M $CH_3MgBr$ solution in diethyl ether (4.0 equivalents) was added dropwise at 0° C. in a nitrogen-filled reactor, followed by stirring at room temperature for 1 hour. The reaction was terminated by adding $NH_4Cl$ aqueous solution. The organic layer was extracted with EtOAc, and washed with water and brine. The resulting mixture was dried over magnesium sulfate and concentrated in vacuo to give the target compound. (Yield: 70%-85%)

[Reaction Formula 7]

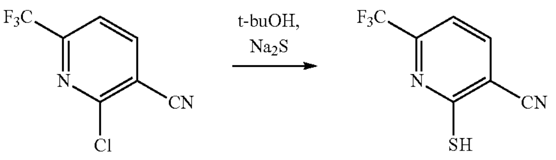

1-7-1. Synthesis of 2-mercapto-6-(trifluoromethyl)nicotinonitrile

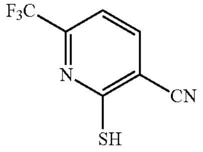

The starting material 2-chloro-6-(trifluoromethyl)nicotinonitrile (1 equivalent) was dissolved in t-butanol, to which $Na_2S$ (1 equivalent) was added, followed by stirring at 150° C. for 20 minutes in a microwave. The reaction was terminated by adding 1 N HCl. The organic layer was extracted with EtOAc, and washed with water and brine. The resulting mixture was dried over magnesium sulfate and concentrated in vacuo. The obtained residue was purified by flash column chromatography filled with silica gel to give the target compound. (Yield: 60%-65%)

[Reaction Formula 8] Synthesis of 4-cyclopropyl-fluorobenzonitrile

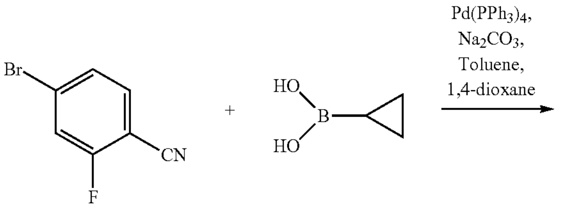

-continued

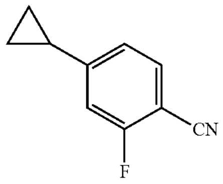

1-8-1. Synthesis of 4-cyclopropyl-2-fluorobenzonitrile

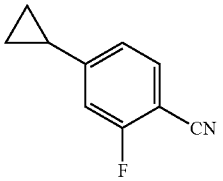 [SMILES: N#Cc1ccc(C2CC2)cc1F]

As a starting material, 4-bromo-2-fluorobenzonitrile (1 equivalent) was dissolved in toluene and stirred, to which $Na_2CO_3$ (24 equivalents) dissolved in water was added, followed by stirring for to 10 minutes. Then, $Pd(PPh_3)_4$ (0.2 equivalent) was added to the reaction mixture. After the mixture was stirred under reflux condition for 2 hours, the reactor temperature was lowered to room temperature, to which the corresponding boronic acid (2 equivalents) dissolved in 1,4-dioxane was added dropwise, followed by stirring under reflux condition for 15 hours. Upon completion of the reaction, the temperature of the reactor was lowered to room temperature, and the reactant was filtered with a celite pad filter and concentrated under reduced pressure. The resulting mixture was dissolved in ethyl acetate, washed with brine and water, dried over magnesium sulfate, and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 85%)

[Reaction Formula 9] Synthesis of pyrazole C-region
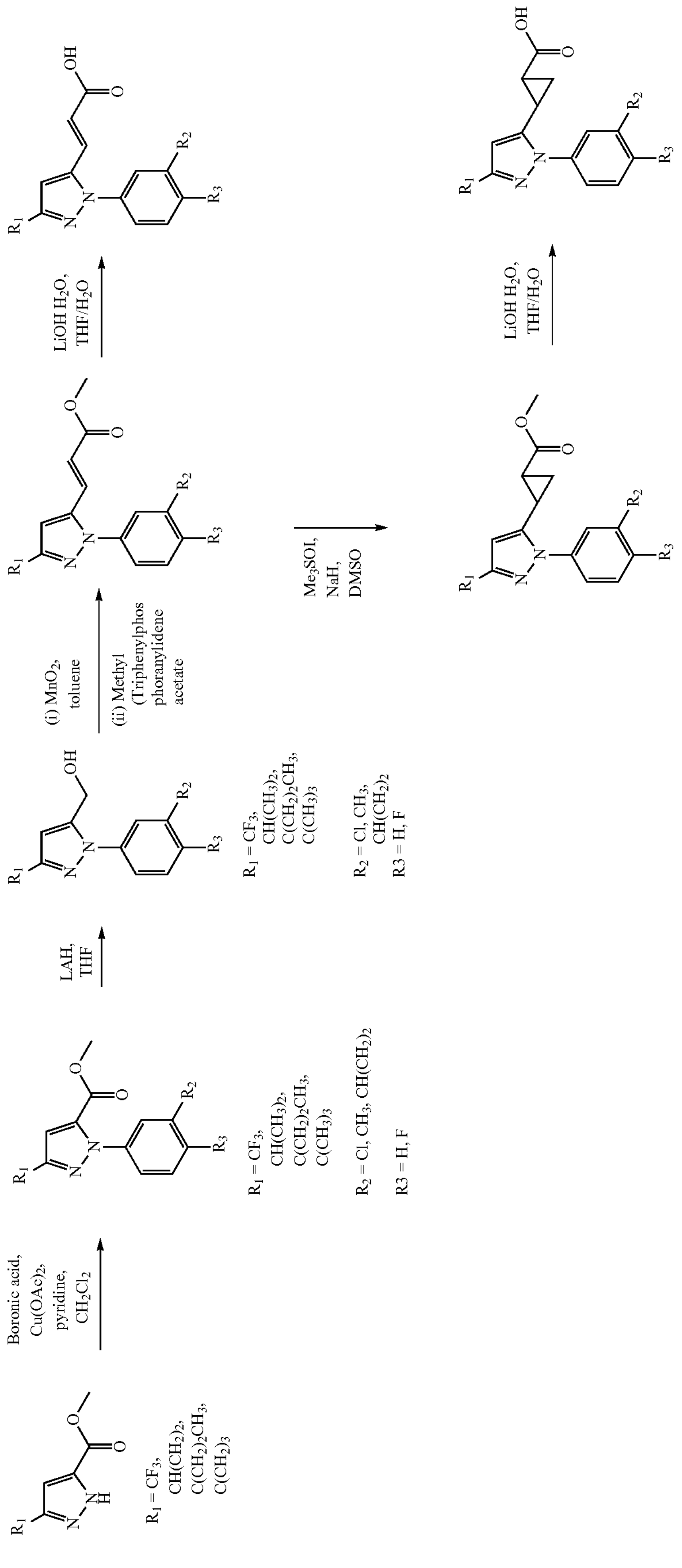

1-9-1. Synthesis of NR pyrazole-5-carboxylate

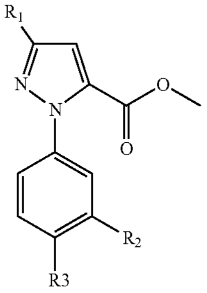

$R_1 = CF_3$, $CH(CH_3)_2$, $C(CH_2)_2CH_3$, $C(CH_3)_3$ $R_2 = Cl, CH_3, CH(CH_3)_2$

R3 = H, F

The starting material 1H-pyrazole-5-carboxylate (1 equivalent) synthesized in reaction formulas 10 to 11 was dissolved in methylene chloride and stirred, to which appropriate acid (2 equivalents), $Cu(OAc)_2$ (1.5 equivalent), and pyridine (2 equivalents) were added, followed by reaction at room temperature for 24 hours. Upon completion of the reaction, the reactant was filtered with a celite pad filter and the filtrate was concentrated under reduced pressure. The residue was purified by flash column chromatography filled with silica gel using a mixed solvent of ethyl acetate, hexane or methylene chloride and methyl alcohol as an elution solvent to give the target compound. (Yield: 80%-90%)

1-9-2. Synthesis of 1H-pyrazolyl Methanol

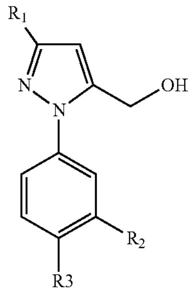

$R_1 = CF_3$, $CH(CH_3)_2$, $C(CH_2)_2CH_3$, $C(CH_3)_3$ $R_2 = Cl, CH_3$, $CH(CH_3)_2$

R3 = H, F

LAH (2 equivalents) was dissolved in THF in a reaction vessel and nitrogen was charged, to which the starting material (1 equivalent) obtained in the above reaction dissolved in THF was added dropwise at 0° C., followed by stirring at room temperature for 30 minutes to 1 hour. Upon completion of the reaction, the temperature of the reactor was lowered to 0° C., and the reaction was terminated by adding $NaHCO_3$ aqueous solution slowly. The reactant was filtered with a celite pad filter, and the filtrate was concentrated under reduced pressure. The residue was purified by flash column chromatography filled with silica gel using a mixed solvent of methylene chloride and methyl alcohol as an elution solvent to give the target compound. (Yield: 90%-98%)

1-9-3. Synthesis of 1H-pyrazolyl acrylate

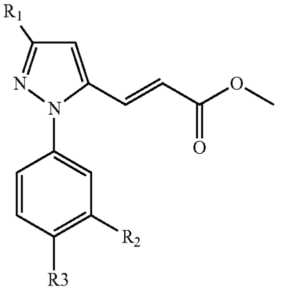

$R_1 = CF_3$, $CH(CH_3)_2$, $C(CH_2)_2CH_3$, $C(CH_3)_3$ $R_2 = Cl, CH_3$, $CH(CH_3)_2$

R3 = H, F

The starting material (1 equivalent) obtained by the above reaction was dissolved in toluene, to which $MnO_2$ (1 equivalent) was added, followed by stirring at room temperature for 30 minutes to 1 hour. Methyl(triphenylphosphoranylidene)acetate) (3.5 equivalents) was added to the mixture, followed by reaction under reflux conditions for 24 hours. Upon completion of the reaction, the reactant was filtered with a celite pad filter. The organic material was extracted with EtOAc, washed with brine and water, and the filtrate was dried over magnesium sulfate, and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 75%-90%)

1-9-4. Synthesis of 1H-pyrazolyl cyclopropane-1-carboxylate

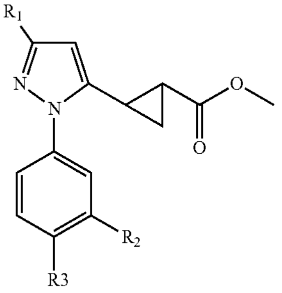

$R_1 = CF_3$, $CH(CH_3)_2$, $C(CH_2)_2CH_3$, $C(CH_3)_3$ $R_2 = Cl, CH_3$, $CH(CH_3)_2$

R3 = H, F

Trimethyl sulfoxonium iodide (2 equivalents) was dissolved in DMSO, to which NaH (2 equivalents) was added at 0° C., followed by stirring at room temperature for 1 to 2 hours, preferably until a clear mixture was formed. The starting material 1H-pyrazolyl acrylate (1 equivalent) obtained in the above reaction was dissolved in a small amount of DMSO and slowly added dropwise to the mixture, followed by stirring at room temperature for 2 to 4 hours. The reaction was terminated by adding water, and the organic material was extracted with ethyl acetate. The mixture was washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 80%-90%)

1-9-5. Synthesis of Carboxylic Acid

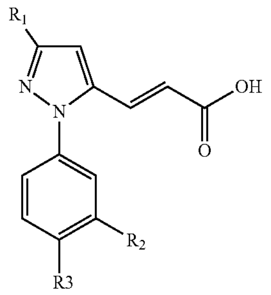

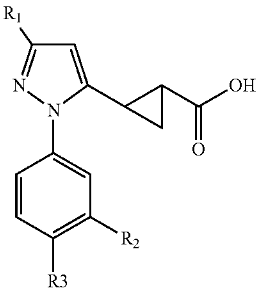

$R_1$ = $CF_3$, $CH(CH_3)_2$, $C(CH_2)_2CH_3$, $C(CH_3)_3$ $R_2$ = Cl, $CH_3$, $CH(CH_3)_2$
R3 = H, F

Acrylate or cyclocarboxylate (1 equivalent) obtained in the above reaction was dissolved in THF, to which $LiOH \cdot H_2O$ (2 to 3 equivalents) and the same amount of water were added, followed by stirring at room temperature for 2 to 5 hours. Upon completion of the reaction, 1 N HCl was added at 0° C. to adjust the pH of the reactant to 2-3. The organic material was extracted with ethyl acetate, washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 85%-98%)

[Reaction Formula 10] Synthesis of 1H-pyrazole-5-carboxylate

[Method A]

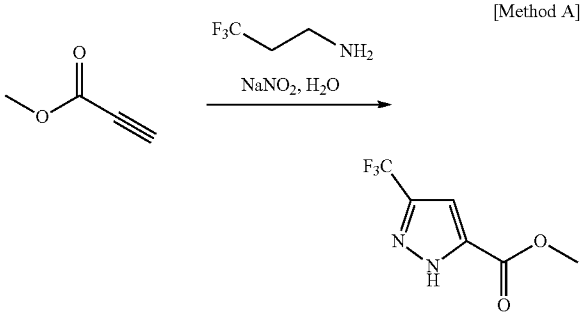

1-10-1. Synthesis of methyl 3-(trifluoromethyl)-1H-pyrazole-5-carboxylate

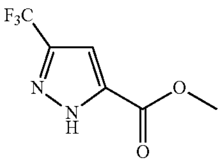

The starting material methylpropionate (1 equivalent) was dissolved in methylene chloride, to which $NaNO_2$ (3 equivalents) dissolved in water was slowly added dropwise, followed by stirring for 10 to 20 minutes. The reactor temperature was lowered to 0° C., and 3,3,3-trifluorophenylamine (3 equivalents) was added dropwise to the reaction mixture, followed by stirring at 0° C. for 1 to 2 hours. The reaction mixture was stirred at room temperature for 30 minutes, and the reaction was terminated by adding water. The organic material was extracted with methylene chloride, washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 65%-88%)

[Method B]

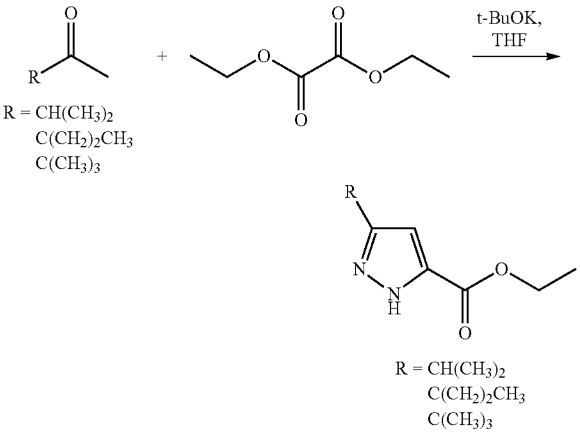

1-10-2. Synthesis of 1H-pyrazole-5-carboxylate

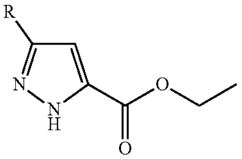

R = $CH(CH_3)_2$
$C(CH_2)_2CH_3$
$C(CH_3)_3$

Methyl-1-methylcyclopropylketone, isopropyl methyl ketone or pinacolone (1 equivalent) was added to a mixture in which t-BuOK (1.5 equivalent) was dissolved in THF at 0° C., to which diethyloxalate (1 equivalent) dissolved in THF was added dropwise, followed by stirring at room temperature for 15 hours. AcOH (0.15 ml/mmol) was added to the mixture and hydrazine monohydrate (1.1 equivalent) was added dropwise thereto, followed by stirring under reflux condition for 3 hours. Upon completion of the reaction, the reactant was concentrated under reduced pressure, water was added to the obtained solid, followed by stirring for 3 to 6 hours. The obtained solid was filtered under reduced pressure and dried to give the target product. (Yield: 80%-91%)

[Reaction Formula 11] Synthesis of thiazole C-region

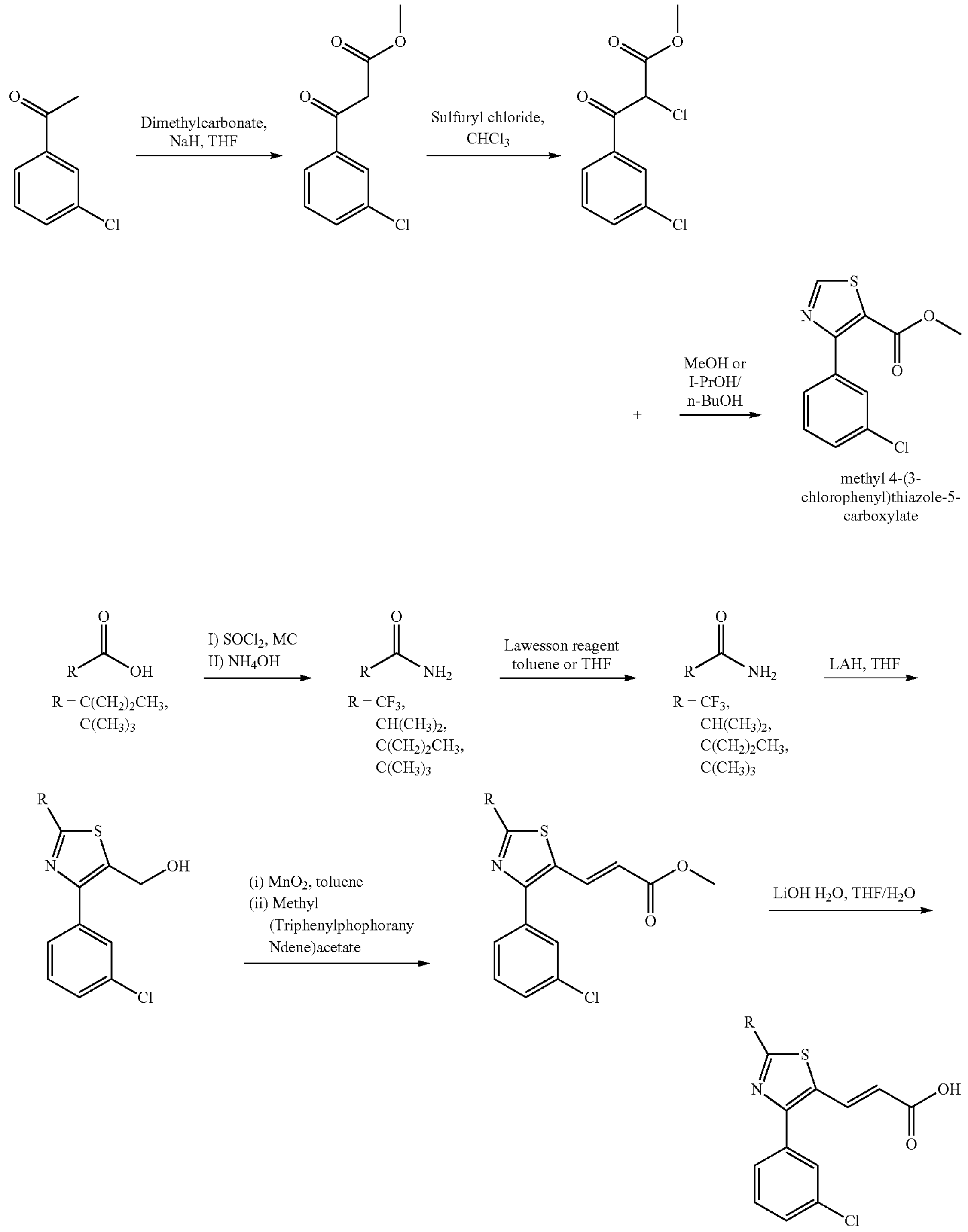

methyl 4-(3-chlorophenyl)thiazole-5-carboxylate 1-11-1. Synthesis of methyl 3-(3-chlorophenyl)-3-oxopropanoate

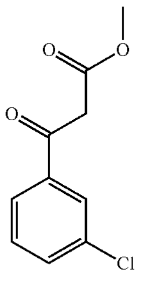

NaH (3 equivalents) was dissolved in THF by stirring in a reaction vessel filled with nitrogen. The reactor temperature was lowered to 0° C., and the starting material 1-(3-chlorophenyl)ethan-1-one (1 equivalent) and dimethyl carbonate (3 equivalents) were slowly added dropwise, followed by stirring at room temperature for 10 to 30 minutes. The reactor temperature was raised to 50° C., and the reactant was stirred for 15 hours. The reaction was terminated by adding 1 N HCl at 0° C. The organic material was extracted with ethyl acetate, washed with water and brine, and the resulting filtrate was dried over magnesium sulfate and concentrated in vacuo. The obtained residue was purified by flash column chromatography filled with silica gel using a mixed solvent of ethyl acetate and hexane as an elution solvent to give the target compound. (Yield: 65%-88%)

1-11-2. Synthesis of methyl 2-chloro-3-(3-chlorophenyl)-3-oxopropanoate

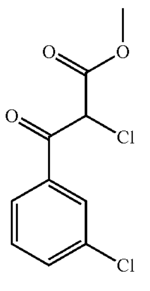

After dissolving methyl 3-(3-chlorophenyl)-3-oxopropanoate (1 equivalent) obtained in the above reaction in chloroform, the reactor was filled with nitrogen, to which sulfuryl chloride (1.1 equivalent) was added dropwise at 0° C., followed by stirring under reflux condition for 15 hours. Upon completion of the reaction, the reaction mixture was concentrated under reduced pressure. The obtained residue was purified by flash column chromatography filled with silica gel using a mixed solvent of ethyl acetate and hexane as an elution solvent to give the target compound. (Yield: 75%-88%)

1-11-3. Synthesis of R-carboxamide

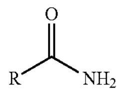

R = $C(CH_2)_2CH_3$, $C(CH_3)_3$

1-Methylcyclopropane-1-carboxylic acid or pivalic acid (1 equivalent) was dissolved in toluene in a reaction vessel filled with nitrogen, to which thionylchloride (1.1 equivalent) was added dropwise at 0° C., followed by stirring at room temperature for 5 hours. An excess of $NH_4OH$ aqueous solution was slowly added dropwise thereto at sub-zero temperature, followed by stirring at room temperature for 15 hours. The reaction was terminated by adding water. The organic material was extracted with EtOAc, washed with water and brine, and the resulting filtrate was dried over magnesium sulfate and concentrated in vacuo to give the target compound. (Yield: 71%-89%)

1-11-4. Synthesis of R-carbothioamide

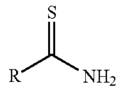

R = $CF_3$, $CH(CH_3)_2$, $C(CH_2)_2CH_3$, $C(CH_3)_3$

Using 1-methylcyclopropane-1-carboxamide and pivalamide obtained in the above reaction or commercially available isobutyramide and 2,2,2-trifluoroacetamide as starting materials, they were dissolved in THF or toluene, to which Lawesson's reagent (0.6 equivalent) was added, followed by stirring at room temperature for 15 to 30 minutes. Then, the reaction mixture was stirred under reflux condition for 2 hours preferably 4 hours. Upon completion of the reaction, the reaction mixture was concentrated under reduced pressure. The obtained residue was purified by flash column chromatography filled with silica gel using a mixed solvent of methylene chloride and methanol as an elution solvent to give the target compound. (Yield: 45%-68%)

1-11-5. Synthesis of thiazole-5-carboxylate

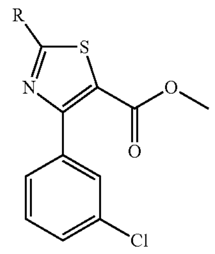

Methyl 2-chloro-3-(3-chlorophenyl)-3-oxopropanoate (1 equivalent) obtained in the above reaction was dissolved in MeOH or a mixed solution of i-PrOH:n-BuOH (1:1), to which carbothioamide (1.32 equivalent) obtained in 1-11-4 dissolved in the same solvent was added dropwise, followed by stirring at room temperature for 10 to 30 minutes. Then, the reaction mixture was stirred under reflux condition for 15 hours. The reaction was terminated by adding water. The organic material was extracted with ethyl acetate. The organic material was extracted with ethyl acetate, washed with water and brine, and the resulting filtrate was dried over magnesium sulfate and concentrated in vacuo. The obtained residue was purified by flash column chromatography filled with silica gel using a mixed solvent of ethyl acetate and hexane as an elution solvent to give the target compound. (Yield: 65%-88%)

1-11-6. Synthesis of R-(3-chlorophenyl)thiazol-5-yl methanol

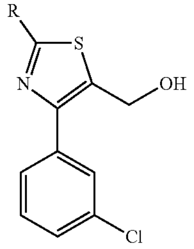

LAH (2 equivalents) was dissolved in THF in a reaction vessel and nitrogen was charged, to which the starting material thiazole-5-carboxylate (1 equivalent) obtained in the above reaction dissolved in THF was added dropwise at 0° C., followed by stirring at room temperature for 30 minutes to 1 hour. The temperature of the reactor was lowered to 0° C., and the reaction was terminated by adding $NaHCO_3$ aqueous solution slowly. The reactant was filtered with a celite pad filter and the resulting filtrate was concentrated under reduced pressure. The obtained residue was purified by flash column chromatography filled with silica gel using a mixed solvent of methylene chloride and methyl alcohol as an elution solvent to give the target compound. (Yield: 90%-98%)

1-11-7. Synthesis of R-(3-chlorophenyl)thiazol-5-yl)methyl acrylate

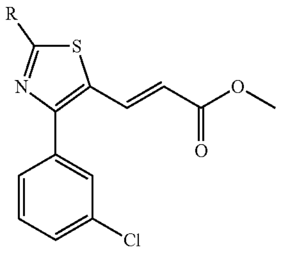

The starting material (1 equivalent) obtained in 1-11-6 was dissolved in toluene, to which $MnO_2$ (1 equivalent) was added, followed by stirring at room temperature for 30 minutes to 1 hour. Methyl(triphenylphosphoranylidene)acetate) or ethyl(triphenylphosphoranylidene)acetate) (3.5 equivalents) was added to the mixture, followed by stirring under reflux condition for 24 hours. Upon completion of the reaction, the reactant was filtered with a celite pad filter and the organic material was extracted with ethyl acetate, washed with water and brine. The resulting filtrate was dried over magnesium sulfate, and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 75%-90%)

1-11-8. Synthesis of (E)-R-(3-chlorophenyl)thiazolyl-acrylic acid

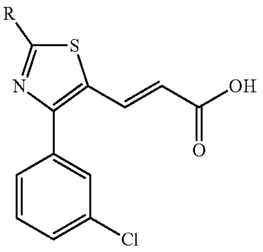

Acrylate (1 equivalent) obtained in 11-7 was dissolved in THF, to which $LiOH \cdot H_2O$ (2 to 3 equivalents) and the same amount of water were added, followed by stirring at room temperature for 2 to 5 hours. Upon completion of the reaction, 1 N HCl was added at 0° C. to adjust the pH of the reactant to 2-3. The organic material was extracted with EtOAc, washed with water and brine, and the resulting filtrate was dried over magnesium sulfate and concentrated in vacuo. The obtained residue was purified by flash column chromatography filled with silica gel using a mixed solvent of ethyl acetate, hexane or methylene chloride and methyl alcohol as an elution solvent to give the target compound. (Yield: 85%-98%)

1-3. Synthesis of B-Region

[Reaction Formula 12] EDC coupling

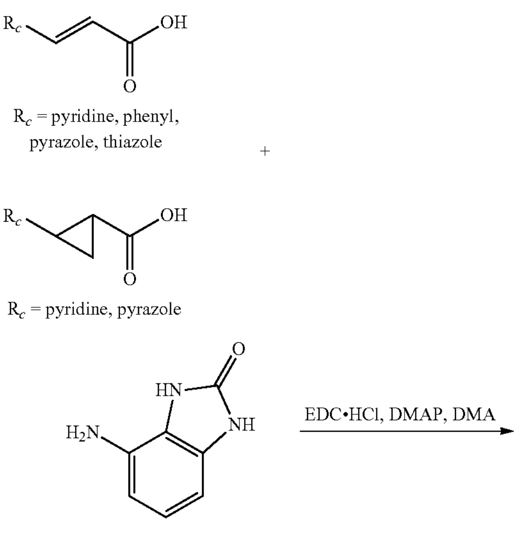

-continued

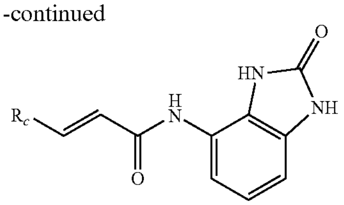

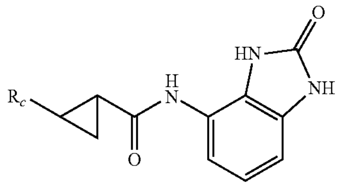

1-12-1. EDC Coupling

Acrylic acid or cyclopropane-1-carboxylic acid obtained in the above reaction was dissolved in DMA, to which EDC·HCl (1.5 equivalent) and DMAP (1.5 equivalent) were added, followed by stirring at room temperature for 10 to 20 minutes. After adding 4-amino-benzo[d]imidazol-2-one (4-amino-benzo[d]imidazol-2-one) derivative (2 equivalents) obtained in reaction formulas 1A and 1B, the mixture was stirred at room temperature for 3 hours to preferably 5 hours. The reaction was terminated by adding water. The organic layer was extracted with ethyl acetate or methylene chloride, and concentrated under reduced pressure. The obtained residue was purified by column chromatography to give the target compound. (Yield: 60-88%)

[Reaction Formula 13]

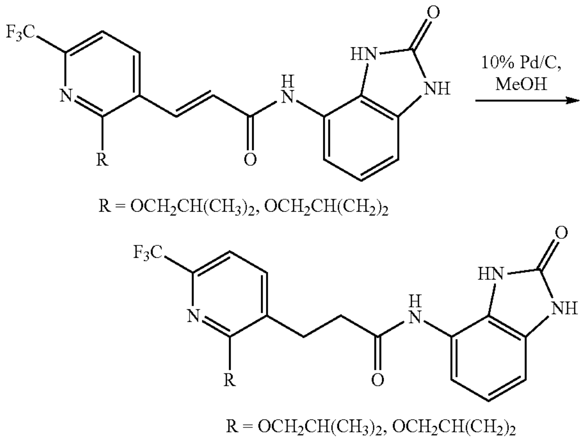

1-13-1. Synthesis of 6-(trifluoromethyl)pyridin-3-yl)-N-(2-oxo-2,3-dihydro-1H-benzo[d]imidazol-4-yl)propaneamide(6-(trifluoromethyl)pyridin-3-yl)-N-(2-oxo-2,3-dihydro-1H-benzo[d]imidazol-4-yl) propanamide)

(E)-3-(2-isobutoxy-6-(trifluoromethyl)pyridin-3-yl)-N-(2-oxo-2,3-dihydro-1H-benzo[d]imidazol-4-yl)acrylamide ((E)-3-(2-isobutoxy-6-(trifluoromethyl)pyridin-3-yl)-N-(2-oxo-2,3-dihydro-1H-benzo[d]imidazol-4-yl)acrylamide) or (E)-3-(2-(cyclopropylmethoxy)-6-(trifluoromethyl)pyridin-3-yl)-N-(2-oxo-2,3-dihydro-1H-benzo[d]imidazol-4-yl) acrylamide((E)-3-(2-(cyclopropylmethoxy)-6-(trifluoromethyl)pyridin-3-yl)-N-(2-oxo-2,3-dihydro-1H-benzo[d] imidazol-4-yl)acrylamide) (1 equivalent) obtained in 1-12-1 was hydrogenated with a reducing agent such as 10% palladium-activated carbon (Pd—C) dissolved in lower alcohol such as methanol, filtered with celite pad, and the filtrate was dried under reduced pressure. The reactant was purified by flash column chromatography filled with silica gel using a mixed solvent of methylene chloride and methyl alcohol as an elution solvent to give the target compound. (Yield: 90%-98%)

The compounds of Examples 1 to 68 were synthesized through reaction formulas 1 to 13, and NMR data of each example compound are as follows.

Representatively, the compound of <Example 1> was prepared by using a compound in which $R_1$ is $CF_3$, X is N, and $R_2$ is methyl piperidine in [Reaction Formula 2] as a starting material in [Reaction Formula 12], and reacting with A-region.

<Example 1> (E)-3-(2-(4-methylpiperidin-1-yl)-6-(trifluoromethyl)pyridin-3-yl)-N-(2-oxo-2,3-dihydro-1H-benzo[d]imidazol-4-yl)acrylamide

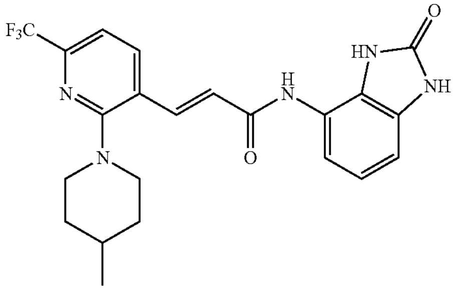 [SMILES: CC1CCN(c2nc(C(F)(F)F)ccc2/C=C/C(=O)Nc2cccc3[nH]c(=O)[nH]c23)CC1]

Yellow solid, yield 72%; $^1H$ NMR (500 MHz, DMSO) δ 10.72 (s, 1H), 10.15 (s, 1H), 9.96 (s, 1H), 8.05 (d, J=7.65 Hz, 1H). 7.70 (m, 1H), 7.59 (d, J=10.20 Hz, 1H), 7.42 (d, J=7.75 Hz, 1H), 7.24 (d, J=8.05 Hz, 1H), 6.93 (t, J=7.90 Hz, 1H), 6.86 (d, J=15.70 Hz, 1H), 6.78 (d, J=7.70 Hz, 1H), 4.20 (m, 1H), 3.63 (d, J=12.55 Hz, 2H), 2.86 (t, J=12.15 Hz, 2H), 1.96 (m, 1H), 1.72 (d, J=11.45 Hz, 2H), 1.58 (m, 1H), 1.31-1.26 (m, 2H), 1.25 (s, 4H), 0.95 (d, J=6.45 Hz, 3H); Mass (FAB) m/z 446 $[M+H]^+$ <Example 2> (E)-3-(2-(4-ethylpiperidin-1-yl)-6-(trifluoromethyl)pyridin-3-yl)-N-(2-oxo-2,3-dihydro-1H-benzo[d]imidazol-4-yl)acrylamide

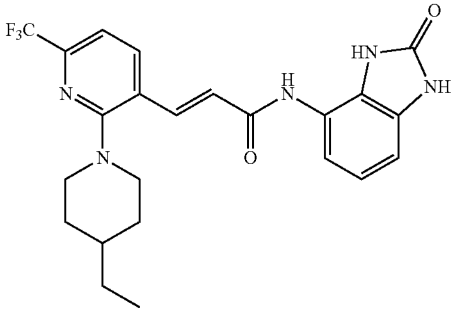 [SMILES: CCC1CCN(c2nc(C(F)(F)F)ccc2/C=C/C(=O)Nc2cccc3[nH]c(=O)[nH]c23)CC1]

White solid, Yield 88%; 1H-NMR (400 MHz, DMSO) δ 10.69 (s, 1H), 10.09 (s, 1H), 9.88 (s, 1H), 8.01 (d, J=7.6 Hz, 1H), 7.51 (d, J=15.6 Hz, 1H), 7.39 (d, J=8.0 Hz, 1H), 7.20 (d, J=8.4 Hz, 1H), 6.89 (t, J=8.0 Hz, 1H), 6.81 (d, J=15.6 Hz, 1H), 6.74 (d, J=7.2 Hz, 1H), 3.62 (d, J=14.2 Hz, 2H), 2.81 (t, J=11.6 Hz, 2H), 1.74 (d, J=10.4 Hz, 2H), 1.27-1.19 (m, 4H), 1.15-1.13 (t, J=7.6 Hz, 1H), 0.84 (m, 3H); Mass (FAB) m/z 460 $[M+H]^+$ <Example 3> (E)-N-(2-oxo-2,3-dihydro-1H-benzo[d]imidazol-4-yl)-3-(2-(pyrrolidin-1-yl)-6-(trifluoromethyl)pyridin-3-yl)acrylamide

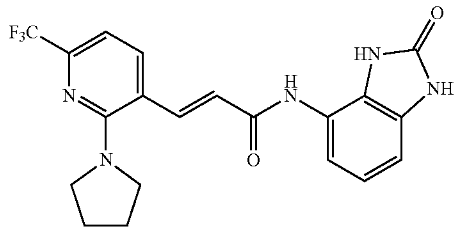 [SMILES: O=C(/C=C/c1ccc(C(F)(F)F)nc1N1CCCC1)Nc1cccc2[nH]c(=O)[nH]c12]

White solid, yield 65%; $^1$H-NMR (400 MHz, DMSO) δ 10.67 (s, 1H), 10.08 (s, 1H), 9.08 (s, 1H), 7.83 (d, J=7.2 Hz, 1H), 7.78 (d, J=15.6 Hz, 1H), 7.20 (d, J=8.0 Hz, 1H), 7.11 (d, J=8.0 Hz, 1H), 6.88 (t, J=8.0 Hz, 1H), 6.72 (d, J=7.6 Hz, 1H), 6.50 (d, J=15.2 Hz, 1H), 3.49 (m, 4H), 1.85 (m, 4H); Mass (FAB) m/z 418 $[M+H]^+$ <Example 4> (E)-N-(2-oxo-2,3-dihydro-1H-benzo[d]imidazol-4-yl)-3-(2-(piperidin-1-yl)-6-(trifluoromethyl)pyridin-3-yl)acrylamide

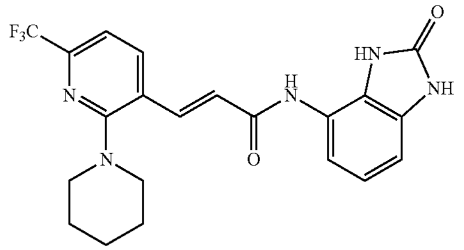 [SMILES: O=C(/C=C/c1ccc(C(F)(F)F)nc1N1CCCCC1)Nc1cccc2[nH]c(=O)[nH]c12]

Yellow solid, yield 61%; $^1$H NMR (300 MHz, DMSO) δ 10.73 (s, 1H), 10.14 (s, 1H), 9.92 (s, 1H), 8.06 (d, J=7.71 Hz, 1H), 7.56 (d, J=15.39 Hz, 1H), 7.44 (d, J=7.68 Hz, 1H), 7.23 (d, J=7.89 Hz, 1H), 6.95-6.84 (m, 2H), 6.77 (d, J=7.86 Hz, 1H), 3.24 (m, 4H), 1.66 (m, 8H); Mass (ESI) m/z 432 $[M+H]^+$ <Example 5> (E)-3-(2-morpholino-6-(trifluoromethyl)pyridin-3-yl)-N-(2-oxo-2,3-dihydro-1H-benzo[d]imidazol-4-yl)acrylamide

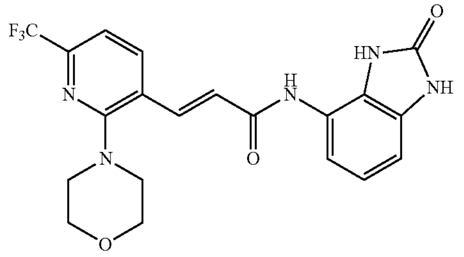 [SMILES: O=C(/C=C/c1ccc(C(F)(F)F)nc1N1CCOCC1)Nc1cccc2[nH]c(=O)[nH]c12]

Yellow solid, yield 82%; $^1$H NMR (300 MHz, CD3OD) δ 8.06 (d, J=7.9 Hz, 1H), 7.84 (d, J=15.8 Hz, 1H), 7.38 (d, J=7.9 Hz, 1H), 7.05 (s, 1H), 7.04 (d, J=2.4 Hz, 1H), 6.93-6.87 (m, 2H), 3.86 (m, 4H), 3.33 (m, 4H); Mass (ESI) m/z 434 $[M+H]^+$ <Example 6> (E)-3-(2-(diethylamino)-6-(trifluoromethyl)pyridin-3-yl)-N-(2-oxo-2,3-dihydro-1H-benzo[d]imidazol-4-yl)acrylamide

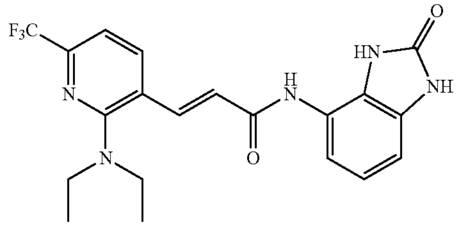 [SMILES: CCN(CC)c1nc(C(F)(F)F)ccc1/C=C/C(=O)Nc1cccc2[nH]c(=O)[nH]c12]

Yellow solid, yield 80%; $^1$H NMR (500 MHz, DMSO) δ 10.72 (s, 1H), 10.12 (s, 1H), 9.90 (s, 1H), 7.99 (d, J=7.60 Hz, 1H), 7.59 (d, J=15.55 Hz, 1H), 7.33 (d, J=7.75 Hz, 1H), 7.25 (d, J=8.10 Hz, 1H), 6.92 (t, J=7.95 Hz, 1H), 6.78 (d, J=11.76 Hz, 1H), 6.76 (s, 1H), 2.94 (m, 4H) 1.14 (t, J=6.90 Hz, 6H); Mass (FAB) m/z 420 $[M+H]^+$ <Example 7> (E)-3-(2-(dipropylamino)-6-(trifluoromethyl)pyridin-3-yl)-N-(2-oxo-2,3-dihydro-1H-benzo[d]imidazol-4-yl)acrylamide

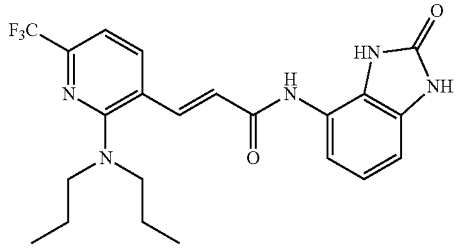 [SMILES: CCCN(CCC)c1nc(C(F)(F)F)ccc1/C=C/C(=O)Nc1cccc2[nH]c(=O)[nH]c12]

Yellow solid, yield 82%; $^1$H NMR (500 MHz, DMSO) δ 10.72 (s, 1H), 10.10 (s, 1H), 9.91 (s, 1H), 7.97 (d, J=7.60 Hz, 1H), 7.59 (d, J=15.55 Hz, 1H), 7.31 (d, J=7.70 Hz, 1H), 7.25 (d, J=8.10 Hz, 1H), 6.93 (t, J=7.90 Hz, 1H), 6.75-6.78 (dd, J=3.35 Hz, 7.95 Hz, 2H), 3.28 (t, J=7.50 Hz, 4H), 1.60 (q, J=7.25 Hz, 4H), 0.81 (t, J=7.35 Hz, 6H); Mass (FAB) m/z 448 [M+H]$^+$ <Example 8> (E)-3-(2-butoxy-6-(trifluoromethyl)pyridin-3-yl)-N-(2-oxo-2,3-dihydro-1H-benzo[d]imidazol-4-yl)acrylamide

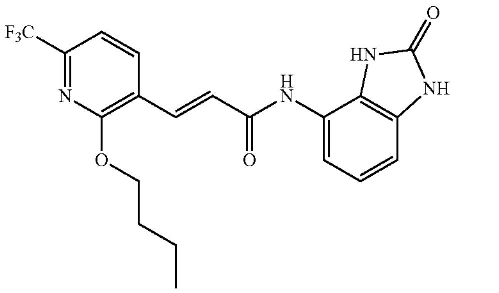 [SMILES: CCCCOc1nc(C(F)(F)F)ccc1/C=C/C(=O)Nc1cccc2[nH]c(=O)[nH]c12]

White solid, yield 63%; $^1$H-NMR (300 MHz, DMSO) δ 10.71 (s, 1H), 10.15 (s, 1H), 9.95 (s, 1H), 8.24 (d, J=7.5 Hz, 1H), 7.71 (d, J=15.8 Hz, 1H), 7.57 (d, J=7.9 Hz, 1H), 7.20 (d, J=8.2 Hz, 1H), 7.05 (d, J=15.8 Hz, 1H), 6.93 (t, J=7.5 Hz, 1H), 6.78 (d, J=7.7 Hz, 1H), 4.44 (t, J=6.6 Hz, 2H), 1.81 (m, 2H), 1.46 (m, 2H), 0.96 (t, J=7.32 Hz, 3H); Mass (FAB) m/z 421 [M+H]$^+$ <Example 9> (E)-3-(2-(hexyloxy)-6-(trifluoromethyl)pyridin-3-yl)-N-(2-oxo-2,3-dihydro-1H-benzo[d]imidazol-4-yl)acrylamide

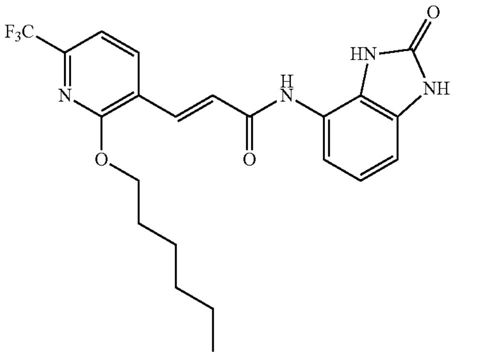 [SMILES: CCCCCCOc1nc(C(F)(F)F)ccc1/C=C/C(=O)Nc1cccc2[nH]c(=O)[nH]c12]

White solid, yield 73%; $^1$H NMR (300 MHz, DMSO) δ 10.71 (s, 1H), 10.15 (s, 1H), 9.95 (s, 1H), 8.24 (d, J=7.71 Hz, 1H), 7.70 (d, J=15.75 Hz, 1H), 7.56 (d, J=7.68 Hz, 1H), 7.21 (d, J=8.25 Hz, 1H), 7.05 (d, J=15.75 Hz, 1H), 6.93 (t, 1H), 6.77 (d, J=7.89 Hz, 1H), 4.43 (t, J=6.57 Hz, 2H), 1.82 (m, 2H), 1.43-1.23 (m, 7H), 0.88-0.86 (m, 3H); Mass (FAB) m/z 449 [M+H]$^+$ <Example 10> (E)-3-(2-isobutoxy-6-(trifluoromethyl)pyridin-3-yl)-N-(2-oxo-2,3-dihydro-1H-benzo[d]imidazol-4-yl)acrylamide

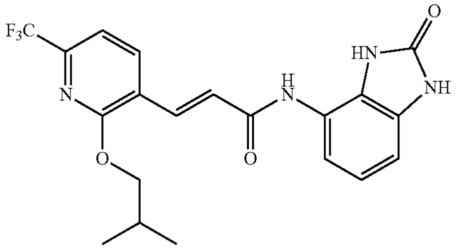 [SMILES: CC(C)COc1nc(C(F)(F)F)ccc1/C=C/C(=O)Nc1cccc2[nH]c(=O)[nH]c12]

White solid, yield 73%; $^1$H NMR (300 MHz, DMSO) δ 10.72 (s, 1H), 10.16 (s, 1H), 7.95 (s, 1H), 8.25 (d, J=7.71 Hz, 1H), 7.74 (d, J=15.75 Hz, 1H), 7.57 (d, J=7.69 Hz, 1H), 7.19 (d, J=7.71 Hz, 1H), 7.04 (d, J=15.72 Hz, 1H), 6.93 (t, J=8.04 Hz, 1H), 6.78 (d, J=7.68 Hz, 1H), 4.21 (d, J=6.78 Hz, 1H), 2.17 (p, J=6.57 Hz, 1H), 1.02 (d, J=6.78 Hz, 6H); Mass (ESI) m/z 421 [M+H]$^+$ <Example 11> (E)-3-(2-cyclobutoxy-6-(trifluoromethyl)pyridin-3-yl)-N-(2-oxo-2,3-dihydro-1H-benzo[d]imidazol-4-yl)acrylamide

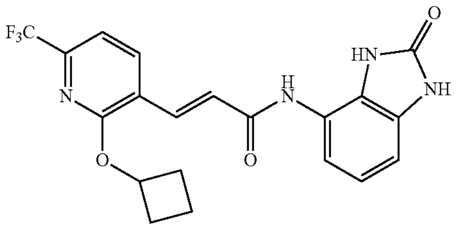 [SMILES: O=C(/C=C/c1ccc(C(F)(F)F)nc1OC1CCC1)Nc1cccc2[nH]c(=O)[nH]c12]

White solid, yield 82%; $^1$H-NMR (300 MHz, DMSO) δ 10.71 (s, 1H), 10.14 (s, 1H), 9.98 (s, 1H), 8.23 (d, J=7.7 Hz, 1H), 7.68 (d, J=15.6 Hz, 1H), 7.56 (d, J=7.5 Hz, 1H), 7.18 (d, J=7.9 Hz, 1H), 7.09 (d, J=7.5 Hz, 1H), 6.93 (t, J=7.9 Hz, 1H), 6.78 (d, J=7.9 Hz, 1H), 5.26 (m, 1H), 2.50 (m, 2H), 2.22 (m, 2H), 1.78 (m, 2H); Mass (ESI) m/z 419 [M+H]$^+$ <Example 12> (E)-3-(2-(cyclopentyloxy)-6-(trifluoromethyl)pyridin-3-yl)-N-(2-oxo-2,3-dihydro-1H-benzo[d]imidazol-4-yl)acrylamide

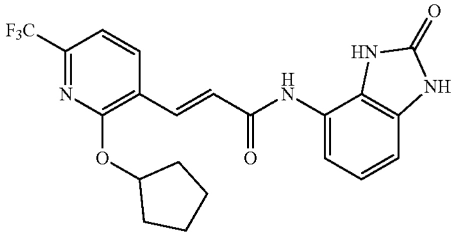 [SMILES: O=C(/C=C/c1ccc(C(F)(F)F)nc1OC1CCCC1)Nc1cccc2[nH]c(=O)[nH]c12]

White solid, yield 62%; $^1$H-NMR (400 MHz, DMSO-D6) δ 10.66 (s, 1H), 10.09 (s, 1H), 9.90 (s, 1H), 8.18 (d, J=7.8 Hz, 1H), 7.63 (d, J=16.1 Hz, 1H), 7.50 (d, J=7.4 Hz, 1H), 7.13 (d, J=8.3 Hz, 1H), 6.99 (d, J=16.1 Hz, 1H), 6.89 (t, J=7.8 Hz, 1H), 6.74 (d, J=7.8 Hz, 1H), 5.45 (s, 1H), 2.01 (t, J=6.4 Hz, 3H), 1.92 (s, 2H), 1.69-1.79 (m, 4H), 1.59 (d, J=8.3 Hz, 3H); Mass (ESI) m/z 433 $[M+H]^+$ <Example 13> (E)-3-(2-(cyclopropylmethoxy)-6-(trifluoromethyl)pyridin-3-yl)-N-(2-oxo-2,3-dihydro-1H-benzo[d]imidazol-4-yl)acrylamide

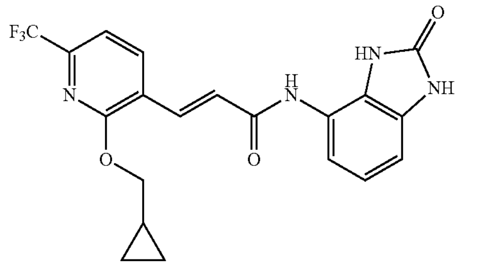 [SMILES: O=C(/C=C/c1ccc(C(F)(F)F)nc1OCC1CC1)Nc1cccc2[nH]c(=O)[nH]c12]

Pale yellow solid, yield 82%; $^1$H NMR (600 MHz, DMSO) δ 10.70 (s, 1H), 10.14 (s, 1H), 9.95 (s, 1H), 8.24 (d, J=7.80 Hz, 1H), 7.73 (d, J=16.02 Hz, 1H), 7.57 (d, J=7.38 Hz, 1H), 7.20 (d, J=8.28 Hz, 1H), 7.07 (d, J=16.02 Hz, 1H), 6.93 (t, J=8.28 Hz, 1H), 6.77 (d, J=7.80 Hz, 1H), 4.29 (d, J=6.84 Hz, 2H), 1.35 (m, 1H), 0.60 (q, J=6.42 Hz, 2H), 0.42 (q, J=5.04 Hz, 2H); Mass (ESI) m/z 419 $[M+H]^+$ <Example 14> (E)-N-(2-oxo-2,3-dihydro-1H-benzo[d]imidazol-4-yl)-3-(2-(2,2,2-trifluoroethoxy)-6-(trifluoromethyl)pyridin-3-yl)acrylamide

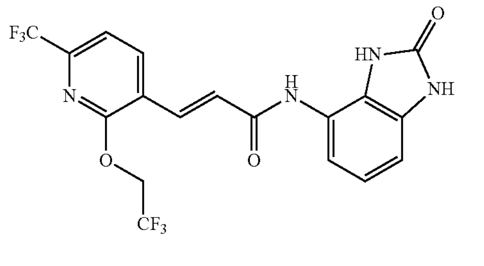 [SMILES: O=C(/C=C/c1ccc(C(F)(F)F)nc1OCC(F)(F)F)Nc1cccc2[nH]c(=O)[nH]c12]

Pale yellow solid, yield 62%; $^1$H-NMR (400 MHz, DMSO) δ 10.68 (s, 1H), 10.14 (s, 1H), 9.98 (s, 1H), 8.33 (d, J=7.2 Hz, 1H), 7.69 (m, 2H), 7.14 (d, J=7.6 Hz, 1H), 6.96 (d, J=15.6 Hz, 1H), 6.89 (t, J=8.0 Hz, 1H), 6.74 (d, J=8.8 Hz, 1H), 5.11 (q, J=8.8 Hz, 2H); Mass (FAB) m/z 447 $[M+H]^+$ <Example 15> (E)-3-(2-(neopentyloxy)-6-(trifluoromethyl)pyridin-3-yl)-N-(2-oxo-2,3-dihydro-1H-benzo[d]imidazol-4-yl)acrylamide

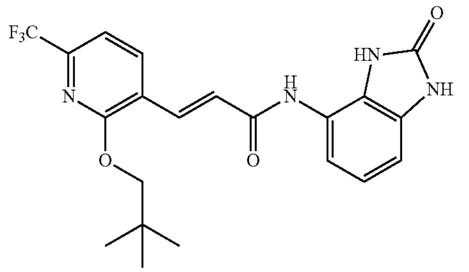 [SMILES: CC(C)(C)COc1nc(C(F)(F)F)ccc1/C=C/C(=O)Nc1cccc2[nH]c(=O)[nH]c12]

Yellow solid, yield 52%; $^1$H-NMR (400 MHz, DMSO) δ 10.68 (s, 1H), 10.13 (s, 1H), 9.91 (s, 1H), 8.22 (d, J=7.6 Hz, 1H), 7.74 (d, J=16.0 Hz, 1H), 7.75 (d, J=0.80 Hz, 1H), 7.15 (d, J=8.4 Hz, 1H), 6.95 (d, J=8.4 Hz, 1H), 6.88 (t, J=8.4 Hz, 1H), 6.73 (d, J=7.6 Hz, 1H), 4.60 (s, 2H), 1.02 (s, 9H); Mass (FAB) m/z 435 $[M+H]^+$ <Example 16> (E)-3-(2-((2-methylcyclopropyl)methoxy)-6-(trifluoromethyl)pyridin-3-yl)-N-(2-oxo-2,3-dihydro-1H-benzo[d]imidazol-4-yl)acrylamide

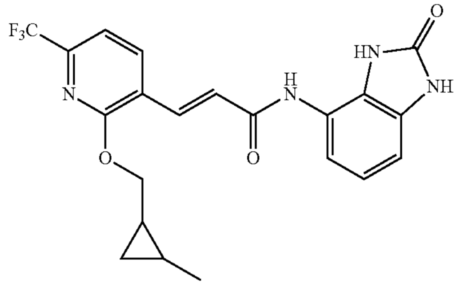 [SMILES: CC1CC1COc1nc(C(F)(F)F)ccc1/C=C/C(=O)Nc1cccc2[nH]c(=O)[nH]c12]

Yellow solid, yield 63%; $^1$H-NMR (400 MHz, DMSO) δ 10.69 (s, 1H), 10.15 (s, 1H), 9.94 (s, 1H), 8.20 (d, J=7.6 Hz, 1H), 7.72-7.66 (m, 1H), 7.52 (d, J=8.0 Hz, 1H), 7.16 (d, J=7.6 Hz, 1H), 7.03 (d, J=16.0 Hz, 1H), 6.89 (t, J=8.0 Hz, 1H), 6.74 (d, J=7.2 Hz, 1H), 4.32-4.18 (m, 2H), 0.99 (d, J=6.0 Hz, 3H), 0.81-0.80 (m, 2H), 0.54 (m, 1H), 0.32 (m, 1H); Mass (FAB) m/z 433 $[M+H]^+$ <Example 17> (E)-3-(6-(chlorodifluoromethyl)-2-(cyclopropylmethoxy)pyridin-3-yl)-N-(2-oxo-2,3-dihydro-1H-benzo[d]imidazol-4-yl)acrylamide

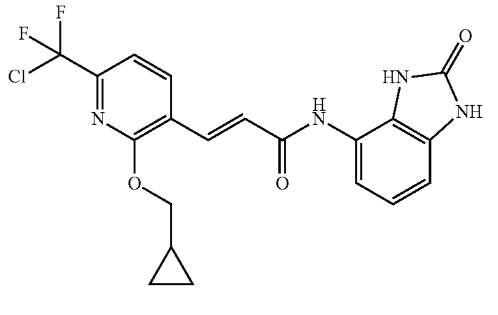 [SMILES: O=C(/C=C/c1ccc(C(F)(F)Cl)nc1OCC1CC1)Nc1cccc2[nH]c(=O)[nH]c12]

White solid, yield 71%; $^1H$ NMR (400 MHz, DMSO) δ 10.67 (s, 1H), 10.23 (s, 1H), 10.02 (s, 1H), 8.20 (d, J=8.0 Hz, 1H), 7.68 (d, J=16.0 Hz, 1H), 7.46 (d, J=7.6 Hz, 1H), 7.19 (d, J=8.0 Hz, 1H), 7.05 (d, J=16.0 Hz, 1H), 6.88 (t, J=8.4 Hz, 1H), 6.73 (d, J=7.6 Hz, 1H), 4.26 (d, J=7.2 Hz, 2H), 1.33 (m, 1H), 0.55 (d, J=8.0 Hz, 2H), 0.38 (d, J=5.2 Hz, 2H); Mass (ESI) m/z 435 $[M+H]^+$ <Example 18> (E)-3-(6-cyclopropyl-2-(cyclopropylmethoxy)pyridin-3-yl)-N-(2-oxo-2,3-dihydro-1H-benzo[d]imidazol-4-yl)acrylamide

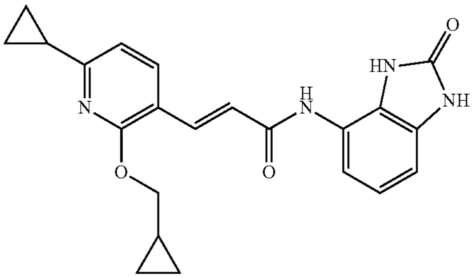

White solid, yield 82%; $^1H$ NMR (400 MHz, DMSO) δ 10.66 (s, 1H), 10.09 (s, 1H), 9.75 (s, 1H), 7.80 (d, J=7.8 Hz, 1H), 7.64 (d, J=16.0 Hz, 1H), 7.19 (t, J=8.0 Hz, 1H), 6.96 (d, J=7.8 Hz, 1H), 6.79-6.90 (m, 2H), 6.71 (d, J=7.3 Hz, 1H), 4.14 (d, J=6.9 Hz, 2H), 1.99-2.05 (m, 1H), 0.93 (d, J=6.4 Hz, 4H), 0.81 (t, J=6.9 Hz, 1H), 0.53 (d, J=6.9 Hz, 2H), 0.31 (d, J=4.6 Hz, 2H); Mass (FAB) m/z 391 $[M+H]^+$ <Example 19> (E)-3-(2-(cyclopropylmethoxy)-6-isopropylpyridin-3-yl)-N-(2-oxo-2,3-dihydro-1H-benzo[d]imidazol-4-yl)acrylamide

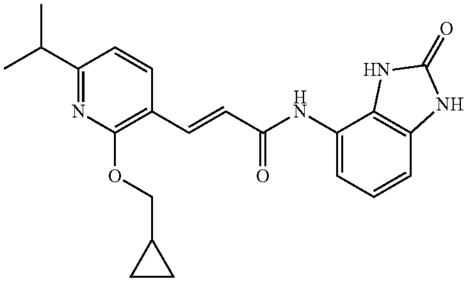 [SMILES: CC(C)c1ccc(/C=C/C(=O)Nc2cccc3[nH]c(=O)[nH]c23)c(OCC2CC2)n1]

White solid, yield 52%; $^1H$ NMR (400 MHz, DMSO) δ 10.67 (s, 1H), 10.10 (s, 1H), 9.77 (s, 1H), 7.87 (d, J=7.6 Hz, 1H), 7.67 (d, J=16.0 Hz, 1H), 7.20 (d, J=8.0 Hz, 1H), 6.92-6.83 (m, 3H), 6.72 (d, J=7.2 Hz, 1H), 4.23 (d, J=6.8 Hz, 2H), 2.94-2.87 (m, 1H), 1.36-1.27 (m, 1H), 1.19 (d, J=6.8 Hz, 6H), 0.56-0.51 (m, 2H), 0.35-0.33 (m, 2H); Mass (FAB) m/z 393 $[M+H]^+$ <Example 20> (E)-3-(2-(cyclopropylmethoxy)-6-(1-methylcyclopropyl)pyridin-3-yl)-N-(2-oxo-2,3-dihydro-1H-benzo[d]imidazol-4-yl)acrylamide

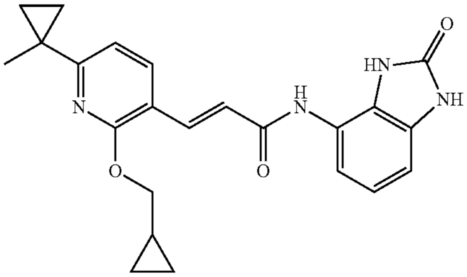 [SMILES: CC1(c2ccc(/C=C/C(=O)Nc3cccc4[nH]c(=O)[nH]c34)c(OCC3CC3)n2)CC1]

Yellow solid, yield 61%; $^1H$ NMR (400 MHz, DMSO) δ 10.65 (s, 1H), 10.23 (s, 1H), 9.87 (s, 1H), 7.86 (d, J=8.4 Hz, 1H), 7.65 (d, J=16.0 Hz, 1H), 7.23 (d, J=8.0 Hz, 1H), 6.98 (d, J=8.0 Hz, 1H), 6.89-6.84 (m, 2H), 6.70 (d, J=8.0 Hz, 1H), 4.13 (d, J=6.8 Hz, 2H), 1.42 (s, 3H), 1.27-1.25 (m, 1H), 1.18-1.17 (m, 2H), 0.81-0.78 (m, 2H), 0.55-0.52 (m, 2H), 0.32-0.31 (m, 2H); Mass (FAB) m/z 405 $[M+H]^+$ <Example 21> (E)-3-(2-(cyclopropylmethoxy)-6-(difluoromethyl)pyridin-3-yl)-N-(2-oxo-2,3-dihydro-1H-benzo[d]imidazol-4-yl)acrylamide

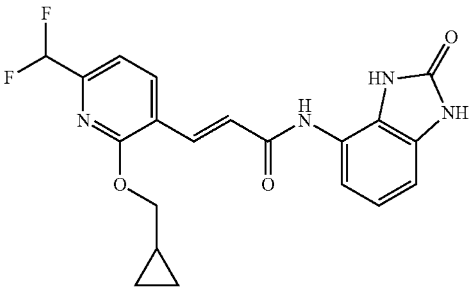 [SMILES: O=C(/C=C/c1ccc(C(F)F)nc1OCC1CC1)Nc1cccc2[nH]c(=O)[nH]c12]

Yellow solid, yield 70%; $^1H$ NMR (DMSO, 400 MHz) δ 10.68 (s, 1H), 10.21 (s, 1H), 9.97 (s, 1H), 8.14 (d, J=7.2 Hz, 1H), 7.69 (d, J=16.0 Hz, 1H), 7.32 (d, J=7.2 Hz, 1H), 7.18 (d, J=8.0 Hz, 1H), 7.02-6.72 (m, 4H), 4.23 (d, J=6.8 Hz, 2H), 1.33-1.28 (m, 1H), 0.57-0.53 (m, 2H), 0.38-0.34 (m, 2H); Mass (FAB) m/z 401 $[M+H]^+$ <Example 22> (E)-3-(2-(cyclopropylmethoxy)-6-(1,1-difluoroethyl)pyridin-3-yl)-N-(2-oxo-2,3-dihydro-1H-benzo[d]imidazol-4-yl)acrylamide

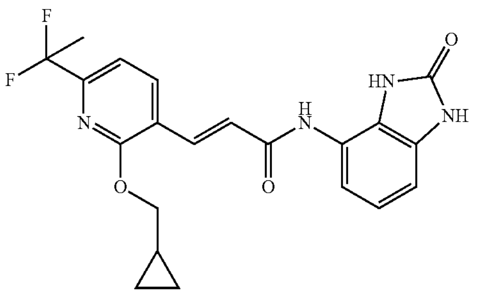 [SMILES: CC(F)(F)c1ccc(/C=C/C(=O)Nc2cccc3[nH]c(=O)[nH]c23)c(OCC2CC2)n1]

Yellow solid, yield 59%; $^1$H NMR (DMSO, 400 MHz) δ 10.67 (s, 1H), 10.20 (s, 1H), 9.97 (s, 1H), 8.12 (d, J=8.0 Hz, 1H), 7.69 (d, J=16.0 Hz, 1H), 7.32 (d, J=7.6 Hz, 1H), 7.19 (d, J=8.4 Hz, 1H), 6.99 (d, J=16.0 Hz, 1H), 6.89 (t, J=8.0 Hz, 1H), 6.73 (d, J=7.6 Hz, 1H), 4.25 (d, J=6.8 Hz, 2H), 1.95 (t, J=18.8 Hz, 3H), 1.35-1.30 (m, 1H), 0.58-0.53 (m, 2H), 0.38-0.35 (m, 2H); Mass (FAB) m/z 415 $[M+H]^+$ <Example 23> (E)-3-(6-(tert-butyl)-2-(cyclopropylmethoxy)pyridin-3-yl)-N-(2-oxo-2,3-dihydro-1H-benzo[d]imidazol-4-yl)acrylamide

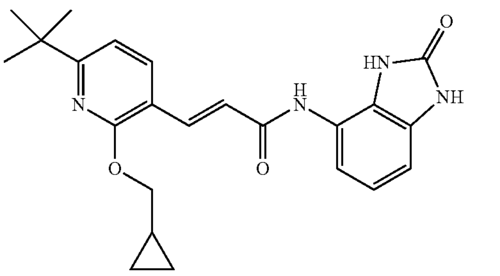 [SMILES: CC(C)(C)c1ccc(/C=C/C(=O)Nc2cccc3[nH]c(=O)[nH]c23)c(OCC2CC2)n1]

Yellow solid, yield 59%; $^1$H NMR (DMSO, 400 MHz) δ 10.66 (s, 1H), 10.17 (s, 1H), 9.84 (s, 1H), 7.88 (d, J=8.0 Hz, 1H), 7.66 (d, J=15.6 Hz, 1H), 7.21 (d, J=8.0 Hz, 1H), 7.02 (d, J=7.6 Hz, 1H), 6.89-6.85 (m, 2H), 6.71 (d, J=8.0 Hz, 1H), 4.23 (d, J=6.8 Hz, 2H), 1.36-1.30 (m, 1H), 1.26 (s, 9H), 0.56-0.51 (m, 2H), 0.35-0.33 (m, 2H); Mass (FAB) m/z 407 $[M+H]^+$ <Example 24> (E)-3-(2-(cyclopropylmethoxy)-6-(2-hydroxypropan-2-yl)pyridin-3-yl)-N-(2-oxo-2,3-dihydro-1H-benzo[d]imidazol-4-yl)acrylamide

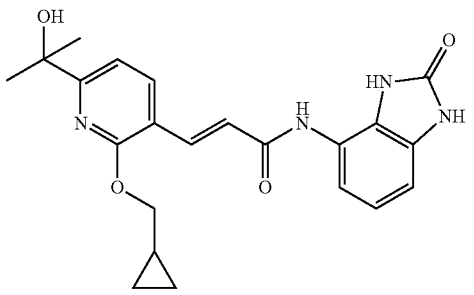 [SMILES: CC(C)(O)c1ccc(/C=C/C(=O)Nc2cccc3[nH]c(=O)[nH]c23)c(OCC2CC2)n1]

Yellow solid, yield 63%; $^1$H NMR (DMSO, 400 MHz) δ 10.65 (s, 1H), 10.33 (s, 1H), 9.98 (s, 1H), 7.95 (d, J=7.6 Hz, 1H), 7.68 (d, J=16.0 Hz, 1H), 7.25 (d, J=7.6 Hz, 1H), 6.93-6.86 (m, 2H), 6.71 (d, J=7.6 Hz), 5.12 (s, 1H), 4.22 (d, J=7.2 Hz, 2H), 1.39 (s, 6H), 1.34-1.27 (m, 1H), 0.56-0.51 (m, 2H), 0.36-0.32 (m, 2H); Mass (FAB) m/z 409 $[M+H]^+$ <Example 25> (E)-3-(2-(cyclobutylmethoxy)-6-(trifluoromethyl)pyridin-3-yl)-N-(2-oxo-2,3-dihydro-1H-benzo[d]imidazol-4-yl)acrylamide

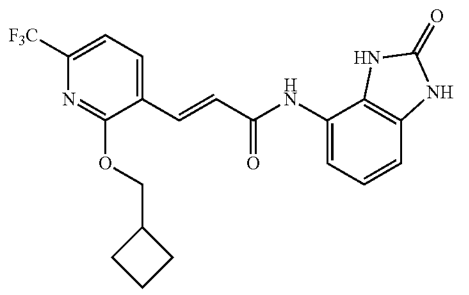 [SMILES: O=C(/C=C/c1ccc(C(F)(F)F)nc1OCC1CCC1)Nc1cccc2[nH]c(=O)[nH]c12]

Yellow solid, yield 83%; $^1$H NMR (300 MHz, DMSO) δ 10.72 (s, 1H), 10.10 (s, 1H), 9.91 (s, 1H), 7.97 (d, J=7.60 Hz, 1H), 7.69 (d, J=15.36 Hz, 1H), 7.55 (d, J=7.68 Hz, 1H), 7.15 (d, J=7.95 Hz, 1H), 7.01 (d, J=15.93 Hz, 1H), 6.92 (m, 1H), 6.78 (d, J=7.95 Hz, 1H), 4.40 (d, J=6.96 Hz, 2H), 2.01 (m, 2H), 1.89 (m, 3H), 1.21 (m, 2H); Mass (FAB) m/z 433 $[M+H]^+$ <Example 26> (E)-3-(2-(cyclopentylmethoxy)-6-(trifluoromethyl)pyridin-3-yl)-N-(2-oxo-2,3-dihydro-1H-benzo[d]imidazol-4-yl)acrylamide

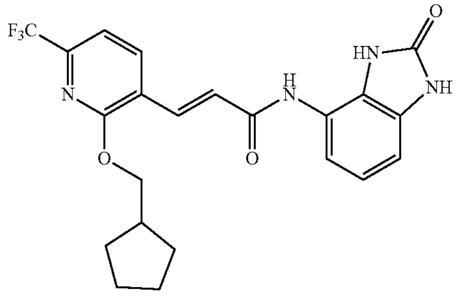 [SMILES: O=C(/C=C/c1ccc(C(F)(F)F)nc1OCC1CCCC1)Nc1cccc2[nH]c(=O)[nH]c12]

Yellow solid, yield 63%; $^1$H NMR (300 MHz, DMSO) δ 10.72 (s, 1H), 10.16 (s, 1H), 9.94 (s, 1H), 8.24 (d, J=7.71 Hz, 1H), 7.72 (d, J=15.75 Hz, 1H), 7.57 (d, J=7.68 Hz, 1H), 7.19 (d, J=7.89 Hz, 1H), 7.04 (d, J=15.75 Hz, 1H), 6.93 (t, J=7.86 Hz, 1H), 6.78 (d, J=7.71 Hz, 1H), 4.31 (d, J=7.14 Hz, 2H), 2.46 (m, 1H), 1.80 (m, 2H), 1.61 (m, 4H), 1.37 (m, 2H); Mass (FAB) m/z 447 $[M+H]^+$ <Example 27> (E)-3-(2-(isobutylthio)-6-(trifluoromethyl)pyridin-3-yl)-N-(2-oxo-2,3-dihydro-1H-benzo[d]imidazol-4-yl)acrylamide

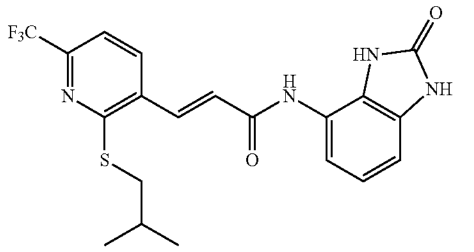 [SMILES: CC(C)CSc1nc(C(F)(F)F)ccc1/C=C/C(=O)Nc1cccc2[nH]c(=O)[nH]c12]

White solid, yield 55%; $^1$H NMR (400 MHz, DMSO) δ 10.73 (s, 1H), 10.22 (s, 1H), 10.08 (s, 1H), 8.15 (d, J=8.43 Hz, 1H), 7.22 (d, J=8.43 Hz, 1H), 7.73 (d, J=16.11 Hz, 1H), 7.71 (m, 1H), 6.96 (d, J=15.93 Hz, 1H), 6.92 (d, J=7.89 Hz, 1H), 6.78 (d, J=7.86 Hz, 1H), 3.17 (d, J=6.24 Hz, 2H), 1.94 (m, 1H), 1.00 (d, J=6.42 Hz, 6H); Mass (FAB) m/z 437 $[M+H]^+$ <Example 28> (E)-3-(2-((cyclopropylmethyl)thio)-6-(trifluoromethyl)pyridin-3-yl)-N-(2-oxo-2,3-dihydro-1H-benzo[d]imidazol-4-yl)acrylamide

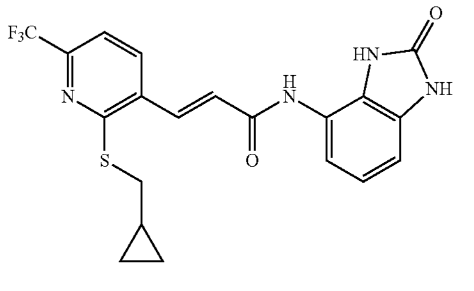 [SMILES: O=C(/C=C/c1ccc(C(F)(F)F)nc1SCC1CC1)Nc1cccc2[nH]c(=O)[nH]c12]

White solid, yield 55%; $^1$H NMR (400 MHz, DMSO) δ10.67 (s, 1H), 10.11 (s, 1H), 9.98 (s, 1H), 8.14 (d, J=7.88 Hz, 1H), 7.70 (d, J=7.88 Hz, 1H), 7.72 (d, J=15.56 Hz, 1H), 7.22 (d, J=8.12 Hz, 1H), 6.94 (d, J=8.24 Hz, 1H), 6.62 (d, J=7.64 Hz, 1H), 6.78 (d, J=7.68 Hz, 1H), 6.93 (d, J=15.88 Hz, 1H), 3.21 (d, J=7.20 Hz, 2H), 1.16 (m, 1H), 0.55 (m, 2H), 0.3469 (m, 2H); Mass (FAB) m/z 435 $[M+H]^+$ <Example 29> (E)-3-(2-(cyclohexylthio)-6-(trifluoromethyl)pyridin-3-yl)-N-(2-oxo-2,3-dihydro-1H-benzo[d]imidazol-4-yl)acrylamide

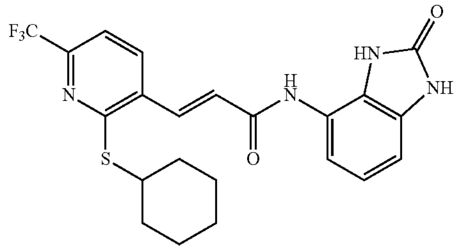 [SMILES: O=C(/C=C/c1ccc(C(F)(F)F)nc1SC1CCCCC1)Nc1cccc2[nH]c(=O)[nH]c12]

White solid, yield 59%; $^1$H NMR (400 MHz, DMSO) δ 10.72 (s, 1H), 10.19 (s, 1H), 10.04 (s, 1H), 8.14 (d, J=8.07 Hz, 1H), 7.70 (d, J=8.04 Hz, 1H), 7.67 (d, J=15.36 Hz, 1H), 7.22 (d, J=8.07 Hz, 1H), 6.94 (d, J=7.32 Hz, 1H), 6.93 (d, J=15.75 Hz, 1H), 6.78 (d, J=7.68 Hz, 1H), 3.91 (m, 1H), 2.03 (m, 2H), 1.72 (m, 2H), 1.51 (m, 6H); Mass (FAB) m/z 463 $[M+H]^+$ <Example 30> (E)-3-(2-(3-fluorophenyl)-6-(trifluoromethyl)pyridin-3-yl)-N-(2-oxo-2,3-dihydro-1H-benzo[d]imidazol-4-yl)acrylamide

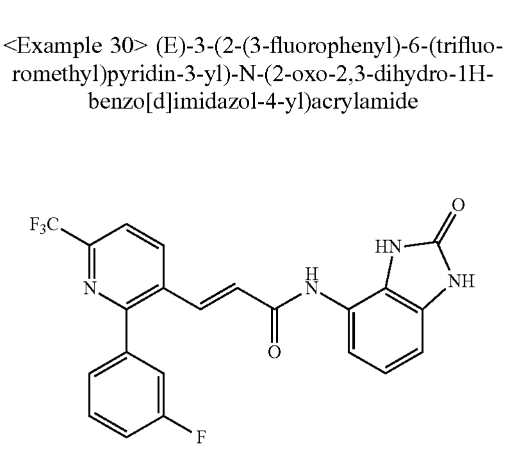

White solid, yield 75%; $^1$H NMR (400 MHz, DMSO) δ10.72 (s, 1H), 10.13 (s, 1H), 9.99 (s, 1H), 8.45 (d, J=8.43 Hz, 1H), 8.07 (d, J=8.58 Hz, 1H), 7.55 (m, 2H), 7.43 (m, 3H), 7.20 (d, J=8.25 Hz, 1H), 6.93 (m, 2H), 6.76 (d, J=7.86 Hz, 1H); Mass (FAB) m/z 443 $[M+H]^+$ <Example 31> (E)-3-(2-(3-chlorophenyl)-6-(trifluoromethyl)pyridin-3-yl)-N-(2-oxo-2,3-dihydro-1H-benzo[d]imidazol-4-yl)acrylamide

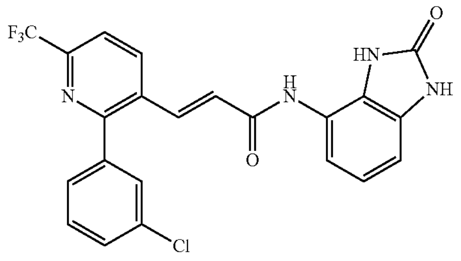 [SMILES: O=C(/C=C/c1ccc(C(F)(F)F)nc1-c1cccc(Cl)c1)Nc1cccc2[nH]c(=O)[nH]c12]

White solid, yield 62%; $^1$H NMR (300 MHz, DMSO) δ 10.72 (s, 1H), 10.11 (s, 1H), 9.98 (s, 1H), 8.45 (d, J=8.2 Hz, 1H), 8.07 (d, J=8.3 Hz, 1H), 7.51-7.65 (m, 5H), 7.20 (d, J=8.3 Hz, 1H), 6.89-6.98 (m, 2), 6.71 (d, J=7.50 Hz, 1H); Mass (ESI) m/z 459 $[M+H]^+$ <Example 32> (E)-3-(2-(3-isopropylphenyl)-6-(trifluoromethyl)pyridin-3-yl)-N-(2-oxo-2,3-dihydro-1H-benzo[d]imidazol-4-yl)acrylamide

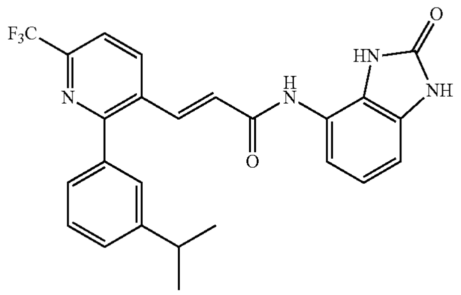 [SMILES: CC(C)c1cccc(-c2nc(C(F)(F)F)ccc2/C=C/C(=O)Nc2cccc3[nH]c(=O)[nH]c23)c1]

White solid, yield 82%; $^1$H NMR (300 MHz, DMSO) δ 10.71 (s, 1H), 10.05 (s, 1H), 9.95 (s, 1H), 8.42 (d, J=7.7 Hz, 1H), 8.02 (d, J=8.1 Hz, 1H), 7.59 (d, J=15.8 Hz, 1H), 7.39-7.51 (m, 4H), 7.20 (d, J=8.4 Hz, 1H), 6.89-6.97 (m, 2H), 6.76 (d, J=7.7 Hz, 1H), 2.98 (m, 1H), 1.24 (d, J=6.8 Hz, 6H); Mass (FAB) m/z 467 $[M+H]^+$ <Example 33> (E)-3-(2-(3-chloro-4-fluorophenyl)-6-(trifluoromethyl)pyridin-3-yl)-N-(2-oxo-2,3-dihydro-1H-benzo[d]imidazol-4-yl)acrylamide

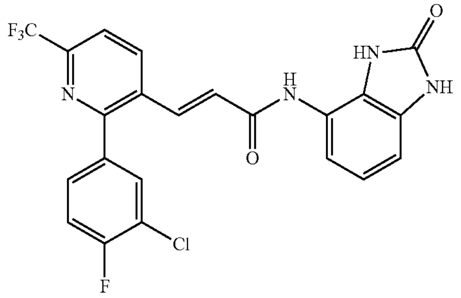 [SMILES: O=C(/C=C/c1ccc(C(F)(F)F)nc1-c1ccc(F)c(Cl)c1)Nc1cccc2[nH]c(=O)[nH]c12]

White solid, yield 82%; $^1$H NMR (300 MHz, DMSO) δ 10.72 (s, 1H), 10.10 (s, 1H), 9.98 (s, 1H), 8.44 (d, J=6.1 Hz, 1H), 8.07 (d, J=8.2 Hz, 1H), 7.81 (dd, J=1.8, 7.1 Hz, 1H), 7.59-7.66 (m, 2H), 7.53 (d, J=15.4 Hz, 1H), 7.21 (d, J=8.3 Hz, 1H), 0.6.89-6.97 (m, 2H), 6.77 (d, J=7.50 Hz, 1H); Mass (FAB) m/z 477 $[M+H]^+$ <Example 34> (E)-3-(2-(4-fluorophenyl)-6-(trifluoromethyl)pyridin-3-yl)-N-(2-oxo-2,3-dihydro-1H-benzo[d]imidazol-4-yl)acrylamide

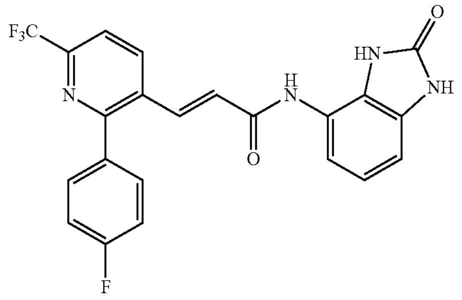 [SMILES: O=C(/C=C/c1ccc(C(F)(F)F)nc1-c1ccc(F)cc1)Nc1cccc2[nH]c(=O)[nH]c12]

White solid, yield 69%; $^1$H NMR (400 MHz, DMSO) δ 10.71 (s, 1H), 10.13 (s, 1H), 10.00 (s, 1H), 8.41 (d, J=8.07 Hz, 1H), 8.01 (d, J=8.25 Hz, 1H), 7.63 (m, 2H), 7.53 (d, J=15.54 Hz, 1H), 7.39 (m, 2H), 7.20 (d, J=8.22 Hz, 1H), 6.93 (m, 2H), 6.75 (d, J=7.68 Hz, 1H); Mass (FAB) m/z 443 $[M+H]^+$ <Example 35> (E)-N-(2-oxo-2,3-dihydro-1H-benzo[d]imidazol-4-yl)-3-(2-(thiophen-2-yl)-6-(trifluoromethyl)pyridin-3-yl)acrylamide

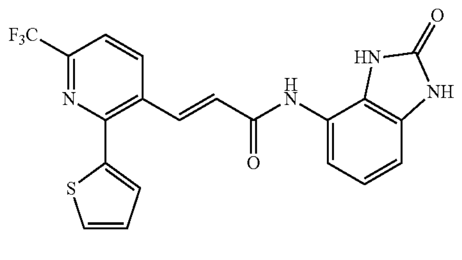 [SMILES: O=C(/C=C/c1ccc(C(F)(F)F)nc1-c1cccs1)Nc1cccc2[nH]c(=O)[nH]c12]

Yellow solid, yield 71%; $^1$H NMR (400 MHz, DMSO) δ 10.70 (s, 1H), 10.14 (s, 1H), 10.01 (s, 1H), 8.27 (d, J=7.8 Hz, 1H), 7.83-7.91 (m, 3H), 7.48-7.48 (m, 1H), 7.25 (dd, J=5.3, 3.9 Hz, 1H), 7.17 (d, J=8.3 Hz, 1H), 6.85-6.92 (m, 2H), 6.75 (d, J=7.8 Hz, 1H); Mass (FAB) m/z 431 $[M+H]^+$ <Example 36> (E)-3-(2-(furan-2-yl)-6-(trifluoromethyl)pyridin-3-yl)-N-(2-oxo-2,3-dihydro-1H-benzo[d]imidazol-4-yl)acrylamide

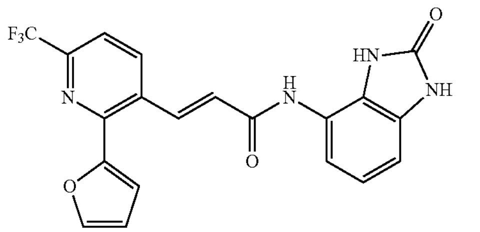 [SMILES: O=C(/C=C/c1ccc(C(F)(F)F)nc1-c1ccco1)Nc1cccc2[nH]c(=O)[nH]c12]

Pale brown solid, yield 61%; $^1$H NMR (400 MHz, DMSO) δ 10.69 (s, 1H), 10.12 (s, 1H), 9.97 (s, 1H), 8.29 (d, J=8.0 Hz, 1H), 8.00-8.07 (m, 2H), 7.89 (d, J=8.2 Hz, 1H), 7.19 (d, J=8.2 Hz, 1H), 7.08 (d, J=3.7 Hz, 1H), 6.83-6.92 (m, 2H), 6.73-6.76 (m, 2H); Mass (FAB) m/z 415 $[M+H]^+$ <Example 37> (E)-3-(2-(oxazol-2-yl)-6-(trifluoromethyl)pyridin-3-yl)-N-(2-oxo-2,3-dihydro-1H-benzo[d]imidazol-4-yl)acrylamide

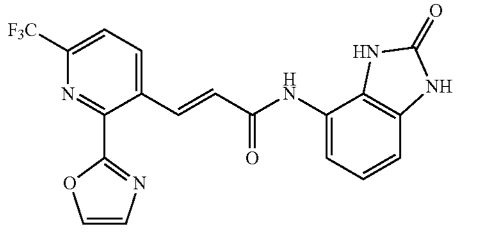 [SMILES: O=C(/C=C/c1ccc(C(F)(F)F)nc1-c1ncco1)Nc1cccc2[nH]c(=O)[nH]c12]

Pale brown solid, yield 58%; $^1$H NMR (300 MHz, DMSO) δ 10.69 (s, 1H), 10.12 (s, 1H), 9.97 (s, 1H), 8.29 (d, J=8.0 Hz, 1H), 7.75 (d, J=8.2 Hz, 1H), 7.60 (d, J=8.2 Hz, 1H), 7.15 (m, 2H), 6.83-6.92 (m, 2H), 6.73-6.76 (m, 2H); Mass (FAB) m/z 416 $[M+H]^+$ <Example 38> (E)-3-(2-(oxazol-5-yl)-6-(trifluoromethyl)pyridin-3-yl)-N-(2-oxo-2,3-dihydro-1H-benzo[d]imidazol-4-yl)acrylamide

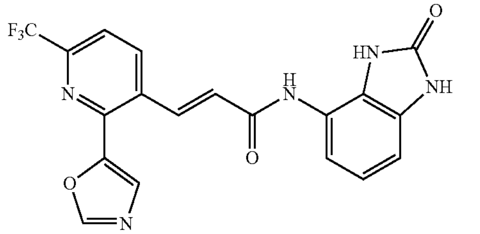 [SMILES: O=C(/C=C/c1ccc(C(F)(F)F)nc1-c1cnco1)Nc1cccc2[nH]c(=O)[nH]c12]

Pale brown solid, yield 51%; $^1$H NMR (400 MHz, DMSO) δ 10.69 (s, 1H), 10.12 (s, 1H), 9.97 (s, 1H), 8.29 (s, 1H), 7.75 (d, J=8.2 Hz, 1H), 7.60 (d, J=8.2 Hz, 1H), 7.09 (m, 2H), 6.83-6.92 (m, 2H), 6.73-6.76 (m, 2H); Mass (FAB) m/z 416 $[M+H]^+$ <Example 39> (E)-3-(2-(3,3-dimethyl-1-butyn-1-yl)-6-(trifluoromethyl)pyridin-3-yl)-N-(2-oxo-2,3-dihydro-1H-benzo[d]imidazol-4-yl)acrylamide

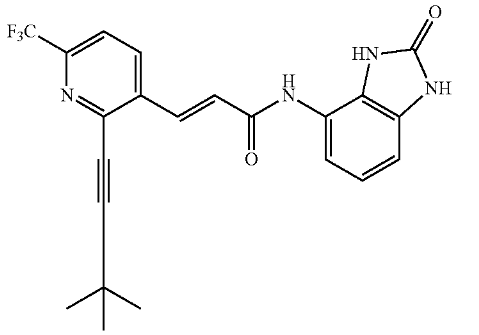 [SMILES: CC(C)(C)CC#Cc1nc(C(F)(F)F)ccc1/C=C/C(=O)Nc1cccc2[nH]c(=O)[nH]c12]

Yellow solid, yield 67%; $^1$H-NMR (400 MHz, DMSO) δ 10.70 (s, 1H), 10.16 (s, 1H), 9.99 (s, 1H), 8.35 (d, J=8.0 Hz, 1H), 7.95 (d, J=16.0 Hz, 1H), 7.16 (d, J=8.0 Hz, 1H), 7.02 (d, J=16.0 Hz, 1H), 6.89 (t, J=8.0 Hz, 1H), 6.75 (d, J=8.0 Hz, 1H), 1.35 (s, 9H); Mass (FAB) m/z 429 $[M+H]^+$ <Example 40> (E)-3-(2-(3,3-dimethylbutyl)-6-(trifluoromethyl)pyridin-3-yl)-N-(2-oxo-2,3-dihydro-1H-benzo[d]imidazol-4-yl)acrylamide

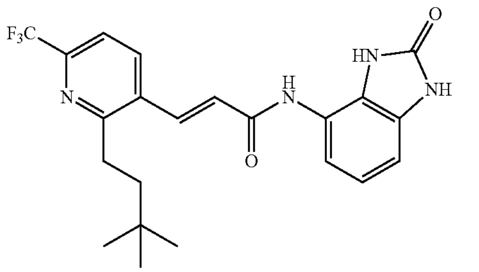 [SMILES: CC(C)(C)CCc1nc(C(F)(F)F)ccc1/C=C/C(=O)Nc1cccc2[nH]c(=O)[nH]c12]

Yellow solid, yield 82%; $^1$H-NMR (400 MHz, DMSO) δ 10.70 (s, 1H), 10.14 (s, 1H), 9.97 (s, 1H), 8.20 (d, J=8.0 Hz, 1H), 7.80 (m, 2H), 7.19 (d, J=8.0 Hz, 1H), 6.87-6.91 (m, 2H), 6.72 (d, J=8.0 Hz, 1H), 2.88 (m, 2H), 1.47 (m, 2H); Mass (FAB) m/z 433 $[M+H]^+$ <Example 41> (E)-3-(2-cyclopentyl-6-(trifluoromethyl)pyridin-3-yl)-N-(2-oxo-2,3-dihydro-1H-benzo[d]imidazol-4-yl)acrylamide

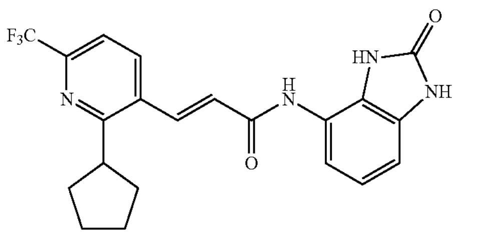 [SMILES: O=C(/C=C/c1ccc(C(F)(F)F)nc1C1CCCC1)Nc1cccc2[nH]c(=O)[nH]c12]

Yellow solid, yield 82%; $^1$H-NMR (400 MHz, DMSO) δ 10.69 (s, 1H), 10.13 (s, 1H), 9.95 (s, 1H), 8.14 (d, J=8.0 Hz, 1H), 7.87 (d, J=15.6 Hz, 1H), 7.76 (d, J=8.0 Hz, 1H), 7.16 (d, J=7.6 Hz, 1H), 6.89 (t, J=7.6 Hz, 1H), 6.80-6.73 (m, 2H), 3.62-3.54 (m, 1H), 1.95 (m, 2H), 1.85-1.76 (m, 4H), 1.65 (m, 2H); Mass (FAB) m/z 417 $[M+H]^+$ <Example 42> (E)-3-(2-isobutoxy-4-(trifluoromethyl)phenyl)-N-(2-oxo-2,3-dihydro-1H-benzo[d]imidazol-4-yl)acrylamide

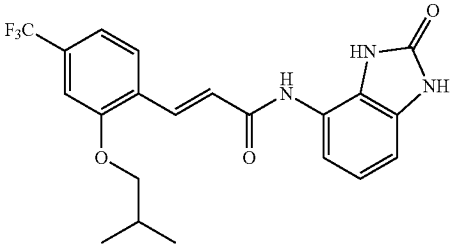 [SMILES: CC(C)COc1cc(C(F)(F)F)ccc1/C=C/C(=O)Nc1cccc2[nH]c(=O)[nH]c12]

Yellow solid, yield 71%; $^1$H NMR (300 MHz, DMSO) δ 10.69 (s, 1H), 10.10 (s, 1H), 9.85 (s, 1H), 7.89 (d, J=15.2 Hz, 1H), 7.80 (d, J=7.9 Hz, 1H), 7.36 (m, 2H), 7.20 (d, J=8.2 Hz, 1H), 6.88-6.93 (m, 2H), 6.75 (d, J=7.7 Hz, 1H), 3.95 (d, J=6.2 Hz, 2H), 1.97-2.12 (m, 1H), 1.02 (d, J=6.6 Hz, 6H); Mass (ESI) m/z 420 $[M+H]^+$ <Example 43> (E)-3-(2-(cyclopropylmethoxy)-4-(trifluoromethyl)phenyl)-N-(2-oxo-2,3-dihydro-1H-benzo[d]imidazol-4-yl)acrylamide

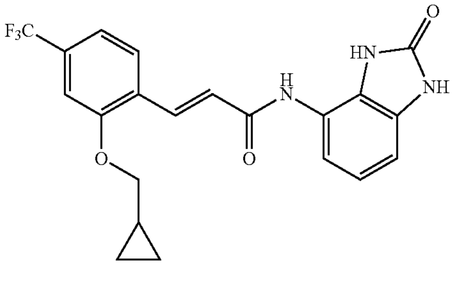

Yellow solid, yield 65%; $^1$H NMR (300 MHz, DMSO) δ 10.70 (s, 1H), 10.12 (s, 1H), 9.88, (s, 1H), 7.89 (d, J=15.8 Hz, 1H), 7.81 (d, J=7.7 Hz, 1H), 7.34-7.38 (m, 2H), 7.22 (d, J=8.8 Hz, 1H), 6.90-6.96 (m, 2H), 6.76 (d, J=7.7 Hz, 1H), 4.03 (d, J=7.1 Hz, 2H), 1.31-1.16 (m, 1H), 0.62 (m, 2H), 0.38 (m, 2H); Mass (FAB) m/z 418 $[M+H]^+$ <Example 44> (E)-3-(2-(cyclopropylmethoxy)-4-(2-hydroxypropan-2-yl)phenyl)-N-(2-oxo-2,3-dihydro-1H-benzo[d]imidazol-4-yl)acrylamide

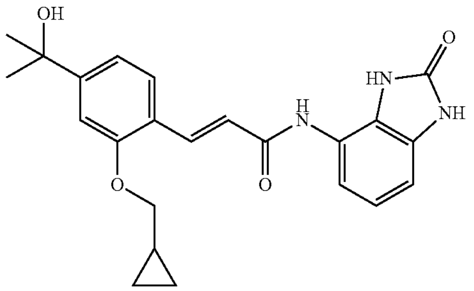 [SMILES: CC(C)(O)c1ccc(/C=C/C(=O)Nc2cccc3[nH]c(=O)[nH]c23)c(OCC2CC2)c1]

Yellow solid, yield 60%; $^1$H NMR (400 MHz, DMSO) δ 10.66 (s, 1H), 10.07 (s, 1H), 9.70 (s, 1H), 7.85 (d, J=15.6 Hz, 1H), 7.50 (d, J=7.8 Hz, 1H), 7.22 (d, J=8.2 Hz, 1H), 6.99-7.01 (m, 2H), 6.88 (t, J=8.0 Hz, 1H), 6.70-6.75 (m, 2H), 3.91 (d, J=6.9 Hz, 2H), 1.24 (s, 6H), 0.57 (t, J=6.2 Hz, 2H), 0.34 (t, J=5.0 Hz, 2H); Mass (FAB) m/z 408 $[M+H]^+$ <Example 45> (E)-3-(4-(tert-butyl)-2-(cyclopropylmethoxy)phenyl)-N-(2-oxo-2,3-dihydro-1H-benzo[d]imidazol-4-yl)acrylamide

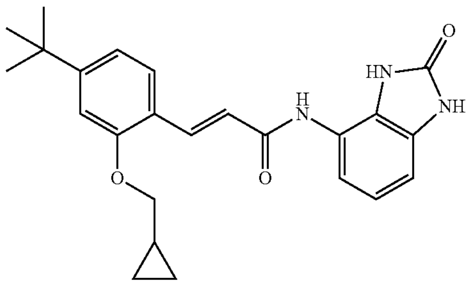 [SMILES: CC(C)(C)c1ccc(/C=C/C(=O)Nc2cccc3[nH]c(=O)[nH]c23)c(OCC2CC2)c1]

Yellow solid, yield 70%; $^1$H NMR (400 MHz, DMSO) δ 10.66 (s, 1H), 10.07 (s, 1H), 9.70 (s, 1H), 7.85 (d, J=15.6 Hz, 1H), 7.50 (d, J=7.8 Hz, 1H), 7.22 (d, J=8.2 Hz, 1H), 6.99-7.01 (m, 2H), 6.88 (t, J=8.0 Hz, 1H), 6.70-6.76 (m, 2H), 3.92 (d, J=6.9 Hz, 2H), 1.25 (s, 10H), 0.57 (t, J=6.2 Hz, 2H), 0.34 (t, J=5.0 Hz, 2H); Mass (FAB) m/z 406 $[M+H]^+$ <Example 46> (E)-3-(4-cyclopropyl-2-(cyclopropylmethoxy)phenyl)-N-(2-oxo-2,3-dihydro-1H-benzo[d]imidazol-4-yl)acrylamide

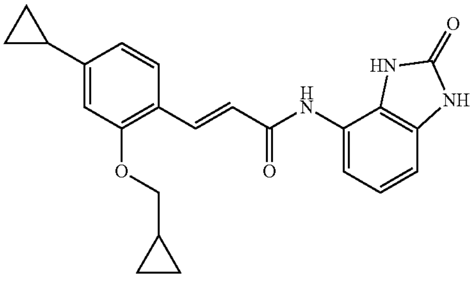

White solid, yield 82%; $^1$H-NMR (400 MHz, DMSO) δ 10.66 (s, 1H), 10.05 (s, 1H), 9.66 (s, 1H), 7.82 (d, J=15.6 Hz, 1H), 7.43 (d, J=7.8 Hz, 1H), 7.21 (d, J=7.8 Hz, 1H), 6.87 (t, J=8.0 Hz, 1H), 6.66-6.72 (m, 4H), 3.88 (d, J=6.9 Hz, 2H), 1.87-1.95 (m, 1H), 1.25 (m, 1H), 0.95 (t, J=6.4 Hz, 2H), 0.71 (d, J=4.6 Hz, 2H), 0.57 (d, J=7.8 Hz, 2H), 0.32 (d, J=4.6 Hz, 2H); Mass (FAB) m/z 390 $[M+H]^+$ <Example 47> (E)-3-(1-(3-chlorophenyl)-3-(trifluoromethyl)-1H-pyrazol-5-yl)-N-(2-oxo-2,3-dihydro-1H-benzo[d]imidazol-4-yl)acrylamide

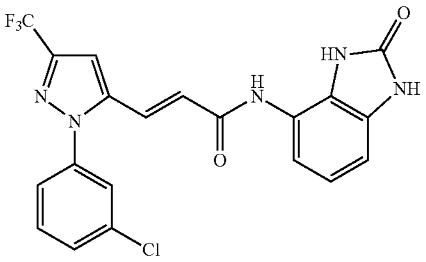 [SMILES: O=C(/C=C/c1cc(C(F)(F)F)nn1-c1cccc(Cl)c1)Nc1cccc2[nH]c(=O)[nH]c12]

White solid, yield 82%; $^1$H NMR (300 MHz, DMSO) δ 10.73 (s, 1H), 10.14 (s, 1H), 10.02 (s, 1H), 7.78 (m, 1H), 7.67 (m, 2H), 7.60 (m, 1H), 7.50 (s, 1H), 7.26 (d, J=15.54 Hz, 1H), 7.15 (d, J=7.86 Hz, 1H), 6.91 (t, J=8.04 Hz, 1H), 6.88 (d, J=15.6 Hz, 1H), 6.76 (d, J=7.68 Hz, 1H); Mass (FAB) m/z 448 $[M+H]^+$ <Example 48> (E)-N-(2-oxo-2,3-dihydro-1H-benzo[d]imidazol-4-yl)-3-(1-(m-tolyl)-3-(trifluoromethyl)-1H-pyrazol-5-yl)acrylamide

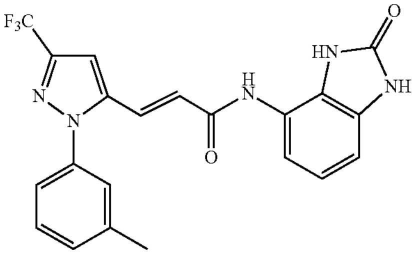 [SMILES: Cc1cccc(-n2nc(C(F)(F)F)cc2/C=C/C(=O)Nc2cccc3[nH]c(=O)[nH]c23)c1]

White solid, yield 60%; $^1$H NMR (300 MHz, DMSO) δ 10.69 (s, 1H), 10.11 (s, 1H), 9.99, (s, 1H), 7.42-7.55 (m, 4H), 7.35 (d, J=7.9 Hz, 1H), 7.26 (d, J=15.7 Hz, 1H), 7.15 (d, J=7.9 Hz, 1H), 6.86-6.93 (m, 2H), 6.76 (d, J=7.7 Hz, 1H), 2.42 (s, 3H); Mass (FAB) m/z 428 $[M+H]^+$ <Example 49> (E)-3-(1-(3-chloro-4-fluorophenyl)-3-(trifluoromethyl)-1H-pyrazol-5-yl)-N-(2-oxo-2,3-dihydro-1H-benzo[d]imidazol-4-yl)acrylamide

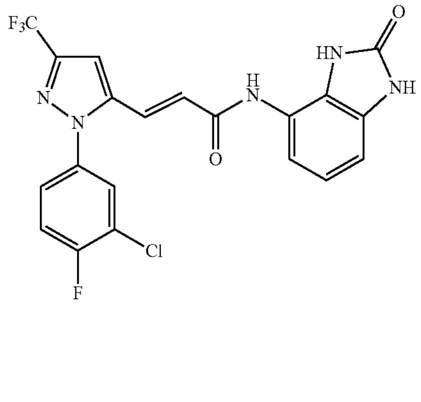 [SMILES: O=C(/C=C/c1cc(C(F)(F)F)nn1-c1ccc(F)c(Cl)c1)Nc1cccc2[nH]c(=O)[nH]c12]

Light yellow solid, yield 73%; $^1$H NMR (300 MHz, DMSO) δ 10.70 (s, 1H), 10.10 (s, 1H), 9.99, (s, 1H), 7.99 (dd, J=6.78, 2.55 Hz, 1H), 7.69-7.74 (m, 2H), 7.48 (s, 1H), 7.24 (d, J=15.8 Hz, 1H), 7.15 (d, J=8.1 Hz, 1H), 6.92 (d, J=8.0 Hz, 1H), 6.85 (d, J=16.3 Hz, 1H), 6.76 (d, J=7.9 Hz, 1H); Mass (FAB) m/z 466 $[M+H]^+$ <Example 50> (E)-3-(1-(3-isopropylphenyl)-3-(trifluoromethyl)-1H-pyrazol-5-yl)-N-(2-oxo-2,3-dihydro-1H-benzo[d]imidazol-4-yl)acrylamide

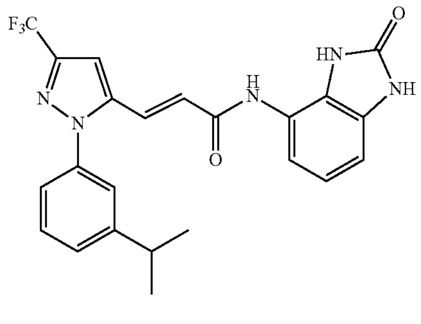 [SMILES: CC(C)c1cccc(-n2nc(C(F)(F)F)cc2/C=C/C(=O)Nc2cccc3[nH]c(=O)[nH]c23)c1]

Light yellow solid, yield 66%; $^1$H NMR (300 MHz, DMSO) δ 10.70 (s, 1H), 10.09 (s, 1H), 9.98 (s, 1H), 7.58-7.44 (m, 4H), 7.37 (m, 1H), 7.28 (d, J=15.75 Hz, 1H), 7.15 (d, J=8.25 Hz, 1H), 6.93-6.80 (m, 2H), 6.76 (d, J=7.5 Hz, 1H), 3.02 (m, 1H), 1.26 (s, 3H), 1.24 (s, 3H); Mass (FAB) m/z 456 $[M+H]^+$ <Example 51> (E)-3-(1-(3-chlorophenyl)-3-isopropyl-1H-pyrazol-5-yl)-N-(2-oxo-2,3-dihydro-1H-benzo[d]imidazol-4-yl)acrylamide

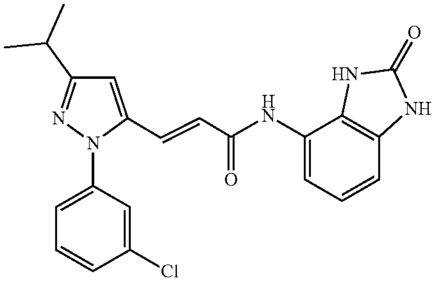 [SMILES: CC(C)c1cc(/C=C/C(=O)Nc2cccc3[nH]c(=O)[nH]c23)n(-c2cccc(Cl)c2)n1]

Yellow solid, yield 46%; $^1$H NMR (300 MHz, DMSO) δ 10.70 (s, 1H), 10.10 (s, 1H), 9.90 (s, 1H), 7.59 (m, 3H), 7.46 (m, 1H), 7.31 (d, J=15.39 Hz, 1H), 7.19 (m, 1H), 6.90 (m, 1H), 6.81 (m, 3H), 3.0 (m, 1H), 1.28 (d, J=6.96 Hz, 4H); Mass (FAB) m/z 422 [M+H]$^+$ <Example 52> (E)-3-(1-(3-chlorophenyl)-3-(1-methylcyclopropyl)-1H-pyrazol-5-yl)-N-(2-oxo-2,3-dihydro-1H-benzo[d]imidazol-4-yl)acrylamide

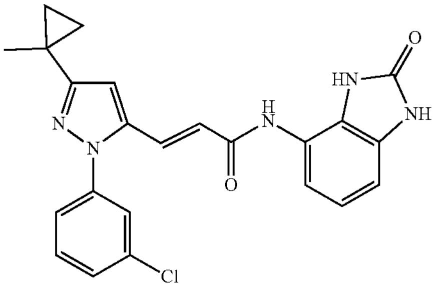 [SMILES: CC1(c2cc(/C=C/C(=O)Nc3cccc4[nH]c(=O)[nH]c34)n(-c3cccc(Cl)c3)n2)CC1]

Yellow solid, yield 87%; $^1$H NMR (300 MHz, DMSO) δ 10.70 (s, 1H), 10.10 (s, 1H), 9.90 (s, 1H), 7.61-7.58 (m, 3H), 7.44 (m, 1H), 7.28 (d, J=15.39 Hz, 1H), 7.20 (d, J=8.25 Hz, 1H), 6.90 (m, 1H), 6.78-6.71 (m, 3H), 1.45 (s, 3H), 1.23 (s, 1H), 0.99 (m, 2H), 0.80 (m, 2H); Mass (FAB) m/z 434 [M+H]$^+$ <Example 53> (E)-3-(3-(tert-butyl)-1-(3-chlorophenyl)-1H-pyrazol-5-yl)-N-(2-oxo-2,3-dihydro-1H-benzo[d]imidazol-4-yl)acrylamide

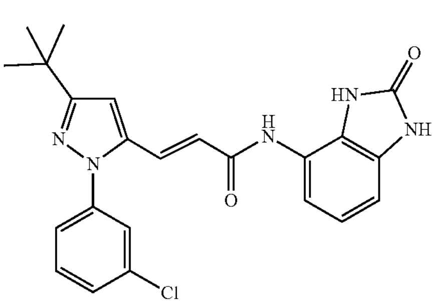 [SMILES: CC(C)(C)c1cc(/C=C/C(=O)Nc2cccc3[nH]c(=O)[nH]c23)n(-c2cccc(Cl)c2)n1]

Yellow solid, yield 88%; $^1$H NMR (300 MHz, DMSO-D6) δ 10.73 (s, 1H), 10.09 (s, 1H), 9.87, (s, 1H), 7.57-7.64 (m, 3H), 7.44-7.47 (m, 1H), 7.32 (d, J=15.4 Hz, 1H), 7.20 (d, J=8.0 Hz, 1H), 6.86-6.93 (m, 2H), 6.74-6.79 (m, 2H), 1.33 (s, 9H); Mass (FAB) m/z 436 [M+H]$^+$ <Example 54> (E)-3-(4-(3-chlorophenyl)-2-(trifluoromethyl)thiazol-5-yl)-N-(2-oxo-2,3-dihydro-1H-benzo[d]imidazol-4-yl)acrylamide

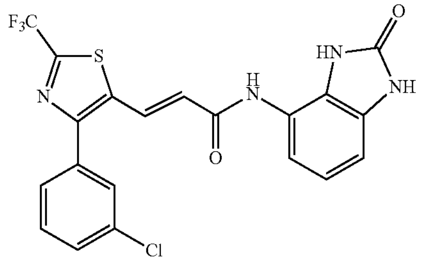 [SMILES: O=C(/C=C/c1sc(C(F)(F)F)nc1-c1cccc(Cl)c1)Nc1cccc2[nH]c(=O)[nH]c12]

Pale brown solid, yield 77%; $^1$H-NMR (400 MHz, DMSO) δ 10.70 (s, 1H), 10.08 (s, 1H), 10.02 (s, 1H), 7.66 (d, J=10.8 Hz, 1H), 7.59 (m, 4H), 7.12 (d, J=8.0 Hz, 1H), 6.88 (t, J=8.4 Hz, 1H), 6.80 (d, J=15.6 Hz, 1H), 6.74 (d, J=8.0 Hz, 1H); Mass (FAB) m/z 465 [M+H]$^+$ <Example 55> (E)-3-(4-(3-chlorophenyl)-2-isopropylthiazol-5-yl)-N-(2-oxo-2,3-dihydro-1H-benzo[d]imidazol-4-yl)acrylamide

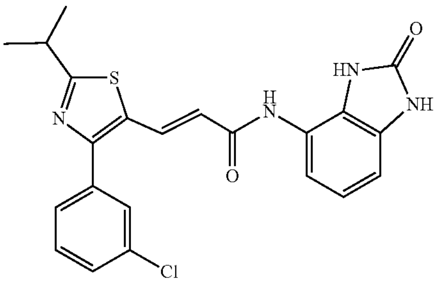 [SMILES: CC(C)c1nc(-c2cccc(Cl)c2)c(/C=C/C(=O)Nc2cccc3[nH]c(=O)[nH]c23)s1]

Pale yellow solid, yield 78%; $^1$H NMR (400 MHz, DMSO) δ 10.69 (s, 1H), 10.05 (s, 1H), 9.85 (s, 1H), 7.63 (d, J=15.2 Hz, 1H), 7.63 (s, 1H), 7.56-7.52 (m, 3H), 7.17 (d, J=8.4 Hz, 1H), 6.88 (t, J=8.0 Hz, 1H), 6.73 (d, J=7.6 Hz, 1H), 6.56 (d, J=15.6 Hz, 1H), 3.35 (m, 1H), 1.37 (d, J=6.8 Hz, 6H); Mass (FAB) m/z 439 [M+H]$^+$ <Example 56> (E)-3-(4-(3-chlorophenyl)-2-cyclopropylthiazol-5-yl)-N-(2-oxo-2,3-dihydro-1H-benzo[d]imidazol-4-yl)acrylamide

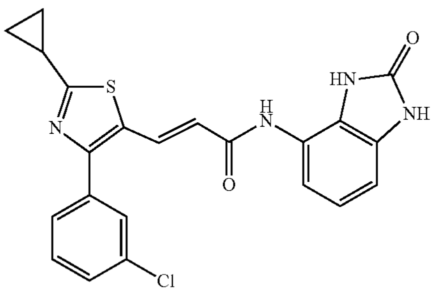 [SMILES: O=C(/C=C/c1sc(C2CC2)nc1-c1cccc(Cl)c1)Nc1cccc2[nH]c(=O)[nH]c12]

Pale yellow solid, yield 78%; $^1$H NMR (400 MHz, DMSO) δ10.69 (s, 1H), 10.05 (s, 1H), 9.84 (s, 1H), 7.61 (s, 1H), 7.60 (d, J=15.6 Hz, 1H), 7.56-7.53 (m, 3H), 7.17 (d, J=8.0 Hz, 1H), 6.88 (t, J=8.4 Hz, 1H), 6.73 (d, J=7.2 Hz, 1H), 6.50 (d, J=15.6 Hz, 1H), 1.21 (m, 3H), 1.10 (m, 2H); Mass (FAB) m/z 437[M+H]$^+$ <Example 57> (E)-3-(4-(3-chlorophenyl)-2-(1-methylcyclopropyl)thiazol-5-yl)-N-(2-oxo-2,3-dihydro-1H-benzo[d]imidazol-4-yl)acrylamide

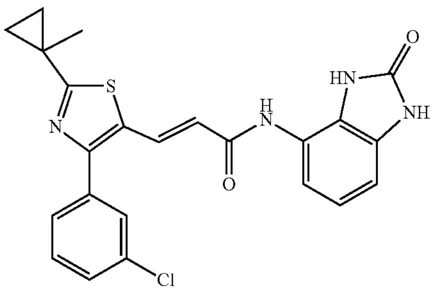 [SMILES: CC1(c2nc(-c3cccc(Cl)c3)c(/C=C/C(=O)Nc3cccc4[nH]c(=O)[nH]c34)s2)CC1]

Pale brown solid, yield 66%; $^1$H NMR (400 MHz, DMSO) δ 10.68 (s, 1H), 10.03 (s, 1H), 9.81 (s, 1H), 7.59 (m, 1H), 7.58 (d, J=15.2 Hz, 1H), 7.54-7.49 (m, 3H), 7.15 (d, J=8.4 Hz, 1H), 6.86 (t, J=8.0 Hz, 1H), 6.71 (d, J=7.2 Hz, 1H), 6.51 (d, J=15.2 Hz, 1H), 1.55 (s, 3H), 1.31 (m, 2H), 1.08 (m, 2H); Mass (FAB) m/z 451 [M+H]$^+$ <Example 58> (E)-3-(2-(tert-butyl)-4-(3-chlorophenyl)thiazol-5-yl)-N-(2-oxo-2,3-dihydro-1H-benzo[d]imidazol-4-yl)acrylamide

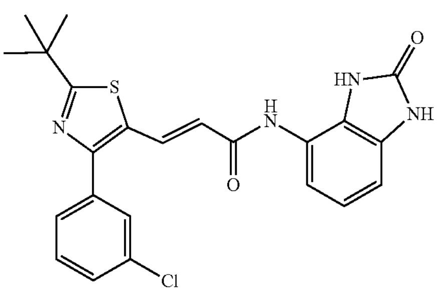 [SMILES: CC(C)(C)c1nc(-c2cccc(Cl)c2)c(/C=C/C(=O)Nc2cccc3[nH]c(=O)[nH]c23)s1]

Pale brown solid, yield 66%; $^1$H NMR (400 MHz, DMSO) δ 10.66 (s, 1H), 10.01 (s, 1H), 9.82 (s, 1H), 7.67 (d, J=15.2 Hz, 1H), 7.66 (m, 1H), 7.58 (m, 3H), 7.21 (d, J=8.12 Hz, 1H), 6.91 (t, J=7.96 Hz, 1H), 6.75 (d, J=7.72 Hz, 1H), 6.60 (d, J=15.2 Hz, 1H), 1.46 (s, 9H); Mass (FAB) m/z 453 [M+H]$^+$ <Example 59> 3-(2-isobutoxy-6-(trifluoromethyl)pyridin-3-yl)-N-(2-oxo-2,3-dihydro-1H-benzo[d]imidazol-4-yl)propaneamide

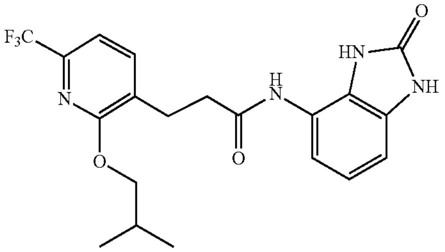 [SMILES: CC(C)COc1nc(C(F)(F)F)ccc1CCC(=O)Nc1cccc2[nH]c(=O)[nH]c12]

Pale yellow solid, yield 86%; $^1$H NMR (500 MHz, CDCl3) δ 9.14 (s, 1H), 8.16 (s, 1H), 7.58 (d, J=7.35 Hz, 1H), 7.27 (s, 1H), 7.16 (d, J=7.40 Hz, 1H), 6.93 (t, J=7.90 Hz, 1H), 6.81 (d, J=7.75 Hz, 1H), 6.58 (d, J=8.05 Hz, 1H), 4.16 (d, J=6.45 Hz, 2H), 3.05 (t, J=7.25 Hz, 2H), 2.74 (t, J=7.25 Hz, 2H), 2.11 (p, J=6.70 Hz, 1H), 1.03 (d, J=6.65 Hz, 6H); Mass (FAB) m/z 423 [M+H]$^+$ <Example 60> 3-(2-(cyclopropylmethoxy)-6-(trifluoromethyl)pyridin-3-yl)-N-(2-oxo-2,3-dihydro-1H-benzo[d]imidazol-4-yl)propaneamide

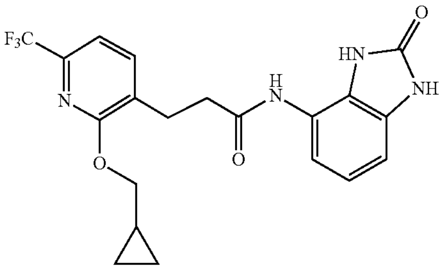 [SMILES: O=C(CCc1ccc(C(F)(F)F)nc1OCC1CC1)Nc1cccc2[nH]c(=O)[nH]c12]

White solid, yield 77%; $^1$H NMR (300 MHz, DMSO) δ 10.66 (s, 1H), 10.08 (s, 1H), 9.53 (s, 1H), 7.80 (d, J=7.50 Hz, 1H), 7.41 (d, J=6.00 Hz, 1H), 7.07 (d, J=8.25 Hz, 1H), 6.87 (t, J=7.86 Hz, 1H), 6.72 (d, J=7.86 Hz, 1H), 4.20 (d, J=6.96 Hz, 2H), 2.96 (t, J=7.14 Hz, 2H), 2.70 (t, J=7.50 Hz, 2H), 1.28 (m, 1H), 0.55 (q, J=5.70 Hz, 2H), 0.40 (q, J=5.70 Hz, 2H); Mass (FAB) m/z 421 [M+H]$^+$ <Example 61> 2-(2-isobutoxy-6-(trifluoromethyl)pyridin-3-yl)-N-(2-oxo-2,3-dihydro-1H-benzo[d]imidazol-4-yl)cyclopropan-1-carboxamide

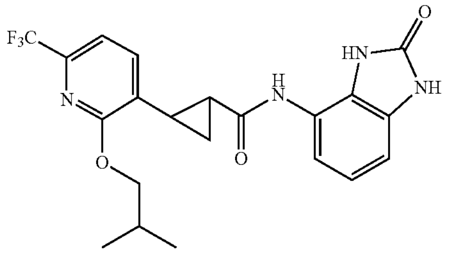 [SMILES: CC(C)COc1nc(C(F)(F)F)ccc1C1CC1C(=O)Nc1cccc2[nH]c(=O)[nH]c12]

Pale yellow solid, yield 72%; $^{1}$H NMR (500 MHz, $CDCl_3$) δ 9.14 (s, 1H), 8.16 (s, 1H), 7.58 (d, J=7.35 Hz, 1H), 7.27 (s, 1H), 7.16 (d, J=7.40 Hz, 1H), 6.93 (t, J=7.90 Hz, 1H), 6.81 (d, J=7.75 Hz, 1H), 6.58 (d, J=8.05 Hz, 1H), 4.16 (d, J=6.45 Hz, 2H), 3.11 (s, 1H), 2.89 (s, 1H), 2.11 (p, J=6.70 Hz, 1H), 1.23 (m, 2H), 1.03 (d, J=6.65 Hz, 6H), 0.89 (m, 1H); Mass (FAB) m/z 435 $[M+H]^+$ <Example 62> 2-(2-(cyclopropylmethoxy)-6-(trifluoromethyl)pyridin-3-yl)-N-(2-oxo-2,3-dihydro-1H-benzo[d]imidazol-4-yl)cyclopropane-1-carboxamide

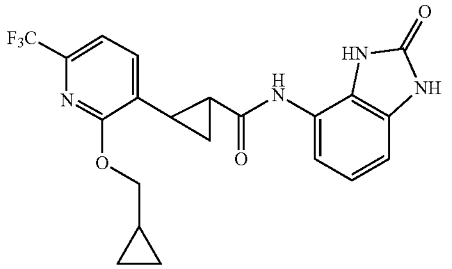 [SMILES: O=C(Nc1cccc2[nH]c(=O)[nH]c12)C1CC1c1ccc(C(F)(F)F)nc1OCC1CC1]

White solid, yield 65%; $^{1}$H NMR (300 MHz, DMSO) δ 10.66 (s, 1H), 10.08 (s, 1H), 9.53 (s, 1H), 7.80 (d, J=7.50 Hz, 1H), 7.41 (d, J=6.00 Hz, 1H), 7.07 (d, J=8.25 Hz, 1H), 6.87 (t, J=7.86 Hz, 1H), 6.72 (d, J=7.86 Hz, 1H), 4.20 (d, J=6.96 Hz, 2H), 2.96 (t, J=7.14 Hz, 2H), 2.70 (t, J=7.50 Hz, 2H), 1.28 (m, 3H), 0.80 (m, 1H), 0.55 (q, J=5.70 Hz, 2H), 0.40 (q, J=5.70 Hz, 2H); Mass (FAB) m/z 433 $[M+H]^+$ <Example 63> 2-(1-(3-chlorophenyl)-3-(trifluoromethyl)-1H-pyrazol-5-yl)-N-(2-oxo-2,3-dihydro-1H-benzo[d]imidazol-4-yl)cyclopropane-1-carboxamide

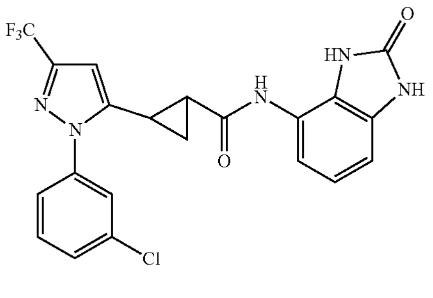 [SMILES: O=C(Nc1cccc2[nH]c(=O)[nH]c12)C1CC1c1cc(C(F)(F)F)nn1-c1cccc(Cl)c1]

White solid, yield 78%; $^{1}$H NMR (400 MHz, DMSO) δ 10.67 (s, 1H), 9.95 (s, 1H), 9.85 (s, 1H), 7.75 (s, 1H), 7.66-7.64 (t, J=5.88 Hz, 1H), 7.57 (s, 2H), 7.07 (d, J=6.52 Hz, 1H), 6.90 (d, 1H), 6.87 (s, 1H), 6.74 (d, J=6.16 Hz, 1H), 2.35 (m, 1H), 2.18 (m, 1H), 1.53 (t, J=5.92 Hz, 2H), 1.23 (s, 2H), 0.80 (m, 1H); Mass (FAB) m/z 462 $[M+H]^+$ <Example 64> 2-(1-(3-chlorophenyl)-3-(1,1-difluoroethyl)-1H-pyrazol-5-yl)-N-(2-oxo-2,3-dihydro-1H-benzo[d]imidazol-4-yl)cyclopropane-1-carboxamide

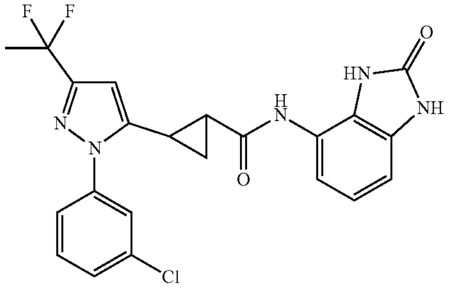 [SMILES: CC(F)(F)c1cc(C2CC2C(=O)Nc2cccc3[nH]c(=O)[nH]c23)n(-c2cccc(Cl)c2)n1]

Yellow solid, yield 65%; $^{1}$H NMR (300 MHz, DMSO) δ 10.67 (s, 1H), 9.95 (s, 1H), 9.87 (s, 1H), 7.63 (s, 1H), 7.56 (m, 1H), 7.46 (t, J=8.22 Hz, 1H), 7.41 (s, 1H), 7.10 (d, J=7.89 Hz, 1H), 6.88 (t, J=7.68 Hz, 1H), 6.73 (d, J=8.07 Hz, 1H), 6.05 (s, 1H), 1.23 (m, 1H), 0.91 (m, 1H), 0.67 (m, 3H); Mass (FAB) m/z 458 $[M+H]^+$ <Example 65> 2-(1-(3-chlorophonyl)-3-isopropyl-1H-pyrazol-5-yl)-N-(2-oxo-2,3-dihydro-1H-benzo[d]imidazol-4-yl)cyclopropane-1-carboxamide

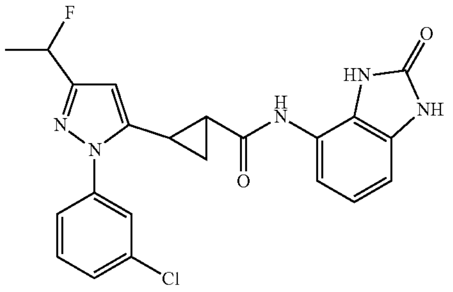 [SMILES: CC(F)c1cc(C2CC2C(=O)Nc2cccc3[nH]c(=O)[nH]c23)n(-c2cccc(Cl)c2)n1]

Pale brown solid, yield 60%; $^{1}$H NMR (300 MHz, DMSO) δ 10.67 (s, 1H), 9.98 (s, 1H), 9.89 (s, 1H), 7.64 (s, 1H), 7.59 (d, J=7.68 Hz, 1H), 7.48 (t, J=8.25 Hz, 1H), 7.42 (m, 1H), 7.16 (d, J=8.04 Hz, 1H), 6.88 (t, J=7.53 Hz, 1H), 6.72 (d, J=7.62 Hz, 1H), 6.21 (s, 1H), 2.30 (m, 1H), 2.19 (m, 1H), 1.74 (s, 2H), 1.51 (m, 1H), 1.23 (d, J=6.78 Hz, 6H); Mass (FAB) m/z 436 $[M+H]^+$ <Example 66> 2-(1-(3-chlorophenyl)-3-cyclopropyl-1H-pyrazol-5-yl)-N-(2-oxo-2,3-dihydro-1H-benzo[d]imidazol-4-yl)cyclopropane-1-carboxamide

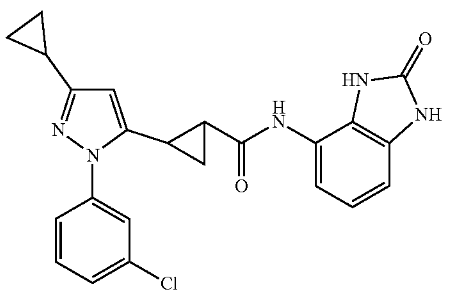 [SMILES: O=C(Nc1cccc2[nH]c(=O)[nH]c12)C1CC1c1cc(C2CC2)nn1-c1cccc(Cl)c1]

Yellow solid, yield 82%; $^{1}$H NMR (300 MHz, DMSO) δ 10.67 (s, 1H), 9.98 (s, 1H), 9.89 (s, 1H), 7.64 (s, 1H), 7.57 (m, 2H), 7.49 (t, J=8.25 Hz, 2H), 7.42 (m, 2H), 7.10 (d, J=7.86 Hz, 1H), 6.88 (t, J=7.68 Hz, 1H), 6.73 (d, J=7.68 Hz, 1H), 6.05 (s, 1H), 2.32 (m, 1H), 2.08 (m, 1H), 1.95 (m, 2H), 1.51 (m, 1H), 0.89 (m, 2H), 0.67 (m, 2H); Mass (FAB) m/z 434 [M+H]° C.

<Example 67> 2-(1-(3-chlorophenyl)-3-(1-methylcyclopropyl)-1H-pyrazol-5-yl)-N-(2-oxo-2,3-dihydro-1H-benzo[d]imidazol-4-yl)cyclopropane-1-carboxamide

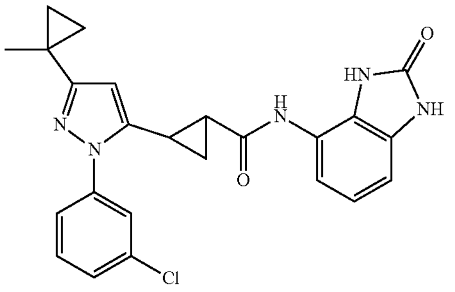 [SMILES: CC1(c2cc(C3CC3C(=O)Nc3cccc4[nH]c(=O)[nH]c34)n(-c3cccc(Cl)c3)n2)CC1]

Yellow solid, yield 73%; $^{1}$H NMR (300 MHz, DMSO) δ 10.68 (s, 1H), 9.96 (s, 1H), 9.87 (s, 1H), 7.64 (s, 1H), 7.57 (m, 1H), 7.49 (t, J=8.25 Hz, 1H), 7.42 (m, 1H), 7.10 (d, J=7.86 Hz, 1H), 6.88 (t, J=7.68 Hz, 1H), 6.73 (d, J=7.68 Hz, 1H), 6.12 (s, 1H), 1.40 (s, 3H), 0.91 (s, 2H), 0.74 (s, 2H); Mass (FAB) m/z 448 [M+H]$^{+}$ <Example 68> 2-(3-(tert-butyl)-1-(3-chlorophenyl)-1H-pyrazol-5-yl)-N-(2-oxo-2,3-dihydro-1H-benzo[d]imidazol-4-yl)cyclopropane-1-carboxamide

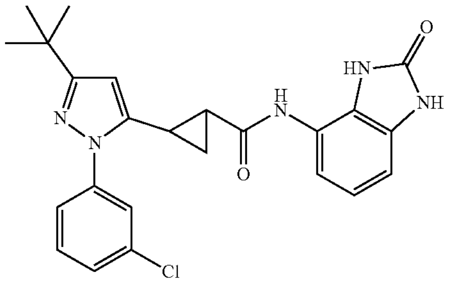 [SMILES: CC(C)(C)c1cc(C2CC2C(=O)Nc2cccc3[nH]c(=O)[nH]c23)n(-c2cccc(Cl)c2)n1]

Yellow solid, yield 82%; $^{1}$H NMR (400 MHz, DMSO) δ 10.67 (s, 1H), 9.93 (s, 1H), 9.85 (s, 1H), 7.64 (s, 1H), 7.60 (d, J=6.92 Hz, 1H), 7.51 (t, J=8.00 Hz, 1H), 7.44 (d, J=6.92 Hz, 1H), 7.11 (d, J=8.08 Hz, 1H), 6.89 (t, J=7.96 Hz, 1H), 6.74 (d, J=7.76 Hz, 1H), 6.22 (s, 1H), 2.32 (m, 1H), 2.13 (m, 1H), 1.53 (m, 1H), 1.42 (m, 1H), 1.27 (s, 9H); Mass (FAB) m/z 450 [M+H]$^{+}$ The chemical formulas of the compounds prepared in Examples 1-68 are summarized and shown in Table 1 below.

TABLE 1

| Example | Chemical Formula |
|---|---|
| 1 | 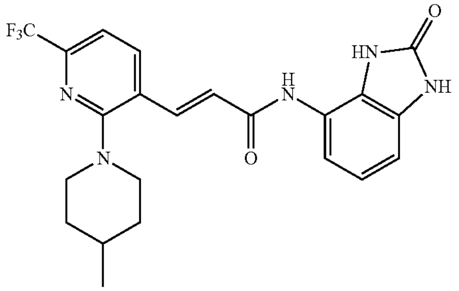 [SMILES: CC1CCN(c2nc(C(F)(F)F)ccc2/C=C/C(=O)Nc2cccc3[nH]c(=O)[nH]c23)CC1] |
| 2 | 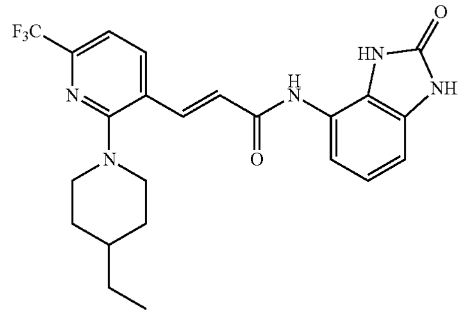 [SMILES: CCC1CCN(c2nc(C(F)(F)F)ccc2/C=C/C(=O)Nc2cccc3[nH]c(=O)[nH]c23)CC1] |
| 3 | 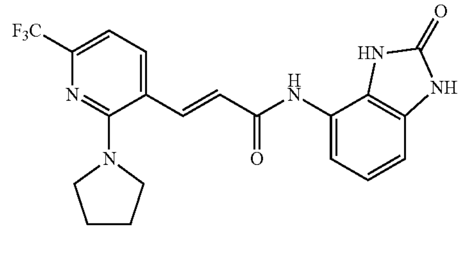 |

TABLE 1-continued
| Example | Chemical Formula |
|---|---|
| 4 | 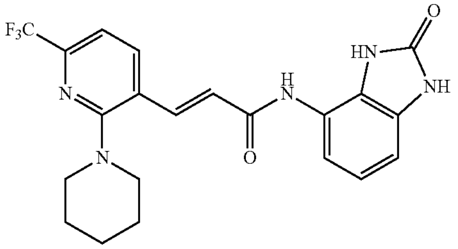 [SMILES: O=C(/C=C/c1ccc(C(F)(F)F)nc1N1CCCCC1)Nc1cccc2[nH]c(=O)[nH]c12] |
| 5 | 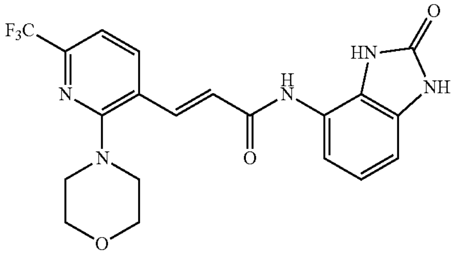 [SMILES: O=C(/C=C/c1ccc(C(F)(F)F)nc1N1CCOCC1)Nc1cccc2[nH]c(=O)[nH]c12] |
| 6 | 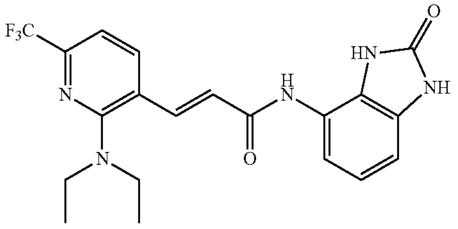 [SMILES: CCN(CC)c1nc(C(F)(F)F)ccc1/C=C/C(=O)Nc1cccc2[nH]c(=O)[nH]c12] |
| 7 | 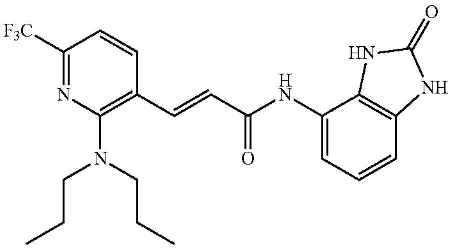 [SMILES: CCCN(CCC)c1nc(C(F)(F)F)ccc1/C=C/C(=O)Nc1cccc2[nH]c(=O)[nH]c12] |
| 8 | 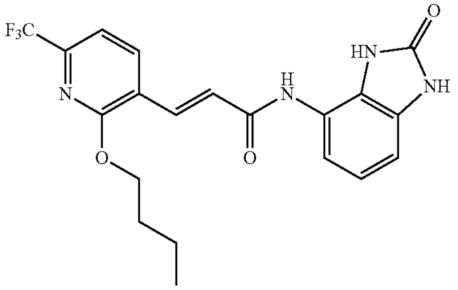 [SMILES: CCCCOc1nc(C(F)(F)F)ccc1/C=C/C(=O)Nc1cccc2[nH]c(=O)[nH]c12] |
| 9 | 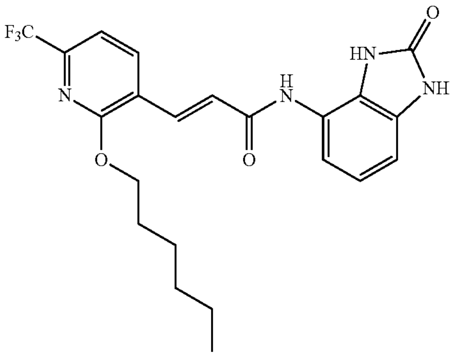 [SMILES: CCCCCCOc1nc(C(F)(F)F)ccc1/C=C/C(=O)Nc1cccc2[nH]c(=O)[nH]c12] |
| 10 | 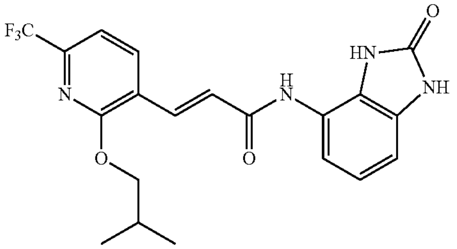 |
| 11 | 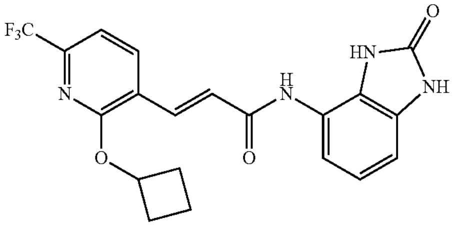 [SMILES: O=C(/C=C/c1ccc(C(F)(F)F)nc1OC1CCC1)Nc1cccc2[nH]c(=O)[nH]c12] |
| 12 | 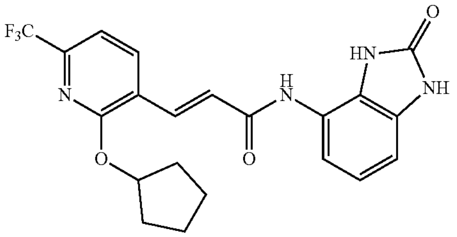 [SMILES: O=C(/C=C/c1ccc(C(F)(F)F)nc1OC1CCCC1)Nc1cccc2[nH]c(=O)[nH]c12] |
| 13 | 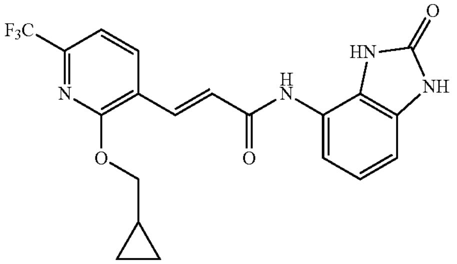 |

TABLE 1-continued
| Example | Chemical Formula |
| --- | --- |
| 14 | 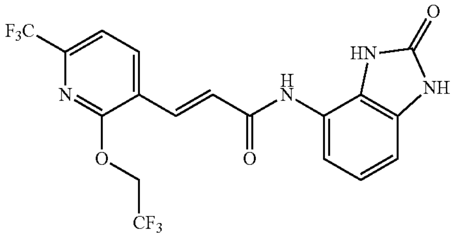 [SMILES: O=C(/C=C/c1ccc(C(F)(F)F)nc1OCC(F)(F)F)Nc1cccc2[nH]c(=O)[nH]c12] |
| 15 | 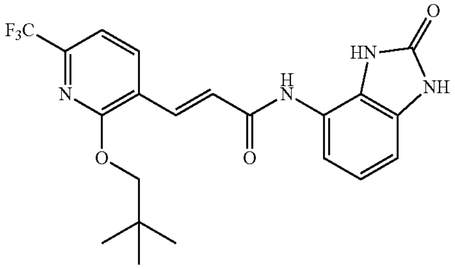 [SMILES: CC(C)(C)COc1nc(C(F)(F)F)ccc1/C=C/C(=O)Nc1cccc2[nH]c(=O)[nH]c12] |
| 16 | 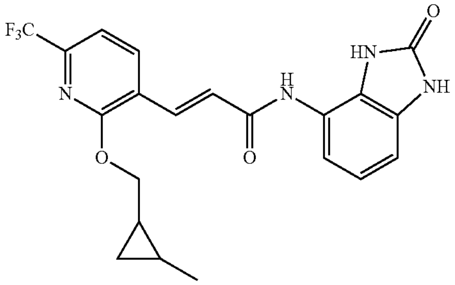 [SMILES: CC1CC1COc1nc(C(F)(F)F)ccc1/C=C/C(=O)Nc1cccc2[nH]c(=O)[nH]c12] |
| 17 | 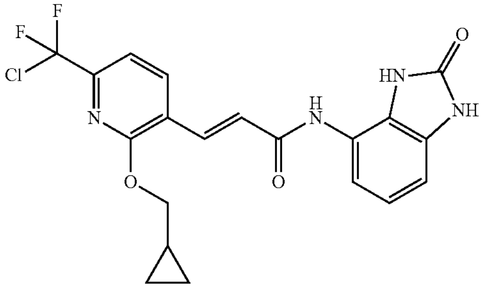 [SMILES: O=C(/C=C/c1ccc(C(F)(F)Cl)nc1OCC1CC1)Nc1cccc2[nH]c(=O)[nH]c12] |
| 18 | 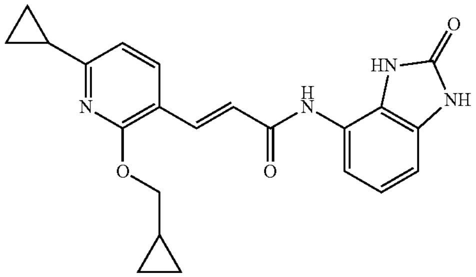 [SMILES: O=C(/C=C/c1ccc(C2CC2)nc1OCC1CC1)Nc1cccc2[nH]c(=O)[nH]c12] |
TABLE 1-continued
| Example | Chemical Formula |
| --- | --- |
| 19 | 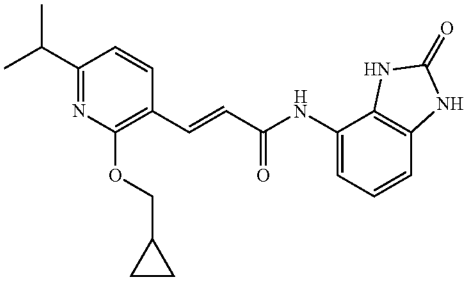 [SMILES: CC(C)c1ccc(/C=C/C(=O)Nc2cccc3[nH]c(=O)[nH]c23)c(OCC2CC2)n1] |
| 20 | 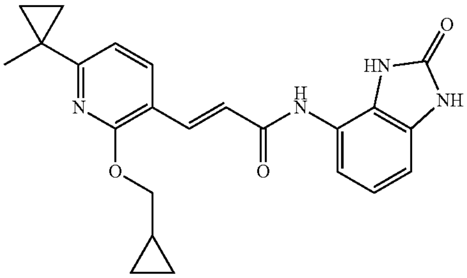 [SMILES: CC1(c2ccc(/C=C/C(=O)Nc3cccc4[nH]c(=O)[nH]c34)c(OCC3CC3)n2)CC1] |
| 21 | 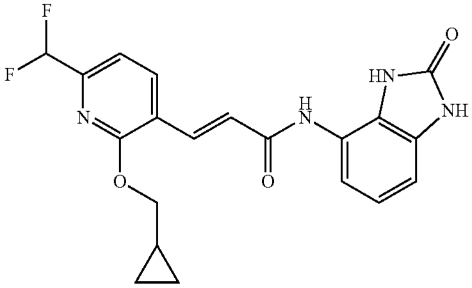 [SMILES: O=C(/C=C/c1ccc(C(F)F)nc1OCC1CC1)Nc1cccc2[nH]c(=O)[nH]c12] |
| 22 | 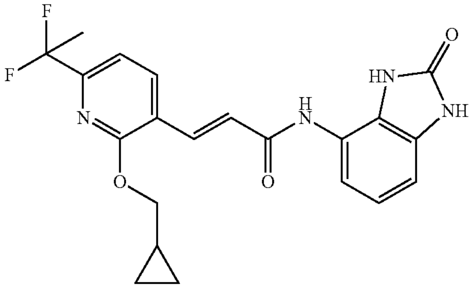 [SMILES: CC(F)(F)c1ccc(/C=C/C(=O)Nc2cccc3[nH]c(=O)[nH]c23)c(OCC2CC2)n1] |
| 23 | 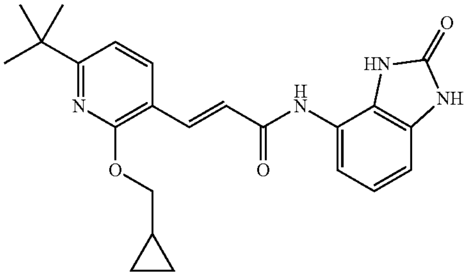 [SMILES: CC(C)(C)c1ccc(/C=C/C(=O)Nc2cccc3[nH]c(=O)[nH]c23)c(OCC2CC2)n1] |

TABLE 1-continued
| Example | Chemical Formula |
|---|---|
| 24 | 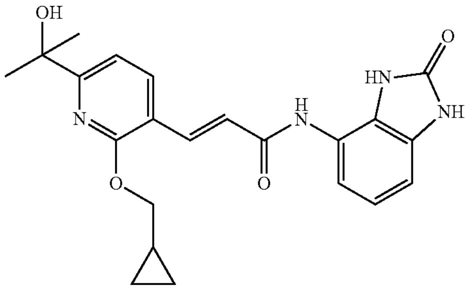 [SMILES: CC(C)(O)c1ccc(/C=C/C(=O)Nc2cccc3[nH]c(=O)[nH]c23)c(OCC2CC2)n1] |
| 25 | 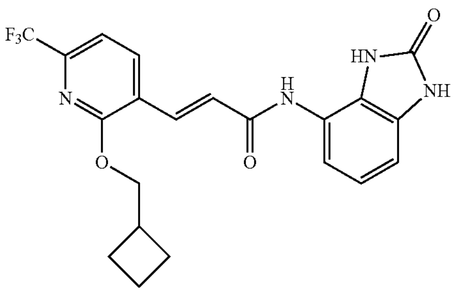 [SMILES: O=C(/C=C/c1ccc(C(F)(F)F)nc1OCC1CCC1)Nc1cccc2[nH]c(=O)[nH]c12] |
| 26 | 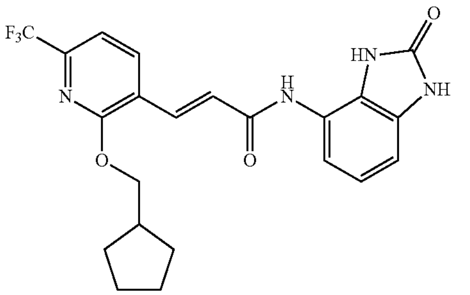 [SMILES: O=C(/C=C/c1ccc(C(F)(F)F)nc1OCC1CCCC1)Nc1cccc2[nH]c(=O)[nH]c12] |
| 27 | 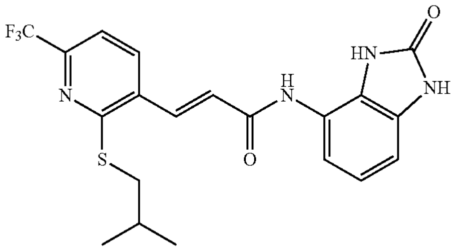 [SMILES: CC(C)CSc1nc(C(F)(F)F)ccc1/C=C/C(=O)Nc1cccc2[nH]c(=O)[nH]c12] |
| 28 | 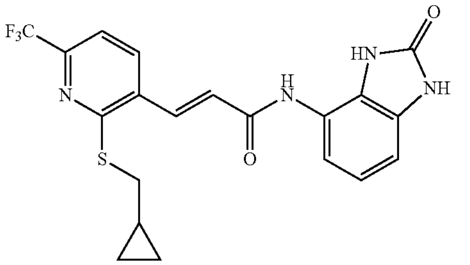 |
TABLE 1-continued
| Example | Chemical Formula |
|---|---|
| 29 | 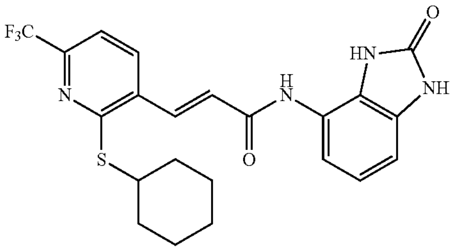 [SMILES: O=C(/C=C/c1ccc(C(F)(F)F)nc1SC1CCCCC1)Nc1cccc2[nH]c(=O)[nH]c12] |
| 30 | 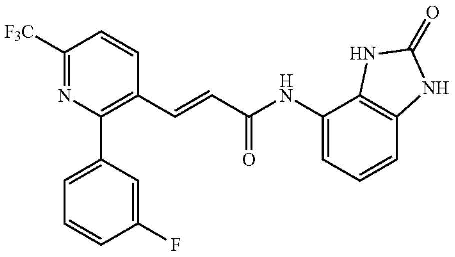 |
| 31 | 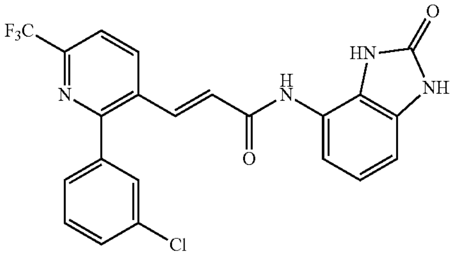 |
| 32 | 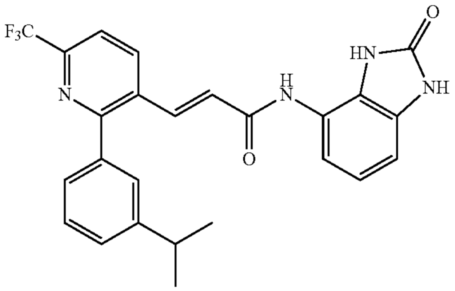 [SMILES: CC(C)c1cccc(-c2nc(C(F)(F)F)ccc2/C=C/C(=O)Nc2cccc3[nH]c(=O)[nH]c23)c1] |
| 33 | 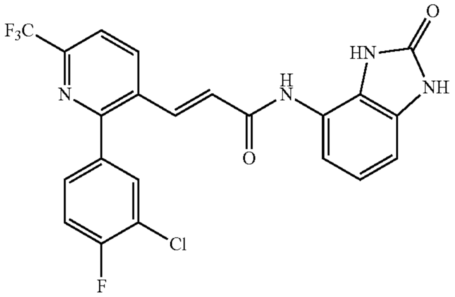 [SMILES: O=C(/C=C/c1ccc(C(F)(F)F)nc1-c1ccc(F)c(Cl)c1)Nc1cccc2[nH]c(=O)[nH]c12] |

TABLE 1-continued
| Example | Chemical Formula |
|---|---|
| 34 | 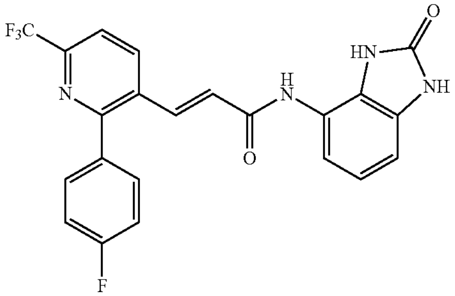 [SMILES: O=C(/C=C/c1ccc(C(F)(F)F)nc1-c1ccc(F)cc1)Nc1cccc2[nH]c(=O)[nH]c12] |
| 35 | 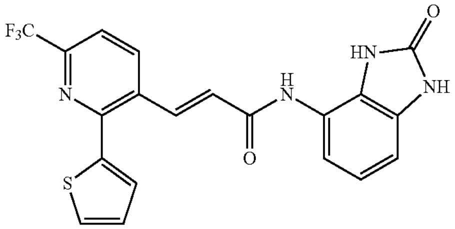 |
| 36 | 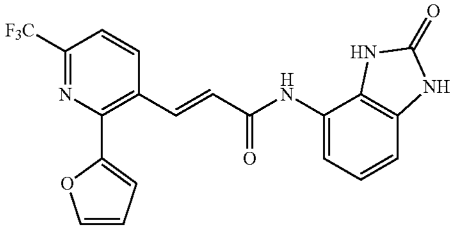 |
| 37 | 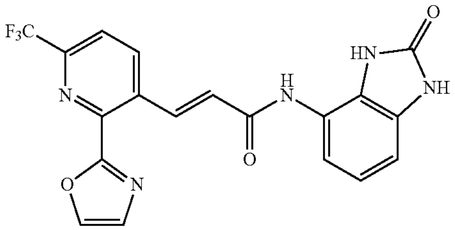 [SMILES: O=C(/C=C/c1ccc(C(F)(F)F)nc1-c1ncco1)Nc1cccc2[nH]c(=O)[nH]c12] |
| 38 | 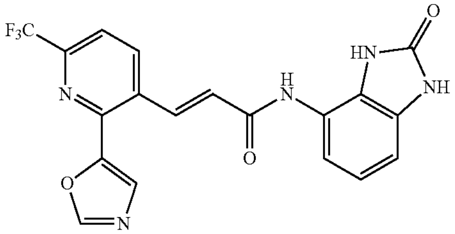 [SMILES: O=C(/C=C/c1ccc(C(F)(F)F)nc1-c1cnco1)Nc1cccc2[nH]c(=O)[nH]c12] |
| 39 | 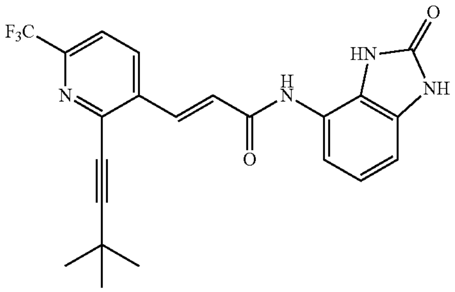 [SMILES: CC(C)(C)C#Cc1nc(C(F)(F)F)ccc1/C=C/C(=O)Nc1cccc2[nH]c(=O)[nH]c12] |
TABLE 1-continued
| Example | Chemical Formula |
|---|---|
| 40 | 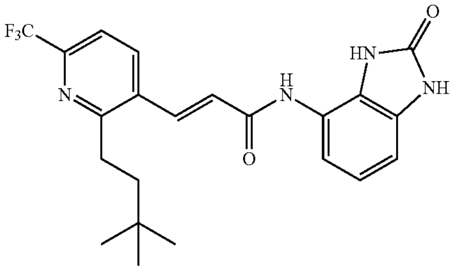 [SMILES: CC(C)(C)CCc1nc(C(F)(F)F)ccc1/C=C/C(=O)Nc1cccc2[nH]c(=O)[nH]c12] |
| 41 | 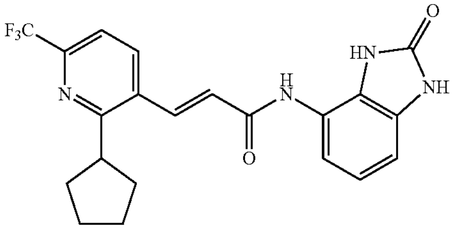 [SMILES: O=C(/C=C/c1ccc(C(F)(F)F)nc1C1CCCC1)Nc1cccc2[nH]c(=O)[nH]c12] |
| 42 | 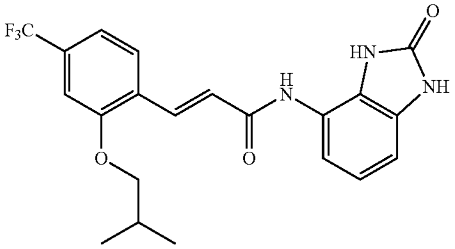 [SMILES: CC(C)COc1cc(C(F)(F)F)ccc1/C=C/C(=O)Nc1cccc2[nH]c(=O)[nH]c12] |
| 43 | 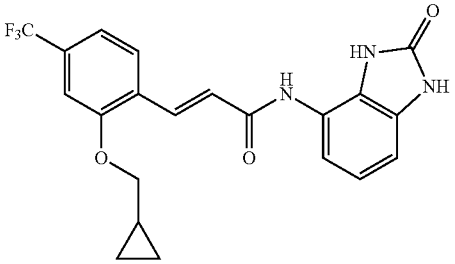 |
| 44 | 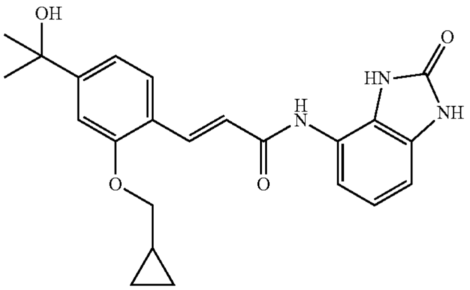 [SMILES: CC(C)(O)c1ccc(/C=C/C(=O)Nc2cccc3[nH]c(=O)[nH]c23)c(OCC2CC2)c1] |

TABLE 1-continued
| Example | Chemical Formula |
| --- | --- |
| 45 | 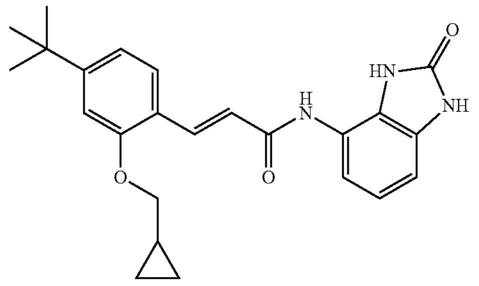 [SMILES: CC(C)(C)c1ccc(/C=C/C(=O)Nc2cccc3[nH]c(=O)[nH]c23)c(OCC2CC2)c1] |
| 46 | 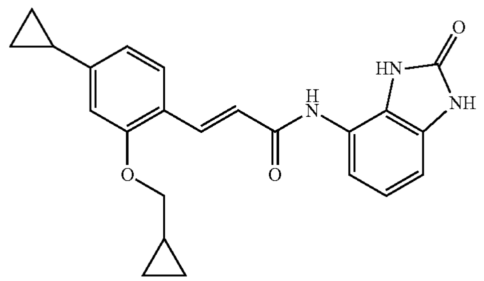 [SMILES: O=C(/C=C/c1ccc(C2CC2)cc1OCC1CC1)Nc1cccc2[nH]c(=O)[nH]c12] |
| 47 | 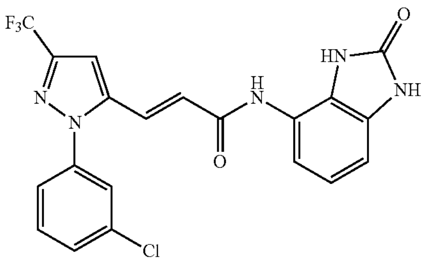 [SMILES: O=C(/C=C/c1cc(C(F)(F)F)nn1-c1cccc(Cl)c1)Nc1cccc2[nH]c(=O)[nH]c12] |
| 48 | 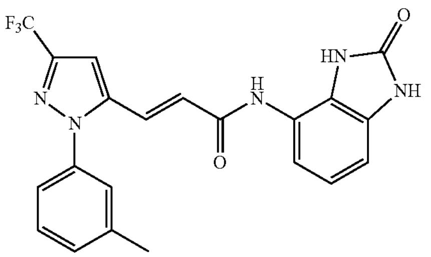 [SMILES: Cc1cccc(-n2nc(C(F)(F)F)cc2/C=C/C(=O)Nc2cccc3[nH]c(=O)[nH]c23)c1] |
| 49 | 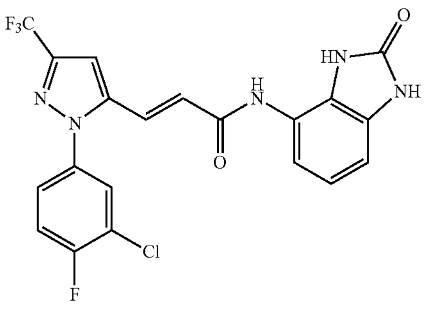 [SMILES: O=C(/C=C/c1cc(C(F)(F)F)nn1-c1ccc(F)c(Cl)c1)Nc1cccc2[nH]c(=O)[nH]c12] |
| 50 | 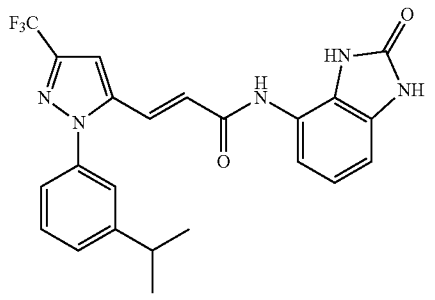 [SMILES: CC(C)c1cccc(-n2nc(C(F)(F)F)cc2/C=C/C(=O)Nc2cccc3[nH]c(=O)[nH]c23)c1] |
| 51 | 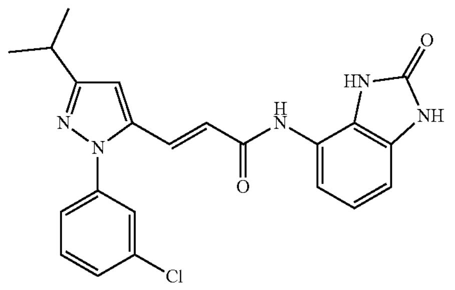 [SMILES: CC(C)c1cc(/C=C/C(=O)Nc2cccc3[nH]c(=O)[nH]c23)n(-c2cccc(Cl)c2)n1] |
| 52 | 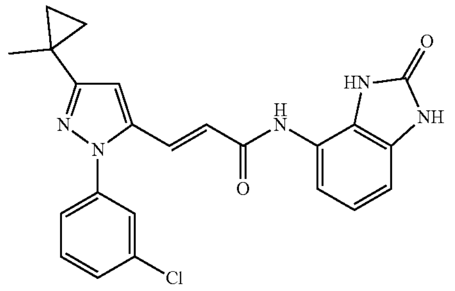 [SMILES: CC1(c2cc(/C=C/C(=O)Nc3cccc4[nH]c(=O)[nH]c34)n(-c3cccc(Cl)c3)n2)CC1] |
| 53 | 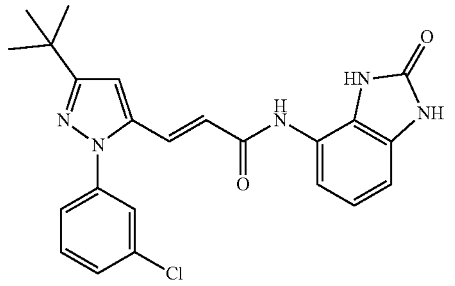 [SMILES: CC(C)(C)c1cc(/C=C/C(=O)Nc2cccc3[nH]c(=O)[nH]c23)n(-c2cccc(Cl)c2)n1] |
| 54 | 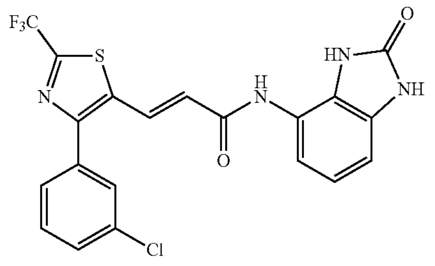 [SMILES: O=C(/C=C/c1sc(C(F)(F)F)nc1-c1cccc(Cl)c1)Nc1cccc2[nH]c(=O)[nH]c12] |

TABLE 1-continued
| Example | Chemical Formula |
|---|---|
| 55 | 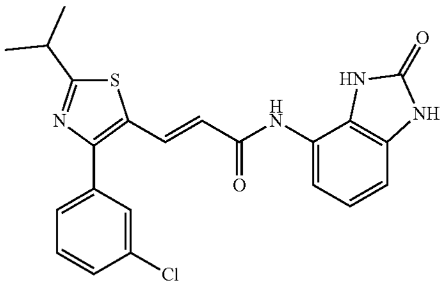 [SMILES: CC(C)c1nc(-c2cccc(Cl)c2)c(/C=C/C(=O)Nc2cccc3[nH]c(=O)[nH]c23)s1] |
| 56 | 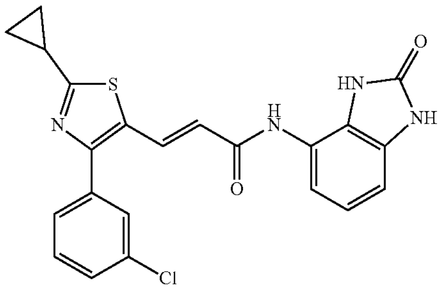 [SMILES: O=C(/C=C/c1sc(C2CC2)nc1-c1cccc(Cl)c1)Nc1cccc2[nH]c(=O)[nH]c12] |
| 57 | 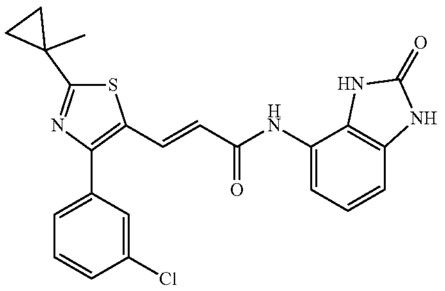 [SMILES: CC1(c2nc(-c3cccc(Cl)c3)c(/C=C/C(=O)Nc3cccc4[nH]c(=O)[nH]c34)s2)CC1] |
| 58 | 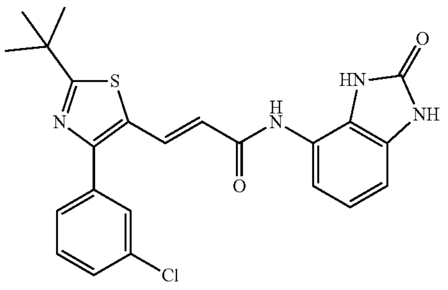 [SMILES: CC(C)(C)c1nc(-c2cccc(Cl)c2)c(/C=C/C(=O)Nc2cccc3[nH]c(=O)[nH]c23)s1] |
| 59 | 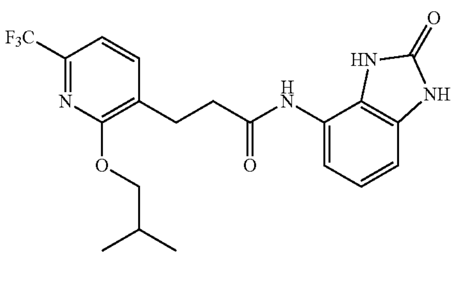 [SMILES: CC(C)COc1nc(C(F)(F)F)ccc1CCC(=O)Nc1cccc2[nH]c(=O)[nH]c12] |
TABLE 1-continued
| Example | Chemical Formula |
|---|---|
| 60 | 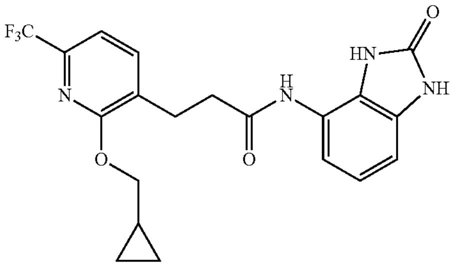 [SMILES: O=C(CCc1ccc(C(F)(F)F)nc1OCC1CC1)Nc1cccc2[nH]c(=O)[nH]c12] |
| 61 | 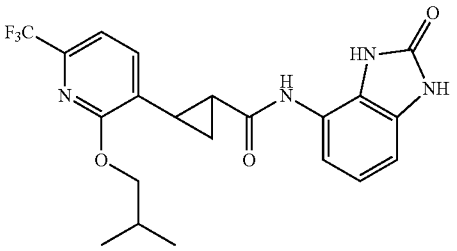 [SMILES: CC(C)COc1nc(C(F)(F)F)ccc1C1CC1C(=O)Nc1cccc2[nH]c(=O)[nH]c12] |
| 62 | 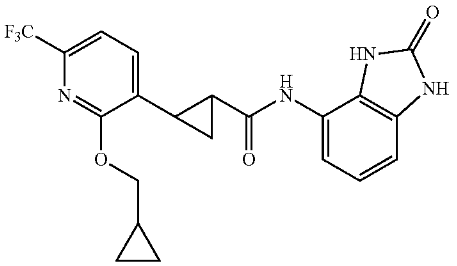 [SMILES: O=C(Nc1cccc2[nH]c(=O)[nH]c12)C1CC1c1ccc(C(F)(F)F)nc1OCC1CC1] |
| 63 | 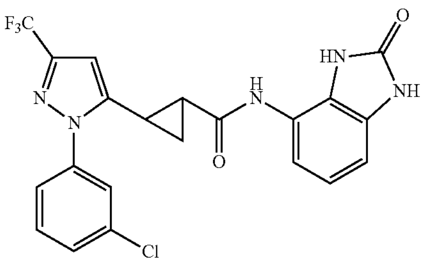 [SMILES: O=C(Nc1cccc2[nH]c(=O)[nH]c12)C1CC1c1cc(C(F)(F)F)nn1-c1cccc(Cl)c1] |
| 64 | 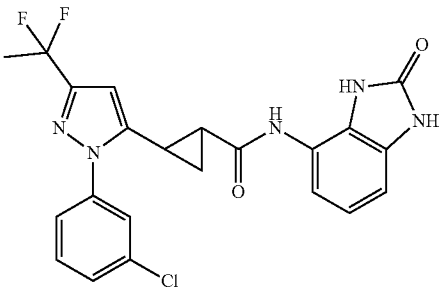 [SMILES: CC(F)(F)c1cc(C2CC2C(=O)Nc2cccc3[nH]c(=O)[nH]c23)n(-c2cccc(Cl)c2)n1] |

TABLE 1-continued

| Example | Chemical Formula |
| --- | --- |
| 65 | 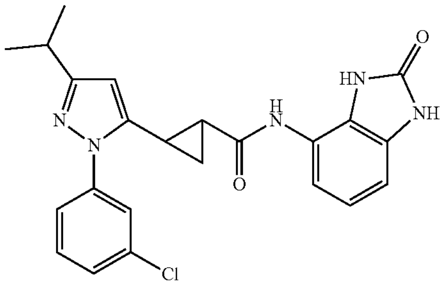 [SMILES: CC(C)c1cc(C2CC2C(=O)Nc2cccc3[nH]c(=O)[nH]c23)n(-c2cccc(Cl)c2)n1] |
| 66 | 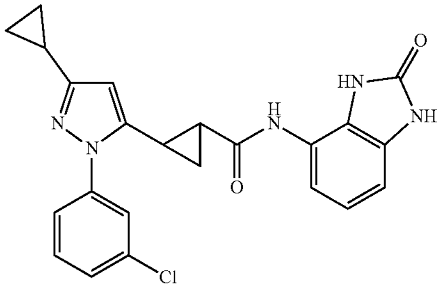 [SMILES: O=C(Nc1cccc2[nH]c(=O)[nH]c12)C1CC1c1cc(C2CC2)nn1-c1cccc(Cl)c1] |
| 67 | 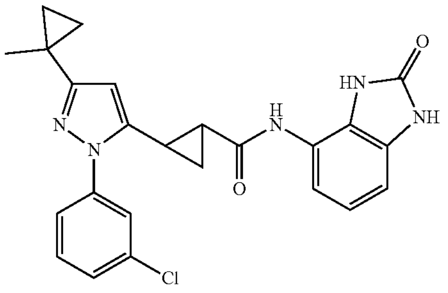 [SMILES: CC1(c2cc(C3CC3C(=O)Nc3cccc4[nH]c(=O)[nH]c34)n(-c3cccc(Cl)c3)n2)CC1] |
| 68 | 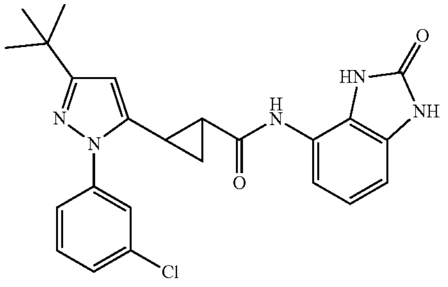 [SMILES: CC(C)(C)c1cc(C2CC2C(=O)Nc2cccc3[nH]c(=O)[nH]c23)n(-c2cccc(Cl)c2)n1] |

<Comparative Example 1> Preparation of 1-(2-oxo-1,3-dihydrobenzimidazol-4-yl)-3-[[2-pyrrolidin-1-yl-6-(trifluoromethyl)-3-pyridyl]methyl]urea

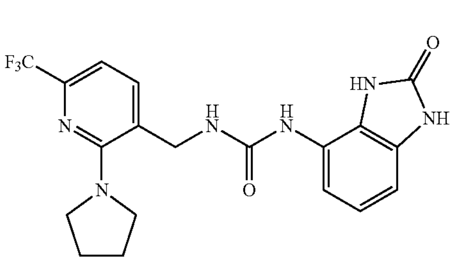 [SMILES: O=C(NCc1ccc(C(F)(F)F)nc1N1CCCC1)Nc1cccc2[nH]c(=O)[nH]c12]

The compound of Example 39 disclosed in Korean Patent Publication No. 10-2013-0065634 (WO 2011/120604 A1) was prepared as the compound of Comparative Example 1.

<Comparative Example 2> Preparation of 1-[[2-isopropoxy-6-(trifluoromethyl)-3-pyridyl]methyl]-3-(2-oxo-1,3-dihydrobenzimidazol-4-yl)urea

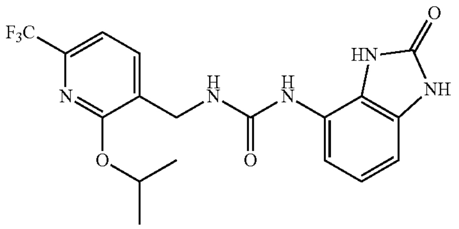 [SMILES: CC(C)Oc1nc(C(F)(F)F)ccc1CNC(=O)Nc1cccc2[nH]c(=O)[nH]c12]

The compound of Example 68 disclosed in Korean Patent Publication No. 10-2013-0065634 (WO 2011/120604 A1) was prepared as the compound of Comparative Example 2.

<Comparative Example 3> Preparation of 1-(2-oxo-1,3-dihydrobenzimidazol-4-yl)-3-[[2-(1-piperidyl)-6-(trifluoromethyl)-3-pyridyl]methyl]urea

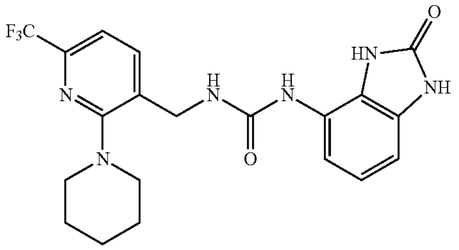 [SMILES: O=C(NCc1ccc(C(F)(F)F)nc1N1CCCCC1)Nc1cccc2[nH]c(=O)[nH]c12]

The compound of Example 71 disclosed in Korean Patent Publication No. 10-2013-0065634 (WO 2011/120604 A1) was prepared as the compound of Comparative Example 3.

<Experimental Example 1> Evaluation of Antagonism Against TRPV1 (Transient Receptor Potential Vanilloid-1) Receptor Activators (In Vitro)

As emphasized above, it has been reported that the side effect of increasing body temperature of the first-generation TRPV1 antagonists developed to date is due to antagonism to all TRPV1 receptor activators (capsaicin, heat, pH, NADA). In particular, it has been reported that blocking 100% of pH among the TRPV1 receptor activators caused excessive increase of body temperature, and blocking 20% or less caused proton activation at a high concentration to cause excessive decrease of body temperature. That is, in the development of TRPV1 antagonists, while blocking TRPV1 activation caused by capsaicin and heat, but inducing an appropriate inhibition of about 20% to 80% of pH, it may lead to the effect of not only alleviating pain but also reducing side effects such as abnormal body temperature.

Hereinafter, it was evaluated whether the example compounds provided in one aspect of the present invention could block TRPV1 activation caused by capsaicin, but induce an appropriate inhibition of about 20% to 80% of pH, thereby alleviating pain as well as reducing side effects such as abnormal body temperature.

Antagonism to capsaicin and pH, the hTRPV1 receptor activators, was searched, and the target was set as $IC_{50}$ (CAP) <15 nM (efficacy) and 80% inhibition for pH=6 (non-hyperthermia). This is because the $IC_{50}$ (CAP) of Mavatrep, a control clinical drug, was investigated as 13.8 nM in our own experiment, and when pH antagonism was less than 80% inhibition, it was considered non-hyperthermia.

$Ca^{2+}$ Influx Assay

PrecisION™ hTRPV1-HEK recombinant cells (CYL3063) were purchased from Millipore and used as cells for human TRPV1 (hTRPV1) antagonist assay. DME/F-12 (HyClone) (10% FBS, 1% NEAA, 1% Penicillin streptomycin) was used as a medium, and Fluo4-NW (Molecular Probes, F-36206) was used as an ELISA kit. After culturing the above cells under the conditions of 37° C. and 5% $CO_2$, the cells were inoculated in a 96-well plate at the density of $5\times10^4$ cells/well, followed by culture for 16 hours. Then, the medium was removed and 100 uL of a staining solution was put into each well, followed by culture for 30 minutes under the conditions of 37° C. and 5% $CO_2$. Thereafter, the cells were acclimatized to room temperature for 15 minutes, and the test substances (example compounds and comparative example compounds of the present invention) were added to each well, followed by culture at room temperature for 15 minutes. After diluting capsaicin (Sigma, M2028) to a concentration of 10 nM, it was put into each well of the plate and fluorescence was measured (ex485/em535). In the above experiment, the efficacy of the drug was evaluated using BCTC as a representative TRPV1 antagonist.

Evaluation of Human pH Inhibitory Activity

PrecisION™ hTRPV1-HEK recombinant cells (CYL3063) were purchased from Millipore and used. After culturing the above cells under the conditions of 37° C. and 5% $CO_2$, the cells were inoculated in a 96-well plate at the density of $5\times10^4$ cells/well, followed by culture for 16 hours. Then, the medium was removed and 100 uL of a staining solution was put into each well, followed by culture for 30 minutes under the conditions of 37° C. and 5% $CO_2$. After 30 minutes, all of the existing staining solution was removed and replaced with 100 uL of HBSS. Thereafter, the cells were acclimatized to room temperature for 15 minutes, and the test substances (example compounds and comparative example compounds of the present invention) were added to each well, followed by culture at room temperature for 15 minutes. Then, the final pH was adjusted to 6.0 using MES, and fluorescence was measured (ex485/em535). In the pH assay, the efficacy of the drug was evaluated using BCTC as a TRPV1 antagonist.

The in vitro test results of <Experimental Example 1> were combined with the in vivo test results of <Experimental Example 2>, which are shown in Table 2 below.

<Experimental Example 2> Evaluation of Bioavailability (BA)

Potency, ADME, and toxicity properties are important for new drug candidates, and as pharmacokinetic properties, they should have a blood concentration profile above a certain level, and based on this, it is very important to check whether the PK-PD correlation is good. Using the PK parameters of new drug candidates obtained from experimental animals such as rats or mice, blood concentration and drug efficacy can be predicted in humans through allometric scaling or PK-PD prediction. For this purpose, it is important to measure Cl and Vss, which determine the dose and administration interval, and to obtain PK parameters such as Cmax, $t_{1/2}$ and AUCall during oral administration. In addition, basic information related to metabolic enzymes, transporters, and tissue distribution of candidate substances can be obtained, and inappropriate physical properties can be estimated. The information obtained through such an analysis can provide important decision criteria for deriving an optimal candidate, as well as help in the molecular design and development of more efficient drugs.

Test Method

SD rats (Coatec, Hana Trading Co., Ltd., 7-8 weeks old, male, n=4, 250-300 g) were used for the experiment. The rats were bred in a small animal breeding room (experimental animal center) set at a temperature of 22±2° C., a relative humidity of 50±5%, an illumination time of 12 hours (08:00~20:00), and an illumination intensity of 150 to 300 lux. Feed was fed freely during the entire test period, and RO water was provided freely. Before oral administration of the test substances (example compounds and comparative example compounds of the present invention), the rats were fasted for 16 hours.

The dosage of the example compounds and comparative example compounds of the present invention was 5 mg/kg when administered intravenously and 10 mg/kg when administered orally. For intravenous administration, a clear solution in which 10% DMSO, 10% Cremophor EL, and 80% PEG400 were dissolved was administered. For oral administration, a solution or suspension in which 10% DMSO and 10% Cremophor EL were dissolved in 80% DDW was administered.

After the intravenous or oral administration, blood was collected at 5 minutes, 15 minutes, 30 minutes, 1 hour, 2 hours, 4 hours, 6 hours and 8 hours, and the concentrations of the test substances (example compounds and comparative example compounds of the present invention) in plasma were measured by LC-MS/MS.

After adding 80 μl of acetonitrile (including internal standard) to 20 μl of plasma, centrifugation was performed for 5 minutes at 15,000 rpm at 4° C. with vortexing. The supernatant obtained after the centrifugation was analyzed by LC-MS/MS. For HPLC, Nexera XR system (Shimadzu, Japan) was used, and for mass spectrometer, TSQ vantage triple quadruple (Thermo, USA) was used.

| HPLC Condition | |
|---|---|
| HPLC system | Nexera XR system (Shimadzu, Japan) |
| Column | Kintex XB-C18 column<br>(2.1 × 100 mm, 2.6 μm, particle size: Phenomenex, USA) |
| Injection volume | 2 μl |
| Mobile Phase | (A) 0.1% formic acid in water<br>(B) 0.1% formic acid in acetonitrile |
| Sample analysis time | 3-3.5 min |
| Retention time | 2-2.06 min |

| Mass spectrometry Condition | |
|---|---|
| System of Analysis | TSQ vantage triple quadruple (Thermo, USA) |
| Ion Source type | Turbo Spray Ionization |

The PK parameters were calculated with a non-compartmental analysis model using Phoenix WinNonlin 6.4 version (Pharsight, USA) program.

AUC (area under the plasma concentration-time curve) up to 8 hours was calculated from the measured plasma concentration by the trapezoidal rule, and the oral absorption rate (F %) was calculated from the ratio to the AUC when the same dose was administered intravenously. AUC was calculated using the linear trapezoidal rule in the rising plasma-level phase and the logarithmic trapezoidal rule in the declining phase.

The results are shown in Table 2 below.

TABLE 2

| Test substance | hTRPV1 IC$_{50}$ [cap], nM | hTRPV1 pH (%, 3 μM) | Bioavailability F (%) |
|---|---|---|---|
| Example 1 | 36.96 | 78.62 | |
| Example 2 | 28.76 | 86.72 | |
| Example 3 | 15.74 | 52.56 | 13.2 |
| Example 4 | 11.33 | 49.86 | 12.5 |
| Example 5 | 16.26 | 94.79 | |
| Example 6 | 10.65 | 76.92 | |
| Example 7 | 23.30 | 89.87 | |
| Example 8 | 27.34 | 81.24 | |
| Example 9 | >50 | NT | |
| Example 10 | 12.95 | 53.26 | 25.9 |
| Example 11 | 37.84 | 88.23 | |
| Example 12 | 31.47 | 81.25 | |
| Example 13 | 13.74 | 30.67 | 35.6 |
| Example 14 | 34.5 | 94.03 | |
| Example 15 | 201.7 | NT | |
| Example 16 | 86.0 | 97.34 | |
| Example 17 | 56.9 | 83.20 | |
| Example 18 | 116.8 | NT | |
| Example 19 | 409.8 | NT | |
| Example 20 | 53.5 | 86.79 | |
| Example 21 | 26.1 | 79.89 | |
| Example 22 | 31.2 | 90.86 | |
| Example 23 | 217.2 | NT | |
| Example 24 | | | |
| Example 25 | 34.10 | 89.76 | |
| Example 26 | 54.41 | 95.11 | |
| Example 27 | 40.87 | 78.45 | |
| Example 28 | >100 | NT | |
| Example 29 | >100 | NT | |
| Example 30 | 14.25 | 48.62 | |
| Example 31 | 26.01 | 82.34 | |
| Example 32 | 23.72 | 67.88 | |
| Example 33 | 27.44 | 69.89 | |
| Example 34 | 11.09 | 37.85 | |
| Example 35 | 11.76 | 95.87 | |
| Example 36 | 11.04 | 100.46 | |
| Example 37 | | | |
| Example 38 | | | |
| Example 39 | 35.4 | 67.89 | |
| Example 40 | 177.5 | NT | |
| Example 41 | 123.1 | NT | |
| Example 42 | 35.42 | 78.89 | |
| Example 43 | 19.66 | 87.68 | |
| Example 44 | | | |
| Example 45 | 79.3 | 48.71 | |
| Example 46 | 72.9 | 57.38 | |
| Example 47 | 15.89 | 37.26 | |
| Example 48 | 9.95 | 29.43 | |
| Example 49 | 19.90 | 21.37 | |
| Example 50 | 41.28 | 34.22 | |
| Example 51 | >160 | NT | |
| Example 52 | >160 | NT | |
| Example 53 | 79.78 | 78.21 | |
| Example 54 | 55.7 | 63.44 | |
| Example 55 | >160 | NT | |
| Example 56 | 26.04 | 68.23 | |
| Example 57 | 39.81 | 61.78 | |
| Example 58 | 102.98 | NT | |
| Example 59 | 40.71 | 59.32 | |
| Example 60 | 23.66 | 67.19 | |
| Example 61 | | | |
| Example 62 | | | |
| Example 63 | 10.33 | 0.53 | |
| Example 64 | >160 | NT | |
| Example 65 | >160 | NT | |
| Example 66 | >160 | NT | |
| Example 67 | >160 | NT | |
| Example 68 | 138.88 | NT | |
| Comparative Example 1 | 18.45 | 0.78 | 2.3 |
| Comparative Example 2 | 23.37 | | 1 |
| Comparative Example 3 | 13.50 | 82.51 | 3.0 |

*NT = Not Tested

As shown in Table 2, the example compounds provided in one aspect of the present invention block the TRPV1 activation caused by capsaicin, but induce an appropriate inhibition of about 20% to 80% of pH, thereby the compounds have effects of alleviating pain and reducing side effects such as abnormal body temperature. In addition, it was confirmed that the compounds of the present invention have a high PK value, so that the example compounds are easily absorbed into the body, and thus, thermoneutrality is also maintained.

On the other hand, the compounds of Comparative Examples 1 to 3 block the TRPV1 activation caused by capsaicin, but inhibit pH less than or more than necessary, that is, out of the appropriate range of 20% to 80%. In addition, it was confirmed that the compounds of Comparative Examples have a low PK value, and thus, the compounds are not easily absorbed into the body, so that there is a problem in that they are difficult to use as an actual analgesic.

<Manufacturing Example 1> Preparation of Powders

| | |
|---|---|
| Derivative represented by formula 1 | 2 g |
| Lactose | 1 g |

Powders were prepared by mixing all the above components, which were filled in airtight packs.

<Manufacturing Example 2> Preparation of Tablets

| | |
|---|---|
| Derivative represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

<Manufacturing Example 3> Preparation of Capsules

| | |
|---|---|
| Derivative represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<Manufacturing Example 4> Preparation of Injectable Solutions

| | |
|---|---|
| Derivative represented by formula 1 | 100 mg |
| Mannitol | 180 mg |
| $Na_2HPO_4$•$2H_2O$ | 26 mg |
| Distilled water | 2974 mg |

Injectable solutions were prepared by containing all the above components in the amounts indicated according to the conventional method for preparing injectable solutions.

<Manufacturing Example 5> Preparation of Health Functional Foods

| | |
|---|---|
| Derivative represented by formula 1 | 500 ng |
| Vitamin complex | proper amount |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate, monobasic | 15 mg |
| Calcium phosphate, dibasic | 55 mg |
| Potassium citrate | 90 mg |
| Calcium carbonate | 100 mg |
| Magnesium chloride | 24.8 mg |

The vitamins and minerals appropriate for health functional foods were mixed according to the preferred mixing ratio but the composition ratio can be adjusted arbitrarily. After mixing the above components according to the conventional method for preparing health functional foods, granules were prepared and the granules were used for the preparation of health functional foods according to the conventional method.

<Manufacturing Example 6> Preparation of Health Beverages

| | |
|---|---|
| Derivative represented by formula 1 | 500 ng |
| Citric acid | 1000 mg |
| Oligosaccharide | 100 g |
| Maesil (*Prunus mume*) Extract | 2 g |
| Taurine | 1 g |
| Purified water | up to 900 mℓ |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and ethnic preferences such as demand class, demand country, and purpose of use, etc.

What is claimed is:

1. A compound represented by formula 1 below, a stereoisomer thereof, a solvate thereof, a hydrate thereof or a pharmaceutically acceptable salt thereof:

[Formula 1]

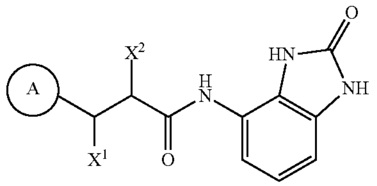

wherein:

$X^1$ and $X^2$ together form a pi bond; and

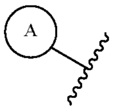

is unsubstituted or substituted 5-6 membered heteroaryl containing at least one heteroatom selected from the group consisting of N, O and S, or unsubstituted or substituted phenyl, wherein the substituted 5-6 membered heteroaryl and the substituted phenyl are independently substituted with at least one substituent selected from the group consisting of:

$C_{1-7}$ straight or branched alkyl unsubstituted or substituted with at least one halogen or hydroxy group; $C_{2-7}$ straight or branched alkynyl; $C_{3-6}$ cycloalkyl unsubstituted or substituted with at least one $C_{1-5}$ straight or branched alkyl; 5-6 membered heterocycloalkyl containing at least one heteroatom selected from the group consisting of N and O unsubstituted or substituted with at least one $C_{1-5}$ straight or branched alkyl; —$NR^1R^2$; —$OR^3$; —$SR^4$; $C_6$ aryl unsubstituted or substituted with at least one halogen or $C_{1-5}$ straight or branched alkyl; and 5 membered heteroaryl containing at least one heteroatom selected from the group consisting of N, O and S, $R^1$ and $R^2$ are independently $C_{1-5}$ straight or branched alkyl, $R^3$ is $C_{1-7}$ straight or branched alkyl unsubstituted or substituted with at least one halogen, $C_{3-6}$ cycloalkyl, or $C_{1-5}$ straight or branched alkyl substituted with $C_{3-6}$ cycloalkyl unsubstituted or substituted with at least one methyl, $R^4$ is $C_{1-7}$ straight or branched alkyl unsubstituted or substituted with at least one halogen, $C_{3-4}$ cycloalkyl, or $C_{1-5}$ straight or branched alkyl substituted with $C_{3-6}$ cycloalkyl unsubstituted or substituted with at least one methyl.

2. The compound, the stereoisomer thereof, the solvate thereof, the hydrate thereof or the pharmaceutically acceptable salt thereof according to claim 1, wherein:
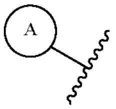
is substituted pyridinyl.
3. The compound, the stereoisomer thereof, the solvate thereof, the hydrate thereof or the pharmaceutically acceptable salt thereof according to claim 1, wherein:
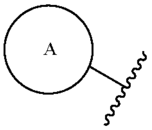
is
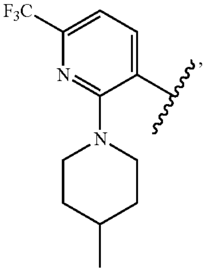
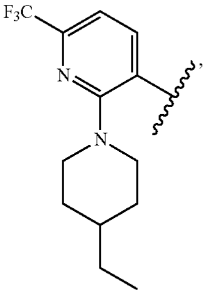
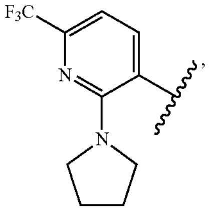
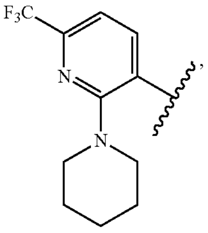
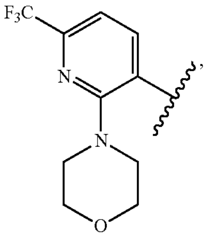
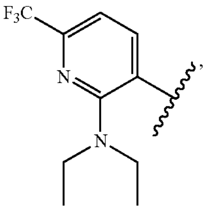
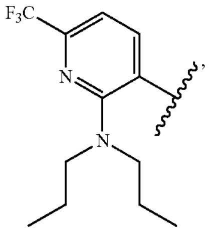
-continued
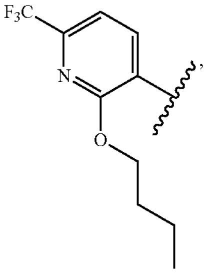
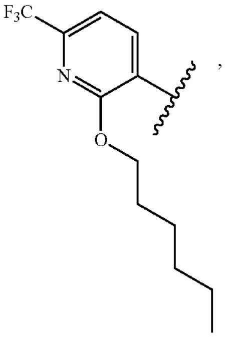
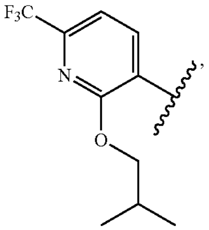
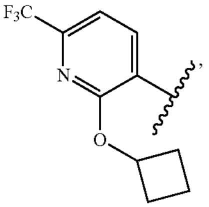
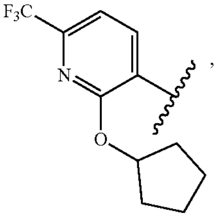
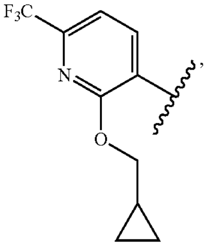
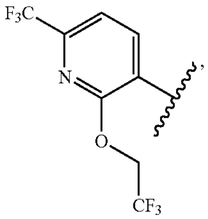
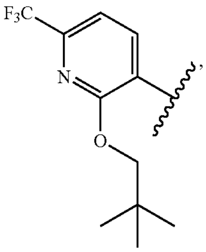
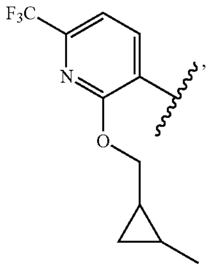
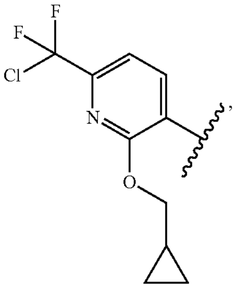
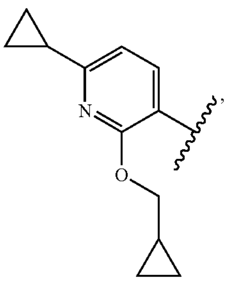
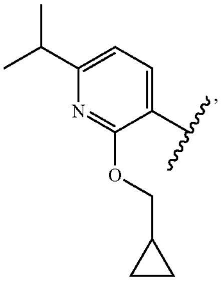

-continued
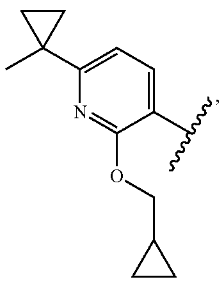
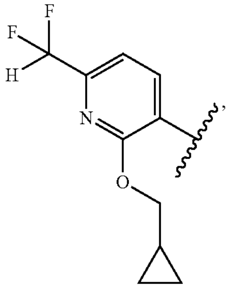
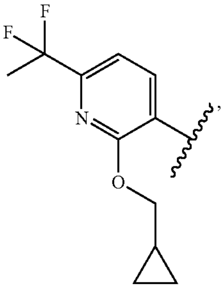
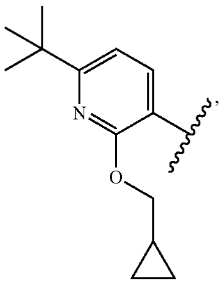
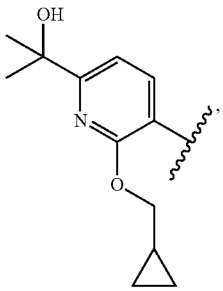
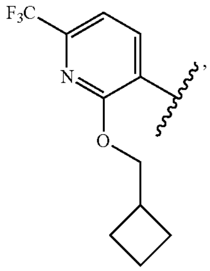
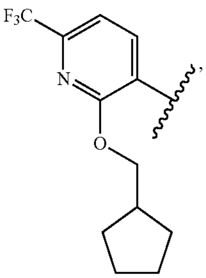
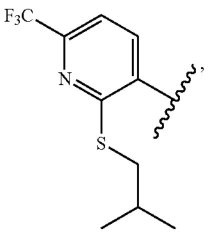
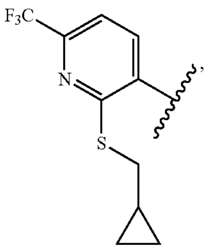
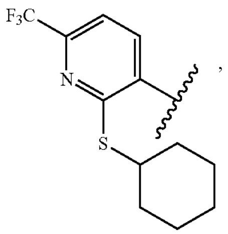
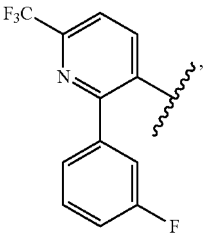
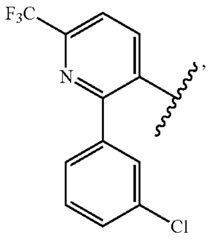
-continued
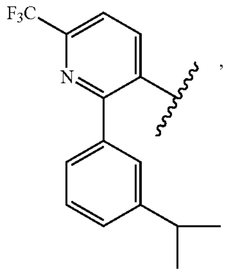
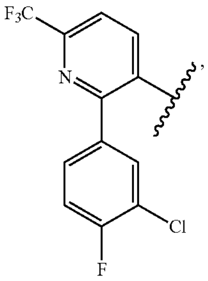
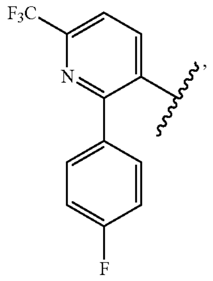
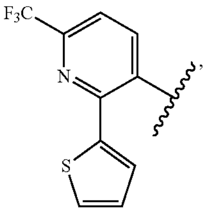
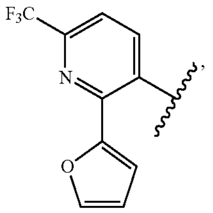
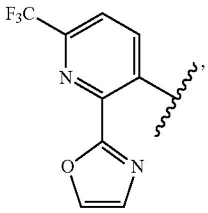
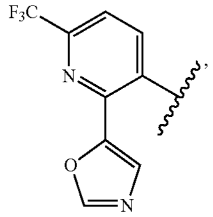
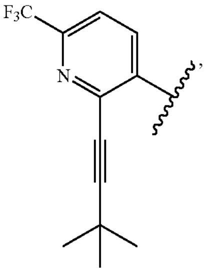
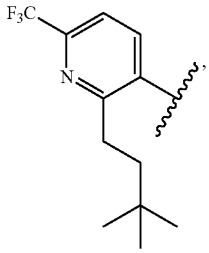
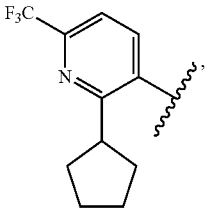
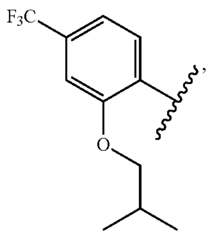
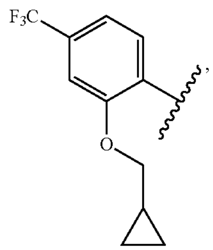

-continued

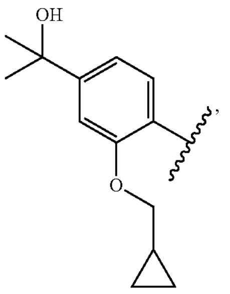

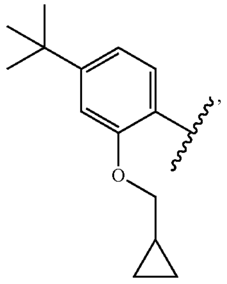

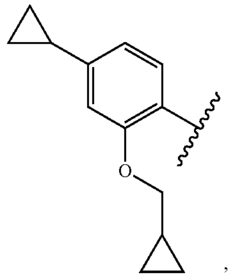

,

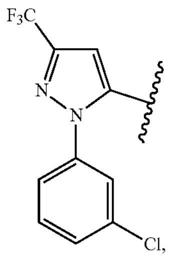

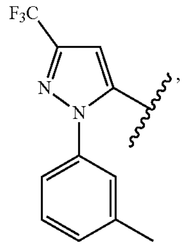

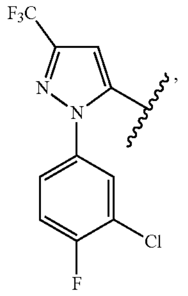

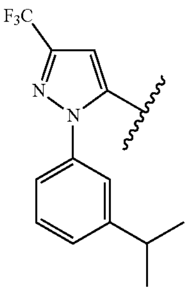

,

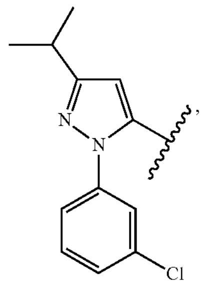

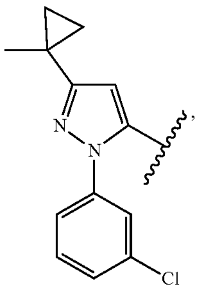

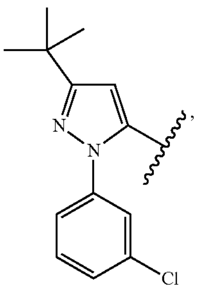

-continued

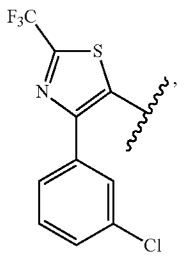

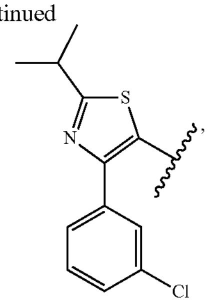

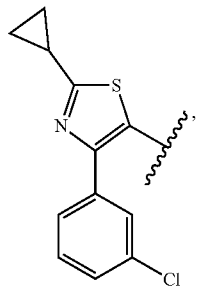

, or

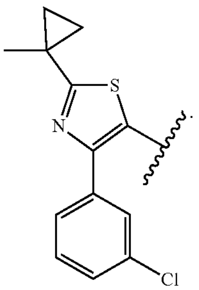

4. The compound, the stereoisomer thereof, the solvate thereof, the hydrate thereof or the pharmaceutically acceptable salt thereof according to claim 1, wherein the compound represented by formula 1 is selected from the group consisting of the following compounds:

(1) (E)-3-(2-(4-methylpiperidin-1-yl)-6-(trifluoromethyl)pyridin-3-yl)-N-(2-oxo-2,3-dihydro-1H-benzo[d]imidazol-4-yl)acrylamide;

(2) (E)-3-(2-(4-ethylpiperidin-1-yl)-6-(trifluoromethyl)pyridin-3-yl)-N-(2-oxo-2,3-dihydro-1H-benzo[d]imidazol-4-yl)acrylamide;

(3) (E)-N-(2-oxo-2,3-dihydro-1H-benzo[d]imidazol-4-yl)-3-(2-(pyrrolidin-1-yl)-6-(trifluoromethyl)pyridin-3-yl)acrylamide;

(4) (E)-N-(2-oxo-2,3-dihydro-1H-benzo[d]imidazol-4-yl)-3-(2-(piperidin-1-yl)-6-(trifluoromethyl)pyridin-3-yl)acrylamide;

(5) (E)-3-(2-morpholino-6-(trifluoromethyl)pyridin-3-yl)-N-(2-oxo-2,3-dihydro-1H-benzo[d]imidazol-4-yl)acrylamide;

(6) (E)-3-(2-(diethylamino)-6-(trifluoromethyl)pyridin-3-yl)-N-(2-oxo-2,3-dihydro-1H-benzo[d]imidazol-4-yl)acrylamide;

(7) (E)-3-(2-(dipropylamino)-6-(trifluoromethyl)pyridin-3-yl)-N-(2-oxo-2,3-dihydro-1H-benzo[d]imidazol-4-yl)acrylamide;

(8) (E)-3-(2-butoxy-6-(trifluoromethyl)pyridin-3-yl)-N-(2-oxo-2,3-dihydro-1H-benzo[d]imidazol-4-yl)acrylamide;

(9) (E)-3-(2-(hexyloxy)-6-(trifluoromethyl)pyridin-3-yl)-N-(2-oxo-2,3-dihydro-1H-benzo[d]imidazol-4-yl)acrylamide;

(10) (E)-3-(2-isobutoxy-6-(trifluoromethyl)pyridin-3-yl)-N-(2-oxo-2,3-dihydro-1H-benzo[d]imidazol-4-yl)acrylamide;

(11) (E)-3-(2-cyclobutoxy-6-(trifluoromethyl)pyridin-3-yl)-N-(2-oxo-2,3-dihydro-1H-benzo[d]imidazol-4-yl)acrylamide;

(12) (E)-3-(2-(cyclopentyloxy)-6-(trifluoromethyl)pyridin-3-yl)-N-(2-oxo-2,3-dihydro-1H-benzo[d]imidazol-4-yl)acrylamide;

(13) (E)-3-(2-(cyclopropylmethoxy)-6-(trifluoromethyl)pyridin-3-yl)-N-(2-oxo-2,3-dihydro-1H-benzo[d]imidazol-4-yl)acrylamide;

(14) (E)-N-(2-oxo-2,3-dihydro-1H-benzo[d]imidazol-4-yl)-3-(2-(2,2,2-trifluoroethoxy)-6-(trifluoromethyl)pyridin-3-yl)acrylamide;

(15) (E)-3-(2-(neopentyloxy)-6-(trifluoromethyl)pyridin-3-yl)-N-(2-oxo-2,3-dihydro-1H-benzo[d]imidazol-4-yl)acrylamide;

(16) (E)-3-(2-((2-methylcyclopropyl)methoxy)-6-(trifluoromethyl)pyridin-3-yl)-N-(2-oxo-2,3-dihydro-1H-benzo[d]imidazol-4-yl)acrylamide;

(17) (E)-3-(6-(chlorodifluoromethyl)-2-(cyclopropylmethoxy)pyridin-3-yl)-N-(2-oxo-2,3-dihydro-1H-benzo[d]imidazol-4-yl)acrylamide;

(18) (E)-3-(6-cyclopropyl-2-(cyclopropylmethoxy)pyridin-3-yl)-N-(2-oxo-2,3-dihydro-1H-benzo[d]imidazol-4-yl)acrylamide;

(19) (E)-3-(2-(cyclopropylmethoxy)-6-isopropylpyridin-3-yl)-N-(2-oxo-2,3-dihydro-1H-benzo[d]imidazol-4-yl)acrylamide;

(20) (E)-3-(2-(cyclopropylmethoxy)-6-(1-methylcyclopropyl)pyridin-3-yl)-N-(2-oxo-2,3-dihydro-1H-benzo[d]imidazol-4-yl)acrylamide;

(21) (E)-3-(2-(cyclopropylmethoxy)-6-(difluoromethyl)pyridin-3-yl)-N-(2-oxo-2,3-dihydro-1H-benzo[d]imidazol-4-yl)acrylamide;

(22) (E)-3-(2-(cyclopropylmethoxy)-6-(1,1-difluoroethyl)pyridin-3-yl)-N-(2-oxo-2,3-dihydro-1H-benzo[d]imidazol-4-yl)acrylamide;

(23) (E)-3-(6-(tert-butyl)-2-(cyclopropylmethoxy)pyridin-3-yl)-N-(2-oxo-2,3-dihydro-1H-benzo[d]imidazol-4-yl)acrylamide;

(24) (E)-3-(2-(cyclopropylmethoxy)-6-(2-hydroxypropan-2-yl)pyridin-3-yl)-N-(2-oxo-2,3-dihydro-1H-benzo[d]imidazol-4-yl)acrylamide;

(25) (E)-3-(2-(cyclobutylmethoxy)-6-(trifluoromethyl)pyridin-3-yl)-N-(2-oxo-2,3-dihydro-1H-benzo[d]imidazol-4-yl)acrylamide;

(26) (E)-3-(2-(cyclopentylmethoxy)-6-(trifluoromethyl)pyridin-3-yl)-N-(2-oxo-2,3-dihydro-1H-benzo[d]imidazol-4-yl)acrylamide;

(27) (E)-3-(2-(isobutylthio)-6-(trifluoromethyl)pyridin-3-yl)-N-(2-oxo-2,3-dihydro-1H-benzo[d]imidazol-4-yl)acrylamide;

(28) (E)-3-(2-((cyclopropylmethyl)thio)-6-(trifluoromethyl)pyridin-3-yl)-N-(2-oxo-2,3-dihydro-1H-benzo[d]imidazol-4-yl)acrylamide;

(29) (E)-3-(2-(cyclohexylthio)-6-(trifluoromethyl)pyridin-3-yl)-N-(2-oxo-2,3-dihydro-1H-benzo[d]imidazol-4-yl)acrylamide;

(30) (E)-3-(2-(3-fluorophenyl)-6-(trifluoromethyl)pyridin-3-yl)-N-(2-oxo-2,3-dihydro-1H-benzo[d]imidazol-4-yl)acrylamide;

(31) (E)-3-(2-(3-chlorophenyl)-6-(trifluoromethyl)pyridin-3-yl)-N-(2-oxo-2,3-dihydro-1H-benzo[d]imidazol-4-yl)acrylamide;

(32) (E)-3-(2-(3-isopropylphenyl)-6-(trifluoromethyl)pyridin-3-yl)-N-(2-oxo-2,3-dihydro-1H-benzo[d]imidazol-4-yl)acrylamide;

(33) (E)-3-(2-(3-chloro-4-fluorophenyl)-6-(trifluoromethyl)pyridin-3-yl)-N-(2-oxo-2,3-dihydro-1H-benzo[d]imidazol-4-yl)acrylamide;

(34) (E)-3-(2-(4-fluorophenyl)-6-(trifluoromethyl)pyridin-3-yl)-N-(2-oxo-2,3-dihydro-1H-benzo[d]imidazol-4-yl)acrylamide;

(35) (E)-N-(2-oxo-2,3-dihydro-1H-benzo[d]imidazol-4-yl)-3-(2-(thiophen-2-yl)-6-(trifluoromethyl)pyridin-3-yl)acrylamide;

(36) (E)-3-(2-(furan-2-yl)-6-(trifluoromethyl)pyridin-3-yl)-N-(2-oxo-2,3-dihydro-1H-benzo[d]imidazol-4-yl)acrylamide;

(37) (E)-3-(2-(oxazol-2-yl)-6-(trifluoromethyl)pyridin-3-yl)-N-(2-oxo-2,3-dihydro-1H-benzo[d]imidazol-4-yl)acrylamide;

(38) (E)-3-(2-(oxazol-5-yl)-6-(trifluoromethyl)pyridin-3-yl)-N-(2-oxo-2,3-dihydro-1H-benzo[d]imidazol-4-yl)acrylamide;

(39) (E)-3-(2-(3,3-dimethyl-1-butyn-1-yl)-6-(trifluoromethyl)pyridin-3-yl)-N-(2-oxo-2,3-dihydro-1H-benzo[d]imidazol-4-yl)acrylamide;

(40) (E)-3-(2-(3,3-dimethylbutyl)-6-(trifluoromethyl)pyridin-3-yl)-N-(2-oxo-2,3-dihydro-1H-benzo[d]imidazol-4-yl)acrylamide;

(41) (E)-3-(2-cyclopentyl-6-(trifluoromethyl)pyridin-3-yl)-N-(2-oxo-2,3-dihydro-1H-benzo[d]imidazol-4-yl)acrylamide;

(42) (E)-3-(2-isobutoxy-4-(trifluoromethyl)phenyl)-N-(2-oxo-2,3-dihydro-1H-benzo[d]imidazol-4-yl)acrylamide;

(43) (E)-3-(2-(cyclopropylmethoxy)-4-(trifluoromethyl)phenyl)-N-(2-oxo-2,3-dihydro-1H-benzo[d]imidazol-4-yl)acrylamide;

(44) (E)-3-(2-(cyclopropylmethoxy)-4-(2-hydroxypropan-2-yl)phenyl)-N-(2-oxo-2,3-dihydro-1H-benzo[d]imidazol-4-yl)acrylamide;

(45) (E)-3-(4-(tert-butyl)-2-(cyclopropylmethoxy)phenyl)-N-(2-oxo-2,3-dihydro-1H-benzo[d]imidazol-4-yl)acrylamide;

(46) (E)-3-(4-cyclopropyl-2-(cyclopropylmethoxy)phenyl)-N-(2-oxo-2,3-dihydro-1H-benzo[d]imidazol-4-yl)acrylamide;

(47) (E)-3-(1-(3-chlorophenyl)-3-(trifluoromethyl)-1H-pyrazol-5-yl)-N-(2-oxo-2,3-dihydro-1H-benzo[d]imidazol-4-yl)acrylamide;

(48) (E)-N-(2-oxo-2,3-dihydro-1H-benzo[d]imidazol-4-yl)-3-(1-(m-tolyl)-3-(trifluoromethyl)-1H-pyrazol-5-yl)acrylamide;

(49) (E)-3-(1-(3-chloro-4-fluorophenyl)-3-(trifluoromethyl)-1H-pyrazol-5-yl)-N-(2-oxo-2,3-dihydro-1H-benzo[d]imidazol-4-yl)acrylamide;

(50) (E)-3-(1-(3-isopropylphenyl)-3-(trifluoromethyl)-1H-pyrazol-5-yl)-N-(2-oxo-2,3-dihydro-1H-benzo[d]imidazol-4-yl)acrylamide;

(51) (E)-3-(1-(3-chlorophenyl)-3-isopropyl-1H-pyrazol-5-yl)-N-(2-oxo-2,3-dihydro-1H-benzo[d]imidazol-4-yl)acrylamide;

(52) (E)-3-(1-(3-chlorophenyl)-3-(1-methylcyclopropyl)-1H-pyrazol-5-yl)-N-(2-oxo-2,3-dihydro-1H-benzo[d]imidazol-4-yl)acrylamide;

(53) (E)-3-(3-(tert-butyl)-1-(3-chlorophenyl)-1H-pyrazol-5-yl)-N-(2-oxo-2,3-dihydro-1H-benzo[d]imidazol-4-yl)acrylamide;

(54) (E)-3-(4-(3-chlorophenyl)-2-(trifluoromethyl)thiazol-5-yl)-N-(2-oxo-2,3-dihydro-1H-benzo[d]imidazol-4-yl)acrylamide;

(55) (E)-3-(4-(3-chlorophenyl)-2-isopropylthiazol-5-yl)-N-(2-oxo-2,3-dihydro-1H-benzo[d]imidazol-4-yl)acrylamide;

(56) (E)-3-(4-(3-chlorophenyl)-2-cyclopropylthiazol-5-yl)-N-(2-oxo-2,3-dihydro-1H-benzo[d]imidazol-4-yl)acrylamide;

(57) (E)-3-(4-(3-chlorophenyl)-2-(1-methylcyclopropyl)thiazol-5-yl)-N-(2-oxo-2,3-dihydro-1H-benzo[d]imidazol-4-yl)acrylamide; and

(58) (E)-3-(2-(tert-butyl)-4-(3-chlorophenyl)thiazol-5-yl)-N-(2-oxo-2,3-dihydro-1H-benzo[d]imidazol-4-yl) acrylamide.

5. A pharmaceutical composition for treating pain containing the compound of claim 1, a stereoisomer thereof, a solvate thereof, a hydrate thereof or a pharmaceutically acceptable salt thereof as an active ingredient.

6. The pharmaceutical composition for treating pain according to claim 5, wherein the compound exhibits a preventive or therapeutic activity for pain by inhibiting transient receptor potential vanilloid-1 (TRPV-1) receptor activators.

7. An analgesic composition for treating or alleviating pain containing the compound of claim 1, a stereoisomer thereof, a solvate thereof, a hydrate thereof or a pharmaceutically acceptable salt thereof as an active ingredient.

8. A pharmaceutical kit for preventing or treating pain comprising a first component containing the compound of claim 1, a stereoisomer thereof, a solvate thereof, a hydrate thereof or a pharmaceutically acceptable salt thereof as an active ingredient; and a second component containing an analgesic as an active ingredient.

9. A method of treating or alleviating pain comprising administering the compound represented by formula 1 of claim 1, a solvate thereof, or a pharmaceutically acceptable salt thereof as an active ingredient to a subject in need thereof.

10. The method according to claim 9, wherein the compound exhibits a preventive or therapeutic activity for pain by inhibiting transient receptor potential vanilloid-1 (TRPV-1) receptor activators.

* * * * *